(12) United States Patent
Smith et al.

(10) Patent No.: US 8,579,176 B2
(45) Date of Patent: Nov. 12, 2013

(54) SURGICAL STAPLING AND CUTTING DEVICE AND METHOD FOR USING THE DEVICE

(75) Inventors: Kevin W. Smith, Coral Gables, FL (US); Matthew A. Palmer, Miami, FL (US); Korey Robert Kline, Miami, FL (US); Derek Dee Deville, Miami, FL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1308 days.

(21) Appl. No.: 11/491,626

(22) Filed: Jul. 24, 2006

(65) Prior Publication Data

US 2007/0027469 A1   Feb. 1, 2007

Related U.S. Application Data

(60) Provisional application No. 60/702,643, filed on Jul. 26, 2005, provisional application No. 60/760,000, filed on Jan. 18, 2006, provisional application No. 60/811,950, filed on Jun. 8, 2006.

(51) Int. Cl.
*A61B 17/068*   (2006.01)

(52) U.S. Cl.
USPC .... 227/175.1; 227/19; 227/175.2; 227/176.1; 606/139; 606/219

(58) Field of Classification Search
USPC ............... 227/19, 180.1, 176.1, 175.2, 175.1, 227/178.1, 181.1; 606/139, 153, 219, 142, 606/167
See application file for complete search history.

(56) References Cited

U.S. PATENT DOCUMENTS

| | | | |
|---|---|---|---|
| 4,488,523 A | * | 12/1984 | Shichman ................. 227/179.1 |
| 4,566,620 A | | 1/1986 | Green et al. |
| 4,608,981 A | | 9/1986 | Rothfuss et al. |

(Continued)

FOREIGN PATENT DOCUMENTS

| EP | 0 216 532 | 4/1987 |
|---|---|---|
| EP | 0 674 876 | 3/1995 |

(Continued)

OTHER PUBLICATIONS

U.S. Patent Application Publication US/2006/0212069 A1 dated Sep. 21, 2006 to Shelton, IV.

(Continued)

*Primary Examiner* — Scott A. Smith
(74) *Attorney, Agent, or Firm* — Mayback & Hoffman, P.A.; Gregory L. Mayback; Rebecca A. Tie

(57) ABSTRACT

A medical device includes a control handle having an articulation joint actuator, a surgical end effector, and a passive articulating joint connecting the end effector to the control handle. The articulation joint actuator, when unactuated, holds the passive articulation joint and, thereby, the end effector, in a substantially fixed articulation position, and, when actuated, releases the passive articulation joint into a freely articulating state to permit free articulation of the end effector with respect to the control handle dependent upon external forces acting upon the end effector. A method for operating the end effector includes retaining the passive articulation joint in a stable position with an articulation lock and actuating a release of the articulation lock to unlock the passive articulation joint and, thereby, permit articulating motion of the end effector through the passive articulation joint dependent upon the external forces acting upon the end effector.

30 Claims, 66 Drawing Sheets

(56) References Cited

U.S. PATENT DOCUMENTS

| | | | |
|---|---|---|---|
| 4,873,977 A | 10/1989 | Avant et al. | |
| 5,020,993 A | 6/1991 | Levandoski | |
| 5,139,513 A * | 8/1992 | Segato | 606/219 |
| 5,197,649 A * | 3/1993 | Bessler et al. | 227/179.1 |
| 5,219,111 A | 6/1993 | Bilotti | |
| 5,271,544 A | 12/1993 | Fox et al. | |
| 5,348,259 A | 9/1994 | Blanco et al. | |
| 5,355,897 A | 10/1994 | Pietrafitta et al. | |
| 5,417,203 A * | 5/1995 | Tovey et al. | 600/106 |
| 5,439,156 A * | 8/1995 | Grant et al. | 227/179.1 |
| 5,465,895 A | 11/1995 | Knodel et al. | |
| 5,507,426 A | 4/1996 | Young et al. | |
| 5,609,285 A | 3/1997 | Grant et al. | |
| 5,673,840 A | 10/1997 | Schulze et al. | |
| 5,759,151 A | 6/1998 | Sturges | |
| 5,797,537 A | 8/1998 | Oberlin et al. | |
| 5,984,864 A | 11/1999 | Fox | |
| 6,193,129 B1 | 2/2001 | Bittner et al. | |
| 6,250,532 B1 | 6/2001 | Green et al. | |
| 6,330,965 B1 | 12/2001 | Milliman et al. | |
| 6,644,532 B2 | 11/2003 | Green et al. | |
| 6,945,444 B2 | 9/2005 | Gresham et al. | |
| 6,964,363 B2 * | 11/2005 | Wales et al. | 227/175.1 |
| 6,981,628 B2 * | 1/2006 | Wales | 227/178.1 |
| 7,059,508 B2 | 6/2006 | Shelton, IV et al. | |
| 7,097,650 B2 | 8/2006 | Weller et al. | |
| 7,111,769 B2 * | 9/2006 | Wales et al. | 227/178.1 |
| 7,210,609 B2 | 5/2007 | Leiboff et | |
| 7,328,828 B2 * | 2/2008 | Ortiz et al. | 227/175.2 |
| 7,404,508 B2 | 7/2008 | Smith et al. | |
| 7,419,080 B2 | 9/2008 | Smith et al. | |
| 8,034,077 B2 | 10/2011 | Smith et al. | |
| 8,245,898 B2 | 8/2012 | Smith et al. | |
| 2004/0059338 A1 | 3/2004 | Ebner | |
| 2007/0221701 A1 | 9/2007 | Ortiz | |

FOREIGN PATENT DOCUMENTS

| | | |
|---|---|---|
| EP | 1 359 851 | 9/2010 |
| JP | 10-507384 | 7/1998 |
| JP | 11-192225 | 7/1999 |
| JP | 2001-190563 | 7/2001 |
| JP | 2003-17056 | 6/2003 |
| WO | 02/39909 | 5/2002 |
| WO | 03/005698 | 1/2003 |
| WO | 2004019710 | 3/2004 |
| WO | 2004112618 | 12/2004 |
| WO | 2007142625 A2 | 12/2007 |

OTHER PUBLICATIONS

European Search Report of European App. No. 10 00 7212 dated Nov. 30, 2012.
European Search Report of European App. No. 12 00 3870 dated Dec. 3, 2012.
European Search Report of European App. No. 12 00 3924 dated Dec. 4, 2012.

* cited by examiner

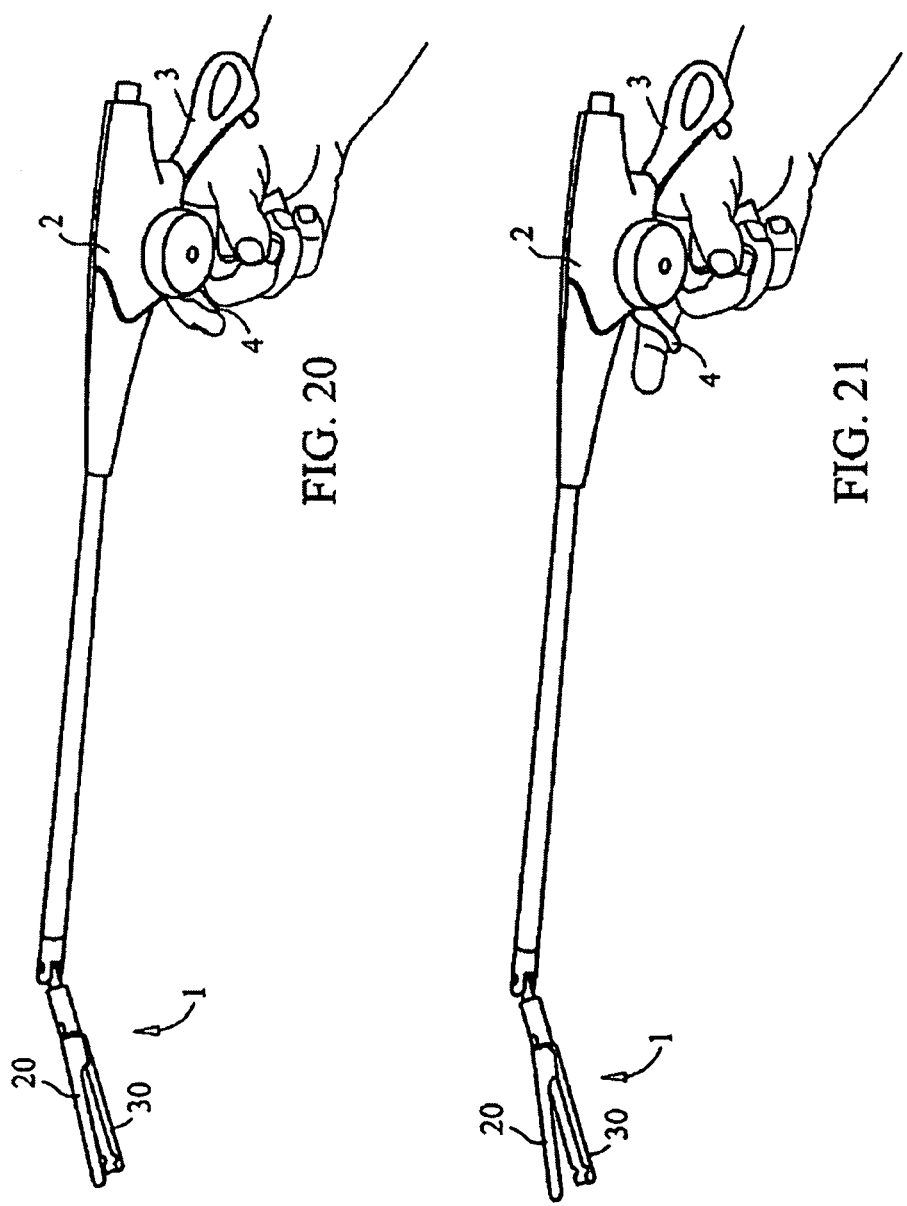

SURGICAL STAPLING AND CUTTING DEVICE AND METHOD FOR USING THE DEVICE

CROSS-REFERENCE TO RELATED APPLICATION

This application claims the priority, under 35 U.S.C. §119, of U.S. Provisional Patent Application Nos. 60/702,643 filed Jul. 26, 2005, 60/760,000 filed Jan. 18, 2006, and 60/811,950 filed Jun. 8, 2006, the entire disclosures of which are hereby incorporated herein by reference in their entireties.

STATEMENT REGARDING FEDERALLY SPONSORED RESEARCH OR DEVELOPMENT n/a

FIELD OF THE INVENTION

The present invention lies in the field of medical devices, in particular, in the field of surgical stapling instruments that are capable of applying lines of staples to tissue while cutting the tissue between those staple lines and, more particularly, to improvements relating to stapler instruments and improvements in processes for forming various components of such stapler instruments that include an articulating shaft. The device can be used, particularly, for stapling and cutting tissue during endoscopic or laparoscopic surgical procedures.

BACKGROUND OF THE INVENTION

Endoscopic surgical instruments are often preferred over traditional open surgical devices because a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally, these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895 to Knodel et al., are an example of an endoscopic surgical instrument that successfully positions an end effector by insertion and rotation.

One stapler manufactured by United States Surgical Corporation and described in U.S. Pat. Nos. 6,644,532 and 6,250,532 to Green et al. have an end effector that pivotally moves along a single plane in steps dependent upon activation of a lever that correspondingly moves along a single plane in similar steps. See FIGS. 31 and 32 therein. The U.S. Surgical Corp. stapler, however, is limited by the predetermined angles that it can achieve and by the limited side to side pivoting (−45 degrees to +45 degrees) that requires two hands for operation.

Depending upon the nature of the operation, it may be desirable to further adjust the positioning of the end effector of an endoscopic surgical instrument rather than being limited to insertion and rotation. In particular, it is often desirable to orient the end effector at an axis transverse to the longitudinal axis of the shaft of the instrument. The transverse movement of the end effector relative to the instrument shaft is conventionally referred to as "articulation". This articulated positioning permits the clinician to more easily engage tissue in some instances. In addition, articulated positioning advantageously allows an endoscope to be positioned behind the end effector without being blocked by the instrument shaft.

While the aforementioned non-articulating stapling and severing instruments have great utility and may be successfully employed in many surgical procedures, it is desirable to enhance their operation with the ability to articulate the end effector, thereby giving greater clinical flexibility in their use. Articulating surgical instruments generally use one or more firing bars that move longitudinally within the instrument shaft and through the articulation joint to fire the staples from the cartridge and to cut the tissue between the innermost staple lines. One common problem with these surgical instruments is control of the firing bar through the articulation joint. At the articulation joint, the end effector is longitudinally spaced away from the shaft so that the edges of the shaft and end effector do not collide during articulation. This gap must be filled with support material or structure to prevent the firing bar from buckling out of the joint when the single or multiple firing bars is subjected to longitudinal firing loads. What is needed is a support structure that guides and supports the single or multiple firing bars through the articulation joint and bends or curves as the end effector is articulated.

U.S. Pat. No. 5,673,840 to Schulze et al. describes a flexible articulation joint that is formed from an elastomeric or plastic material that bends at the flexible joint or "flex neck". The firing bars are supported and guided through a hollow tube within the flex neck. The flex neck is a portion of the jaw closure mechanism and moves longitudinally relative to the end effector, shaft, and firing bars when the jaws are closed on tissue. The firing bars then move longitudinally within the flex neck as the staples are fired and tissue is cut.

U.S. Pat. No. 5,797,537 to Oberlin et al. (owned by Richard-Allan Medical Industries, Inc.) describes an articulation joint that pivots around a pin, rather than bends around a flex joint. In this instrument, firing bars are supported between a pair of spaced support plates connected at one end to the shaft and at another end to the end effector. At least one of those connections is a slidable connection. The support plates extend through the articulation joint adjacent to the flexible drive member in the plane of articulation such that the support plates bend through the gap in the plane of articulation and the flexible firing bar bends against the support when the tip is articulated in one direction from its aligned position. U.S. Pat. No. 6,330,965 to Milliman et al from U.S. Surgical teaches the use of support plates that are fixedly attached to the shaft and slidably attached to the end effector.

Although these known support plates guide a firing bar through an articulation joint, it is believed that performance may be enhanced. For instance, it is often desirable for the firing bar to be rapidly accelerated during firing to ensure sufficient momentum for severing tissue effectively. Rigidly attached support plates may tend to dislodge in response, allowing the firing bar to blow out from the articulation joint. As a further example, it is desirable for the instrument to operate in the same manner whether articulated or not.

Increased friction when articulated would be inconvenient and distracting to the clinician if required to exert a varying amount of firing force.

Consequently, a significant need exists for an improved articulation mechanism for a surgical instrument mechanism that provides enhanced support to a firing bar through the articulation joint.

BRIEF SUMMARY OF THE INVENTION

It is accordingly an object of the invention to provide a surgical stapling and cutting device and method for using the device that overcome the hereinafore-mentioned disadvantages of the heretofore-known devices and methods of this general type and that provides an articulating surgical end effector With the foregoing and other objects in view, there is provided, in accordance with the invention, a medical device end effector connection assembly, including a passive articulation joint for connecting an end effector to a control handle.

With the objects of the invention in view, in a medical device having an end effector connected to a control handle, there is also provided an end effector connection assembly including a passive articulation joint connecting the end effector to the control handle.

With the objects of the invention in view, there is also provided a medical device, including a control handle and a surgical end effector connected to the control handle through a passive articulating connection.

With the objects of the invention in view, there is also provided a medical device, including a control handle and a surgical end effector passively articulated with respect to the control handle.

With the objects of the invention in view, there is also provided a medical device, including a control handle having a first portion of a passive articulation joint and a surgical end effector having a second portion of the passive articulation joint, the first and second portions of the passive articulation joint connecting the end effector to the control handle.

With the objects of the invention in view, there is also provided a medical device, including a control handle and a surgical end effector having a passive articulation joint connecting the end effector to the control handle.

With the objects of the invention in view, there is also provided a medical device, including a control handle, a surgical end effector, and a passive articulating joint connecting the end effector to the control handle.

With the objects of the invention in view, there is also provided a medical device, including a control handle having an articulation joint actuator with an unactuated state and an actuated state, a surgical end effector, and a passive articulating joint connecting the end effector to the control handle. The articulation joint actuator, when in the unactuated state, holds the passive articulation joint and, thereby, the end effector, in a substantially fixed articulation position, and, when in the actuated state, releases the passive articulation joint into a freely articulating state to permit free articulation of the end effector with respect to the control handle dependent upon external forces acting upon the end effector.

With the objects of the invention in view, there is also provided a medical device, including a surgical stapling end effector having at least one of a stapling device with staples and a cutting device with a blade, a control handle having a stapler closing actuator closing the stapling device when actuated a staple firing actuator at least one of stapling the staples and cutting tissue with the cutting device when actuated, and an articulation joint actuator having an unactuated state and an actuated state, and a passive articulating joint connecting the end effector to the control handle. The end effector freely articulates dependent upon forces acting upon the end effector when the articulation joint actuator is actuated and is locked in a given articulation position when the articulation joint actuator is unactuated.

As used in the art and as used herein, transverse movement of a medical end effector relative to an instrument shaft is conventionally referred to as "articulation." In prior art medical devices having articulation control, the articulation movement is directed actively from the device handle. This active control can be mechanical and/or electrical. For example, some prior art devices have levers at the top of the control handle and, when pivoted left the end effector articulates left and when pivoted right the end effector articulates right. Some operate with opposite movement. To effect this active articulation, it is very difficult for the operator to use only one hand. Thus, often, the operator must hold the handle with one hand and pivot the articulation lever with the other hand. As is known, the trend for laparoscopic and other similar medical devices is to make them operable with a single hand because surgeons often lose control of the device held in the second hand when it is necessary to remove their second hand from that device in order to operate the articulation lever. Loss of device control is undesirable and extends the surgical procedure if the device falls outside the view of the operating surgeon. One prior art device uses electrical measures to actively control articulation. In U.S. Pat. No. 7,213,736 to Wales et al., electrical power is supplied to an electrically actuated polymer to articulate the end effector actively in the desired direction. These prior art devices can be characterized by referring to them as "active articulation" devices, in which an articulation control device is present on the handle and extends through the articulation joint to force the articulation in either articulation direction. In other words, the forces required to perform articulation are generated internally in the device.

The articulation assembly of the present invention has no mechanical control device in the handle to effect direct control of articulating movement of the end effector. There is no articulation control device present on the handle that extends through the articulation joint to force the end effector to articulate in a direction. Instead, articulation of the end effector is dependent upon pressure between a surface of the environment in which the end effector exists and an exterior surface of the end effector, for example, at a location distal of the articulation joint. A torque to pivot the inventive end effector about the articulation axis arises from forces external to the device. One force is present by the user holding the handle. The other force acts distal of the articulation joint and is imparted by the environment in which the end effector is present and against which the end effector is being held. In other words, the forces required to perform articulation are external to the device. This motion can be and is referred to herein as "passive articulation" and the "articulation joint" of the present invention operates with passive articulation—it requires a torque external to the device to articulate the end effector about the axis of the passive articulation joint.

In one aspect of the invention, the surgical instrument has a handle portion that releases a lock to allow articulation of the end effector and firing while articulated. The release and firing mechanisms are transferred through a shaft to the articulation mechanism. The articulation mechanism responds to forces that the user imparts to the end effector and allows articulation of the end effector out of line with the longitudinal axis of the shaft. A firing mechanism responds to the firing motion and is coupled for movement through the articulation mechanism and the end effector. A firing support device allows the firing mechanism to support and keep in place the firing mechanism as articulation occurs.

In accordance with another feature of the invention, the control handle has an articulation joint actuator having an unactuated state and an actuated state, the end effector has an articulation lock with a locked articulation state and an unlocked articulation state, and the articulation joint actuator changes the articulation lock from the locked articulation state to the unlocked articulation state when changed from the unactuated state to the actuated state and changes the articulation lock from the unlocked articulation state to the locked articulation state when changed from the actuated state to the unactuated state.

In accordance with a further feature of the invention, the stapler closing actuator and the staple firing actuator are different from the articulation joint actuator.

In accordance with an added feature of the invention, there are provided at least one first flexible beam connecting the control handle to the staple firing actuator through the passive articulation joint and at least one second flexible beam longitudinally connecting the end effector to the control handle through the passive articulation joint. The first and second flexible beams flex in a corresponding way to an articulation of the passive articulation joint.

In accordance with an additional feature of the invention, the control handle has a first longitudinal axis, the end effector has a second longitudinal axis, and at least one of the control handle, the end effector, and the passive articulating joint has an alignment device. In an exemplary embodiment, the alignment device biases the end effector to substantially align the first and the longitudinal axes when the articulation joint actuator is actuated. The alignment device can be a center-biasing device. In such an embodiment, the center-biasing device is a set of spring-loaded plungers disposed on opposing sides of the first longitudinal axis and independently urging the end effector to align the second longitudinal axis with the first longitudinal axis.

Another advantage of the present invention is that the movable distal end effector is center-biased. This means that the distal end is, first, freed from a stable position and is, then, passively moved into its new position by pressing the end effector against a feature of the environment, such as surrounding tissue. When the actuator that frees the end effector from the stable position is released, the distal end effector returns to its center position under the urging of a center-biasing device, preferably, at least one biasing spring, in particular, two biasing springs imparting a biasing force in opposing and, therefore, centering directions. Alternatively, the center-biasing device can be a set of spring-loaded plungers disposed on either side of the end effector at the clevis to urge the end effector independently towards a center position.

In accordance with yet another feature of the invention, the articulation joint actuator has a pull-lock with distally directed teeth, the passive articulation joint has a gear with proximally directed teeth interlocked with the distally directed teeth when the articulation joint actuator is unactuated, and the articulation joint actuator disengages the distally directed teeth from the proximally directed teeth to articulating unlock the end effector when the articulation joint actuator is unactuated.

In accordance with yet a further feature of the invention, actuation of the distal movement occurs by a pull-to-release and a release-to-relock trigger. The trigger that controls the passive movement is normally locked. This lock is released by pulling in the trigger. Once the distal end effector is in a desired position, the user releases the trigger, thereby locking distal end effector in the new position.

The device according to the invention is a surgical stapler and cutter or other endoscopic device that can be used, in particular, to staple sections of tissue together and cut tissue when desired. In one embodiment of the end effector, measures for carrying out both the stapling and cutting functions can be entirely contained within the distal end effector of the device.

Again, another advantage of the present invention is that the handle is electronically controlled, universal, and motorized. The handle includes a microprocessor that is programmed for multiple product configurations. For example, in the case of a stapler, the handle is programmed for a 30 mm, a 45 mm, or a 60 mm staple cartridge. The distal shaft of the stapler has a proximal end that plugs into the universal handle. The distal shaft includes an array of electrical contacts that make corresponding contact with a mating array in the handle at the connection location. The contacts are unique for each of the different distal shafts and the handle "recognizes" the shaft and runs the appropriate program for it. The handle is programmed to include logic for safety lockouts, speed of stapler delivery, distance of stroke, and the like. Such modularity allows manufacture of one handle with multiple end effectors to mate thereto.

Actuation of the device is accomplished using an electric motor. The device may also be actuated by multiple electric motors, by hydraulics or pneumatics, or by the transmission of energy through a flexible drive shaft in any way such that the actuation assembly can be contained primarily or entirely in the distal portion of the device.

The work accomplished by any of these measures can be converted into desirable motions through any single or combination of screw drive, gear drive, wedge, toggle, cam, belt, pulley, cable, bearing, or the like push rod. In particular, a screw drive is used to transmit the work of the electric motor into linear motion. In one embodiment, the motor for the screw drive resides in the handle. A flexible rotating cable is connected from the motor to a threaded shaft. Thus, when the motor turns in either direction, the rotation of the flexible cable is transmitted to the threaded drive shaft and, because the stapling actuator and cutting slide is disposed on the drive shaft, both functions are carried out by distal movement of the slide. In a second embodiment, the motor resides entirely in the end effector and has a shaft connected to the slide drive shaft, either directly or through transmission gears. In such a case, all that is needed in the handle is the on/off and drive shaft direction actuators, the former for turning the motor on and off and the latter determining which direction the motor will spin.

The device has a carriage driven by the screw drive to accomplish multiple functions, including closing the stapler jaw, advancing the cutting blade, and firing the staples. The carriage is not the only way to accomplish these tasks. Secondary or multiple work sources may provide the work necessary to accomplish any of these functions.

In the second embodiment of the end effector, the entire stapling and cutting actuation device is self-contained and located distal of a movement joint.

The entire actuation device may be inserted and manipulated by a multi-axis "ball" or "universal" joint that will allow any movement and constraint as desired by the operator. Additionally the entire actuation device may be freed completely from the handle and re-grasped from a different angle to allow greater positional flexibility.

In accordance with yet an added feature of the invention, the passive articulation joint is a ball joint having a ball, a cupping device, and a ball-cup locking device for locking and unlocking the ball and the cupping device with respect to one another, the ball-cup locking device being in a locked state when the control handle is in an unactuated state and in an unlocked state when the control handle is in an actuated state. The end effector has one of the ball and the cupping device and the control handle has the other one of the ball and the cupping device. The ball is removably connected to the cupping device.

In accordance with yet an additional feature of the invention, the end effector has two longitudinal ends and the ball is two balls. Each of the two balls is disposed on one of the two longitudinal ends and the two balls are each removably connectable to the cupping device.

In one aspect of the invention, the instrument actuates an end effector with a longitudinally translating firing mechanism that is supported advantageously through an articulation mechanism by either flanking support plates or a rigid support channel. In the former embodiment, to better respond to firing loads on the firing mechanism, one or more ends of each support plate are resiliently or springedly engaged to one side of the articulation mechanism, and thus are better able to avoid buckling of the firing mechanism. For example, the pair of support plates flank the firing mechanism across the articulation mechanism, each support plate including an end springedly engaged to a frame recess formed in the articulation mechanism to assist in preventing buckling of the firing mechanism within or out of the articulation mechanism.

In the channel embodiment, the channel floats in the articulation mechanism and has surfaces that support either side of the firing mechanism as articulation occurs in either direction and, thus, avoid buckling of the firing mechanism. The channel has a floor and two sides. The support channel rests freely in a cavity inside the articulation mechanism. Ends of the channel are curved to match curves of the cavity. The support channel has various internal surfaces to contact and support the firing mechanism as it is bent within the articulation mechanism and, thereby, assists in preventing buckling of the firing mechanism within or out of the articulation mechanism.

Thus, various types of actuated diagnostic or therapeutic end effectors may be incorporated into the articulating surgical instrument of the present invention without buckling at the articulation mechanism, even with high firing forces and reduces component dimensions for endoscopic use.

In still a further aspect of the invention, a surgical instrument has a handle portion that produces a closing motion, a firing motion, an articulation mechanism unlocking motion, and an articulation motion, each transferred through a shaft. The end effector includes an elongate channel coupled to the shaft for receiving staples or a staple cartridge therein and an anvil that is pivotally coupled to the elongate channel and that is responsive to the closing motion from the shaft. A firing device has a distally presented cutting edge longitudinally received between the elongate channel and the anvil. The firing device is connected from the handle to the end effector through the shaft and the articulation mechanism. The firing device employs the stapling and carries out a cutting with the firing motion. The articulation mechanism allows movement of the end effector with respect to the shaft. The articulation mechanism is distally coupled to the shaft and permits articulation of the end effector after an articulation lock is removed (i.e., unlocked) and in response to forces that act upon the end effector to cause articulation motion thereof. In other words, when the articulation lock is unlocked, pressure of the end effector against the environment will cause articulation of the end effector with respect to the shaft. To support the firing mechanism, a pair of support plates can flank the firing mechanism across the articulation mechanism, each support plate including an end springedly engaged to a frame recess formed in the articulation mechanism, or a rigid channel can surround the firing mechanism across the articulation mechanism. Thereby, an improved stapling and severing instrument may incorporate a firing device that withstands high firing loads yet does not introduce significantly increased firing forces when articulated.

The actuation device may be manufactured in different lengths and/or manufactured in diameters appropriate for either laparoscopic or endoscopic use, or both. A replaceable staple cartridge can be used. Also, the actuation device can be constructed to attach to a distal end of a flexible endoscope.

A significant advantage of the present invention is that the movement of the end effector is passive and lockable. In other words, the end effector can be unlocked, subsequently moved into a desired position, and, then, caused be retained in the new position—all with a one-handed operation. Endoscopic and laparoscopic surgery requires that the physician be able to use both hands independently. Elimination of this requirement makes such surgeries extremely difficult or not possible. The handle of the present invention has a movement release/lock that can be actuated without the use of a second other hand, enabling a true one-handed operation of the device.

A further advantage of the present invention is that the axial movement of the end effector is discrete and manual. For example, the user can set the axial movement by rotating the distal end effector about the longitudinal axis of the device prior to insertion. This pre-set positioning occurs by pulling the end effector away from the shaft and, then, twisting the distal end effector in the desired direction. This axial movement, in combination with the off-axis movement (side to side) creates a compound angle at the distal end to aid in accurate positioning of the end effector (or even a plurality of end effectors). In another variant, the user can dynamically rotate the distal end effector about the longitudinal axis of the device at any time by providing a rotation device that axially fixedly but rotationally freely connects the handle to the distal components including the shaft, the articulation mechanism, and the end effector. Rotation of the distal components occurs by pulling the bell-shaped rotation device in a direction away from the end effector and, then, rotating the rotation device about the longitudinal axis of the shaft in the desired direction. This rotating movement, in combination with the off-axis movement of the end effector creates a compound angle at the distal end of the device to aid in accurate positioning of the end effector (or even a plurality of end effectors).

Still another advantage of the present invention is that the stapler/cutter can be configured to mount to an end of a standard, flexible endoscope. The controls are back fed through the working channel of the endoscope and mated to the control handle or a control module.

With the objects of the invention in view, there is also provided a method for operating an end effector of a medical device, including the steps of retaining a passive articulation joint controlling articulation movement of an end effector in a stable position with an articulation lock and actuating a release of the articulation lock to unlock the passive articulation joint and permit articulating motion of the end effector through the passive articulation joint dependent upon external forces acting upon the end effector.

With the objects of the invention in view, there is also provided a method for operating an end effector of a medical device, including the steps of retaining a passive articulation joint in a locked state with an articulation lock and actuating the articulation lock to unlock the passive articulation joint and permit articulating motion of the passive articulation joint dependent upon external forces acting upon the end effector.

In accordance with another mode of the invention, the end effector is passively moved into an articulated position.

In accordance with a further mode of the invention, the end effector is passively moved into an articulated position by pressing a portion of the end effector against a feature of the environment.

In accordance with an added mode of the invention, a force is applied to the end effector to articulate the end effector into a desired articulated position.

In accordance with an additional mode of the invention, actuation of the articulation lock is removed to lock the passive articulation joint and, thereby, prevent further articulating motion of the end effector.

Advantageously, all of the above steps are performed with one-hand.

Other features that are considered as characteristic for the invention are set forth in the appended claims.

Although the invention is illustrated and described herein as embodied in a surgical stapling and cutting device and method for using the device, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

Advantages of embodiments the present invention will be apparent from the following detailed description of the preferred embodiments thereof, which description should be considered in conjunction with the accompanying drawings in which:

FIG. 20 is an illustration of a left side from above the surgical stapler of FIG. 18 with the lateral movement trigger depressed, with the distal end effector in a laterally free movement state position-dependent upon contact with the environment, such as a surface, and with the jaws of the end effector open in the at-rest position of the actuator handle and laterally positioned at an approximately 45 degree angle;

FIG. 21 is an illustration of a left side from above the surgical stapler of FIG. 18 with the lateral movement trigger in an at-rest state, with the distal end effector in a laterally captured movement state, and with the jaws of the end effector open in the at-rest position of the actuator handle and laterally positioned at an approximately 30 degree angle;

DETAILED DESCRIPTION OF THE PREFERRED EMBODIMENTS

Figure 1:
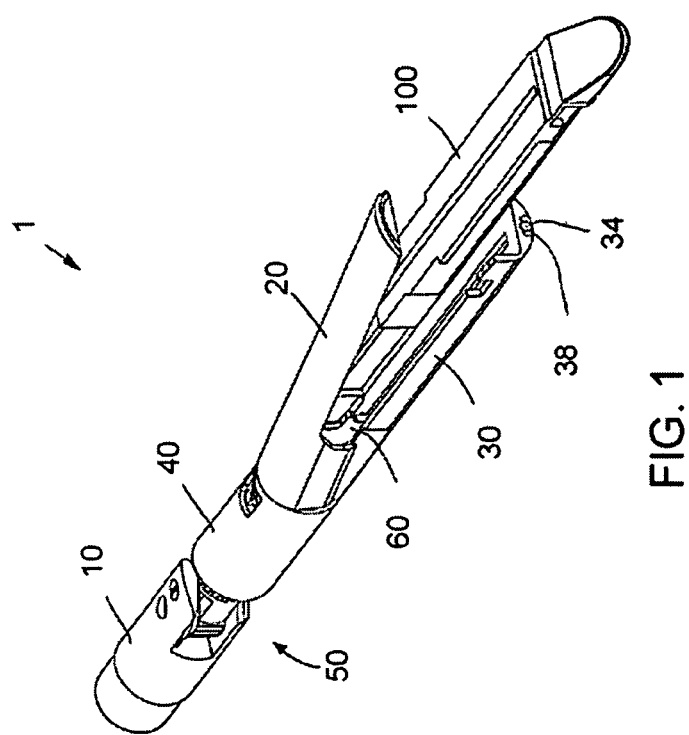
FIG. 1 is an enlarged, fragmentary, perspective view of a first embodiment of a distal stapling and cutting end effector and a portion of a shaft connected thereto according to the invention viewed from a distal end thereof with a staple cartridge approximately pulled out half-way from a staple cartridge jaw of the end effector and with an anvil of the stapler separated from a staple-actuating and tissue-cutting slide.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Referring now to the figures of the drawings in detail and first, particularly to FIG. 1 thereof, there is shown a first exemplary embodiment of a stapling and cutting end effector 1 according to the present invention. The major parts of the end effector 1 include a clevis 10, an anvil 20, a cartridge holder 30 for receiving a staple cartridge 100, an adapter sleeve 40, and a lateral translation or articulation device 50. FIG. 1 illustrates the removability of the staple cartridge 100 from the cartridge holder 30.

Connecting the anvil 20 to the cartridge holder 30 and the staple cartridge 100 is a staple-actuating and tissue-cutting slide 60. This slide 60 operative engages both the anvil 20 and the cartridge holder 30 to keep the two parts 20, 30 in proper alignment so that the actuated staples inside the cartridge 100 hit their respective stapler anvils within the anvil 20 and secure the staples around tissue disposed between the anvil 20 and the cartridge 100. The distal facing surface of the slide 60 contains a blade 62 for cutting the tissue disposed in the jaws 20, 30 as the tissue is being stapled together. Proximal movement of the slide is shown, diagrammatically, in FIGS. 1 to 3. So that the slide 60 can be seen in FIGS. 1 and 3, the anvil 20 is uncoupled from the top end of the slide 60. In operation, however, the slide 60 must be coupled to the anvil 20 as shown in FIG. 2 and, especially, in FIG. 13.

Figure 2:
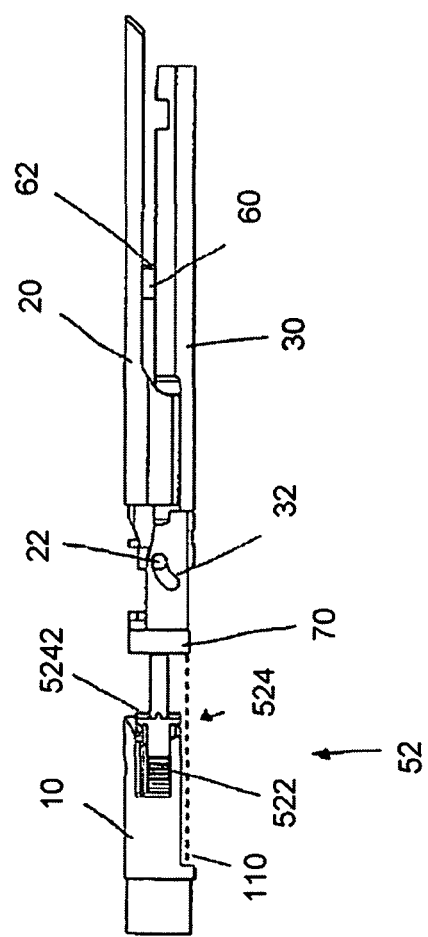
FIG. 2 is an enlarged, fragmentary, side elevational view of the end effector of FIG. 1 with the distal cowling, the proximal castellation axial movement part, and the cartridge removed for clarity, and with the anvil of the stapler connected to the slide.

FIG. 2 illustrates the end effector 1 with the adapter sleeve 40 removed to make visible various features of the translation therein.

Figure 3:
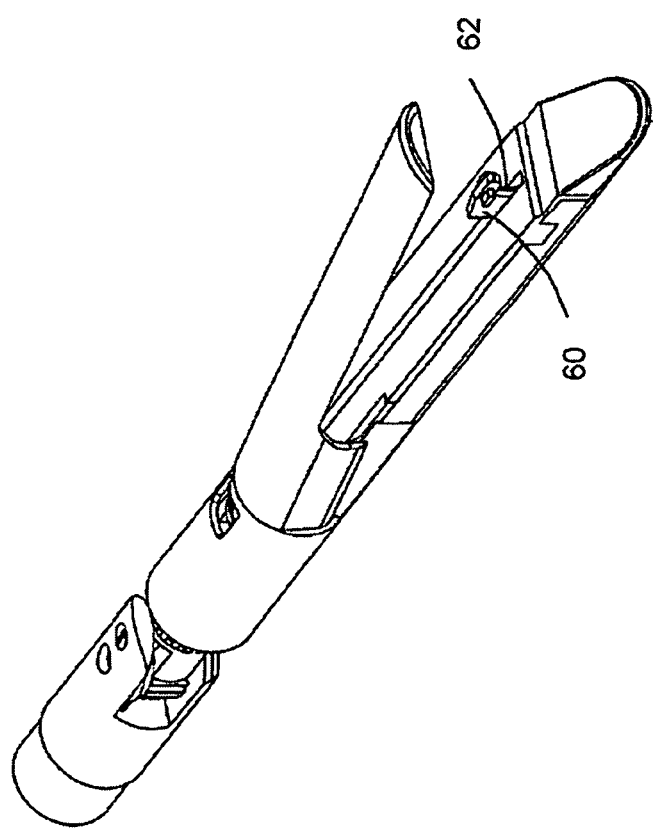
FIG. 3 is an enlarged, fragmentary, perspective view of the end effector of FIG. 1 with the staple-actuating and tissue-cutting slide in a distal position but with the anvil of the stapler separated from the slide.

A first of two primary parts of the lateral translation device 50 are apparent in FIGS. 1 to 3. A proximal part 52 includes a proximal sprocket 522, an intermediate castellated connector 524, and a distal rod 526. In the exemplary embodiment, the intermediate castellated connector 524 has four distally projecting teeth 5242, clearly shown in FIG. 2.

Also visible in FIG. 2 is a pull cable adapter 70. The pull cable adapter 70 is connected to a pull cable 110 (dashed lines) at a proximal side and to the cartridge holder 30 at a distal side thereof. The pull cable adapter 70, therefore, is used to pull or push the cartridge holder 30 with respect to the anvil 20 and, thereby, pivot the anvil 20 from an open position to a closed position, or vice-versa, dependent upon movement of the cartridge holder 30. The proximal end of the anvil 20 has a cam follower 22 on either side thereof. The proximal end of the cartridge holder 30 defines two cam surfaces 32 on either side thereof and aligned to receive a respective one of the cam followers 22. Accordingly, movement of the cartridge holder in a distal or proximal direction results in a corresponding opening or closing pivoting movement of the anvil 20.

Figure 4:
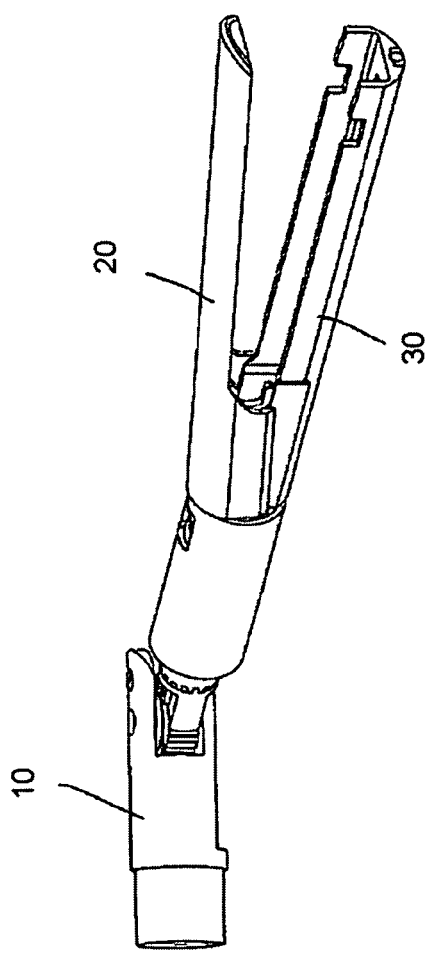
FIG. 4 is an enlarged, fragmentary, perspective view of the end effector of FIG. 1 with the staple cartridge removed from the lower jaw/staple cartridge holder and with the clevis rotated in an approximately 45 degree angle with respect to center.

FIG. 4 shows the lateral articulating movement of the stapler 20, 30 with respect to the clevis 10.

Figure 5:
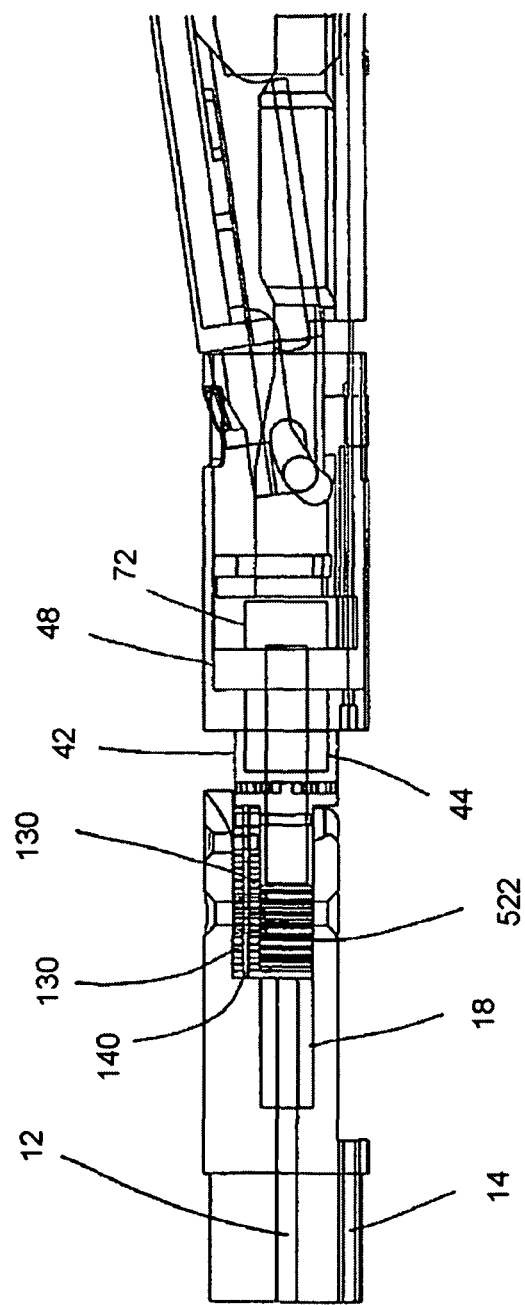
FIG. 5 is an enlarged, fragmentary, wireframe side elevational view of a distal portion of the end effector of FIG. 1.
Figure 6:
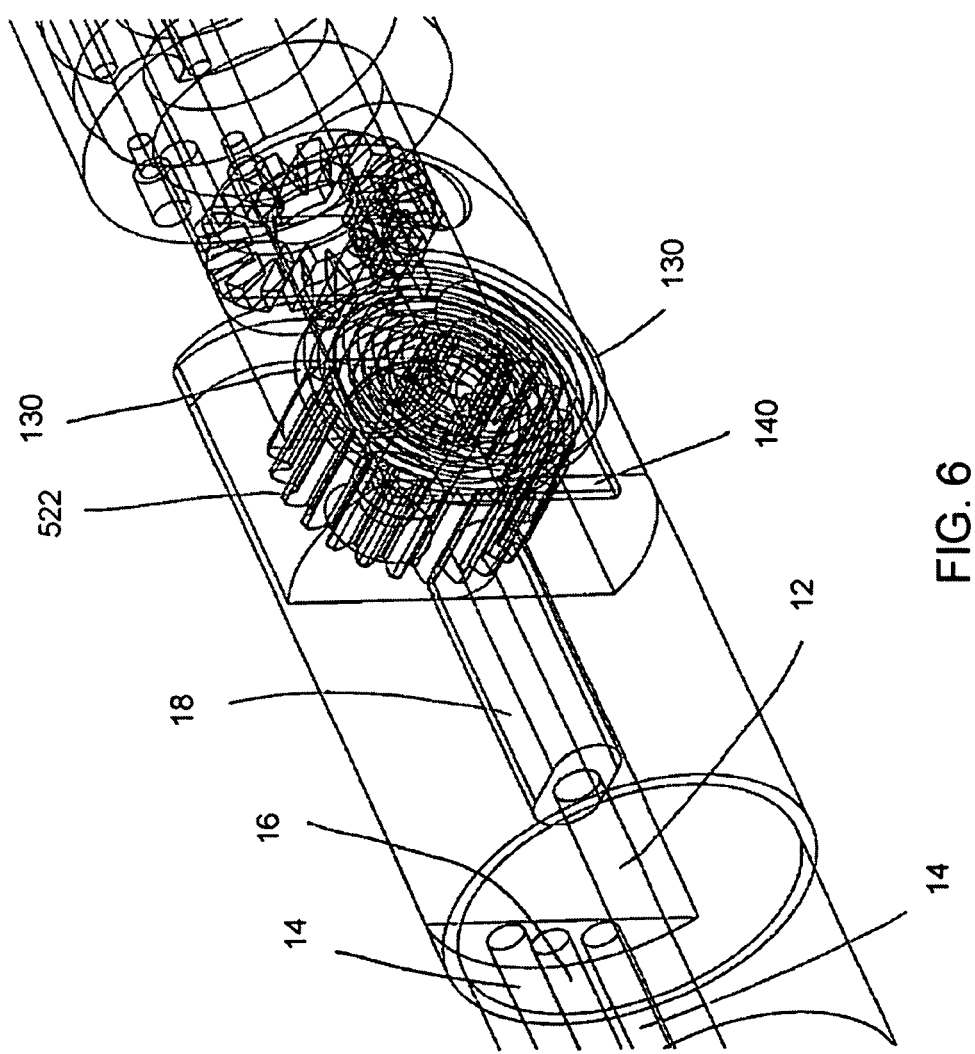
FIG. 6 is an enlarged, fragmentary, wireframe perspective view of a castellation axial movement assembly of the end effector of FIG. 1 rotated approximately 90 degrees and with an end effector lateral movement locking pin and a proximal screw removed for clarity.
Figure 7:
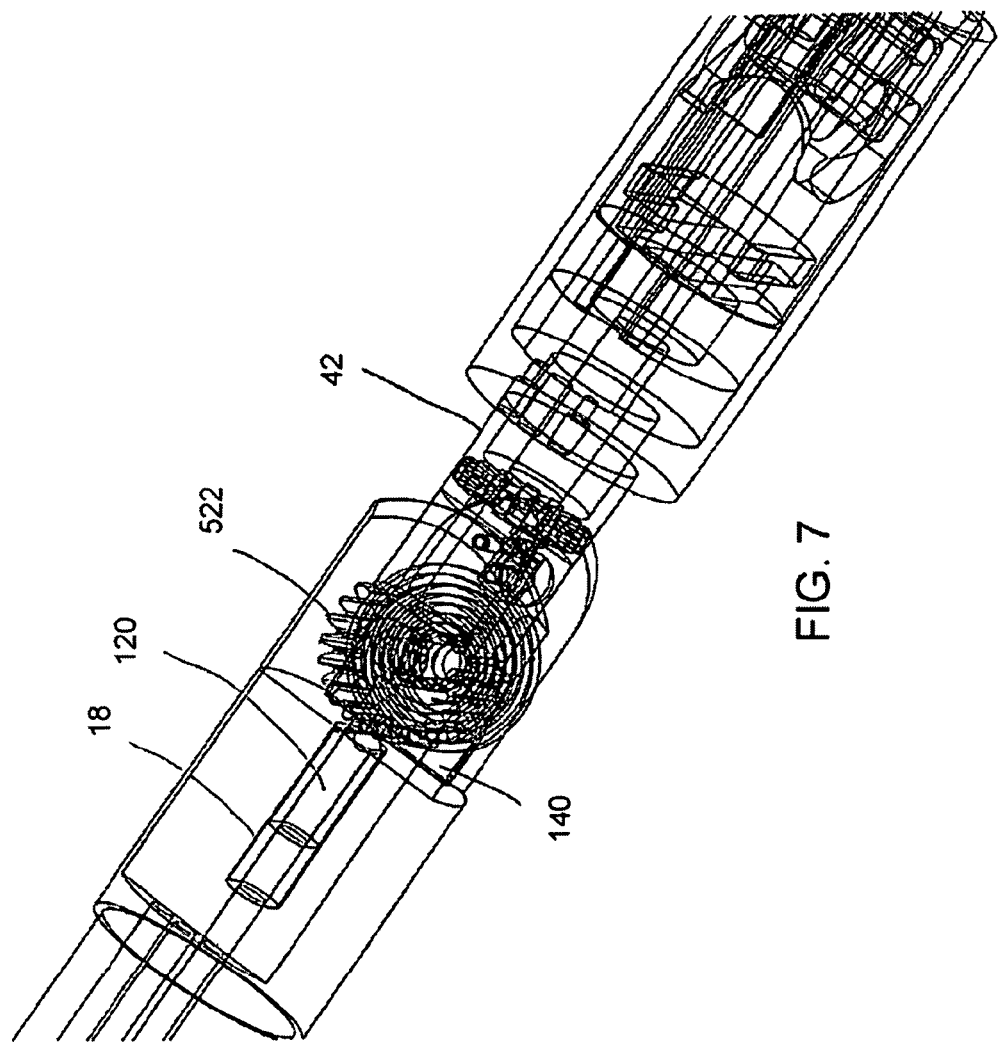
FIG. 7 is an enlarged, fragmentary, wireframe perspective view of the end effector of FIG. 6 viewed from a bottom thereof with an end effector lateral movement locking pin engaging a tooth of the lateral movement sprocket, and with springs and the proximal screw removed for clarity.
Figure 8:
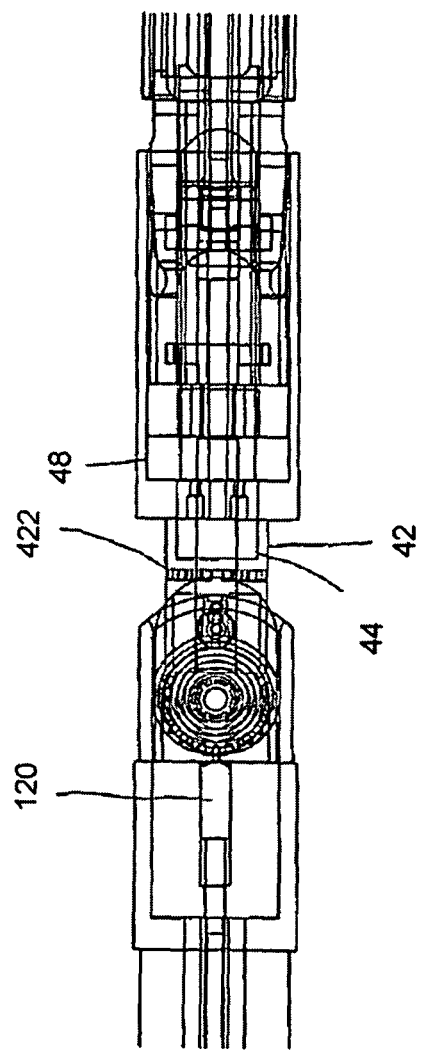
FIG. 8 is an enlarged, fragmentary, wireframe bottom plan view of the end effector of FIG. 7 with an end effector lateral movement locking pin engaging a tooth of the lateral movement sprocket.
Figure 9:
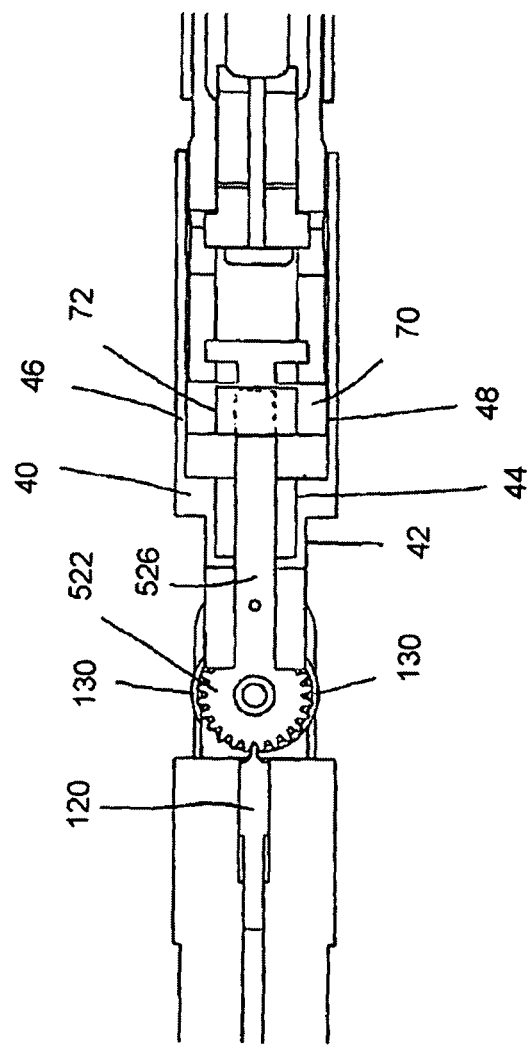
FIG. 9 is an enlarged, fragmentary, longitudinal cross-sectional view of the end effector of FIG. 8 viewed from a bottom thereof with the end effector lateral movement locking pin engaging a tooth of the lateral movement sprocket and with the springs removed for clarity.

In FIGS. 5 to 8, all parts, including the adapter sleeve 40 and the clevis 10 are shown in wire frame, thereby, revealing features therein. The clevis 10 contains four lumens, two of which are shown in FIG. 5 and all four are shown in FIGS. 6 and 7. A first 12 of the lumens is formed to contain a non-illustrated shaft for controlling distal and proximal movement of an end effector lateral movement locking pin 120, which pin 120 is first shown in FIGS. 8 and 9. The two lateral lumens 14 are shaped to receive the pull-wire that moves the pull cable adapter 70 proximally (distal movement of the pull cable adapter 70 is caused by a spring). The other of the two lumens 14 is extra and can receive any number of possible additional instrumentation. The drive cable lumen 16 is the last of the four lumens and is shaped to receive the flexible drive cable that turns the drive screw 34 (see FIG. 1), which controls movement of the slide 60.

At the distal end of the drive cable lumen 16, the clevis 20 defines an oblong cavity 18 for receiving therein the lateral movement locking pin 120. FIGS. 6 to 9, in particular, show an exemplary shape of this cavity 18. Because the lateral movement locking pin 120 is oblong in circumferential shape, the pin 120 does not rotate away from an aligned position with the teeth of the sprocket 522.

Figure 10:
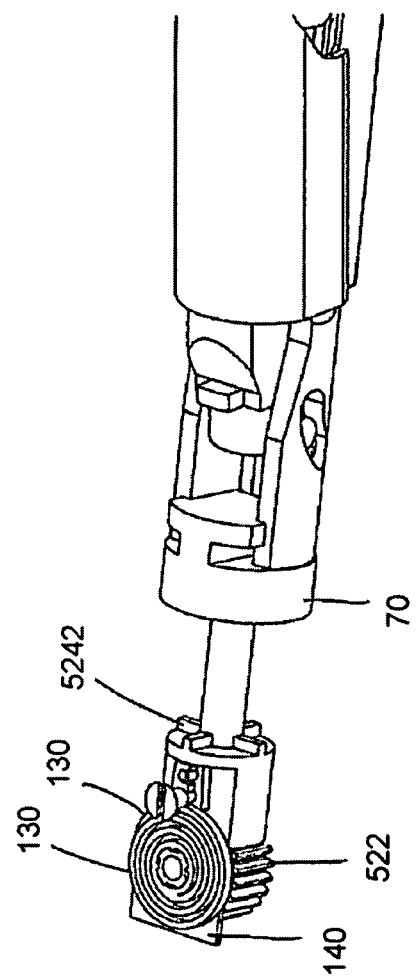
FIG. 10 is an enlarged, fragmentary, perspective view of the end effector of FIG. 2 rotated about the longitudinal axis with the clevis, the screw, and the distal castellation sleeve axial movement and spring parts removed for clarity.

Also visible under the top side of the clevis 10 in FIG. 5 are two centering springs 130. These springs 130 are also shown in FIGS. 6 to 9 and, in particular, FIG. 10. To prevent undesired interaction between the springs 130, a dividing plate 140 is sandwiched between the springs 130. FIG. 10 illustrates the two springs 130 with the dividing plate 140 therebetween.

The features underneath the transparent sleeve 40 are better explained with respect to FIGS. 7 to 10. The sleeve 40 defines two exterior structures and two internal bores. The first exterior structure is a proximal cylinder 42. The proximal cylinder 42 defines castellations 422 at a proximal end thereof. These castellations 422 match and interact with the intermediate castellated connector 524 of the proximal part 52. The proximal cylinder 42 also defines a first bore 44 that is shaped to receive the distal rod 526 of the proximal part 52. There is a cylindrical, tubular radial clearance between the rod 526 and the interior surface of the first bore 44 and a longitudinal clearance between the proximal end of the cable adapter 70 and the proximal inside surface of the first bore 44. This tubular-shaped clearance can receive a first tubular biasing device (e.g., a coil spring), which is not illustrated for clarity. The first biasing device is positioned to apply a proximally directed force on the proximal-most end of the adapter sleeve 40. In such a configuration, the force applied by the first biasing device presses the distal castellations 422 towards and against the proximal castellations 5242.

The second exterior structure of the sleeve 40 is a distal cylinder 46. The distal cylinder 46 defines a second bore 48 that is shaped to receive therein the pull cable adapter 70. The pull cable adapter 70 also defines an interior bore 72 that is shaped to receive the distal rod 526 of the proximal part 52. For clarity in the figures, the rod 526 is shown extending entirely into the interior bore 72 only by the dashed lines in FIG. 9. In operation, the rod 526 extends entirely into the interior bore 72. The interior bore 72 is coaxial and, in an exemplary embodiment, has the same interior diameter of the first bore 44. Accordingly, there exists a cylindrical, tubular radial clearance between the rod 526 and the interior surface of the interior bore 72 and a longitudinal clearance between the distal surface of the cable adapter 70 and the inside distal surface of the interior bore 72. This is because it is also shaped to house a second tubular biasing device (e.g., a coiled spring), also not illustrated for clarity. The second biasing device is provided to impart a distally directed biasing force against the pull cable adapter 70. Such a force keeps the jaws 20, 30 in an open position. Accordingly, the jaws 20, 30 have an at-rest open position.

Without providing an intermediate part, the two non-illustrated biasing devices connect and, therefore, form a single spring. However, it is desirable to not have the two biasing devices interact because separation of the castellated parts causes an unwanted force to be applied to the cartridge holder 30 and movement of the cartridge holder 30 may loosen the connection of the castellated parts. Accordingly, a non-illustrated washer is disposed between the two biasing devices in the cylindrical cavity 74 defined by the proximal end surface of the pull cable adapter 70 and the distal end surface of the second bore 48. FIG. 7 particularly illustrates the proximal side for holding this washer, which is shaped to only receive the distal rod 526 therethrough. Accordingly, because the washer is trapped between the pull cable adapter 70 and the sleeve 40, the two springs are decoupled and provide their respective biasing forces independent of one another.

Figure 11:
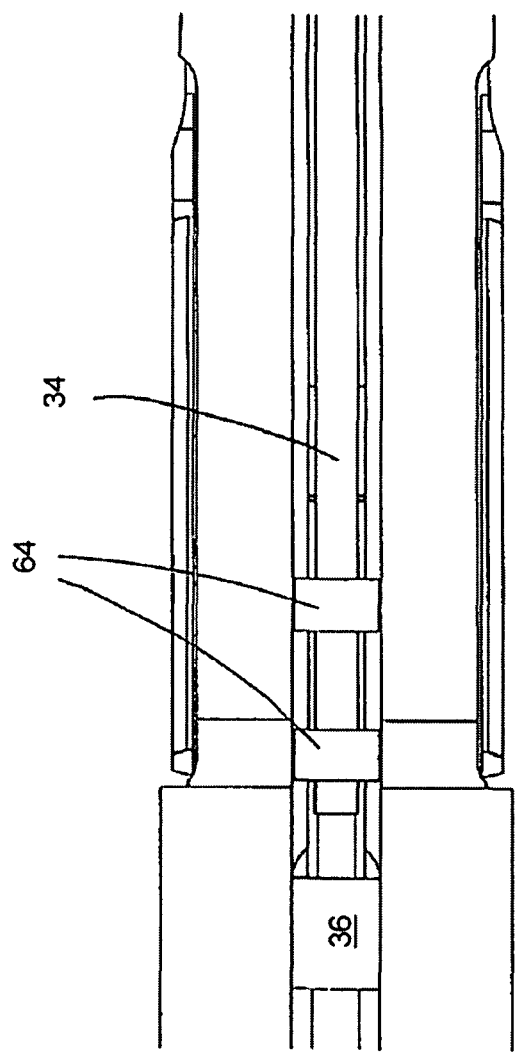
FIG. 11 is an enlarged, fragmentary, bottom plan view of a distal portion of the end effector of FIG. 1 with the staple-actuating and tissue-cutting slide in a proximal position.
Figure 12:
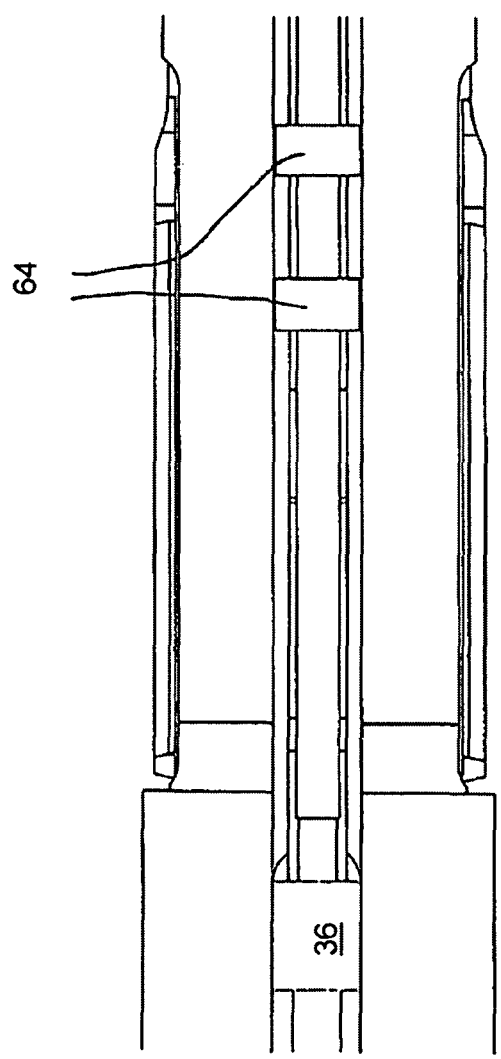
FIG. 12 is an enlarged, fragmentary, bottom plan view of the distal portion of the end effector of FIG. 11 with the staple-actuating and tissue-cutting slide in an intermediate position.
Figure 13:
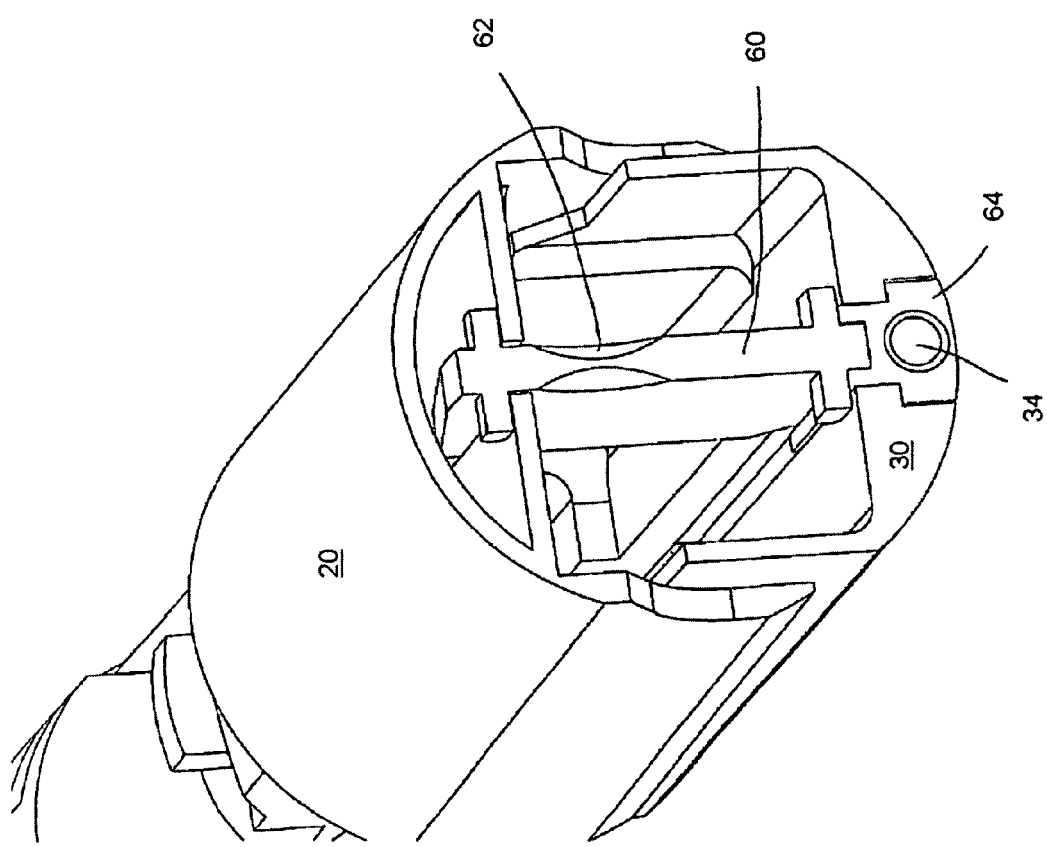
FIG. 13 is an enlarged, fragmentary, radially cross-sectional view through the stapling actuating and tissue-cutting slide of the end effector of FIG. 2.

The underside view of FIGS. 11 and 12 illustrate the drive shaft 34 of the slide 60 and the proximal idler bushing 36 that holds the drive shaft 34 in place within the cartridge holder 30. At the position of the idler bushing 36, the drive shaft 34 does not have threads. However, distal to the idler bushing 36, the drive shaft 34 has threads (which are not illustrated) extending towards the distal end of the drive shaft 34. FIGS. 11 and 12 do not show the thrust bearing 38 on the opposite end of the drive shaft 34, but FIG. 1 clearly illustrates this bearing 38. Also illustrated in FIGS. 11, 12, and 13 is the bottom of the slide 60 in the form of a drive nut 64. In an exemplary embodiment, this drive nut 64 is a part that is separate from the blade 62 of the slide 60 but is fixedly connected at the bottom of the blade 62. The illustrated shape of the drive nut 64 has a dumbbell-shaped cross-section to relieve some of the forces exerted upon the threads. In FIG. 11, the drive nut 64 is in a proximal position where the anvil 20 is in an opened position. FIGS. 12 and 13, in contrast, show the drive nut 64 in intermediate positions where the anvil 20 is in a partially closed position.

FIG. 13 is especially useful in illustrating the shape and configuration of the slide 60, including the blade 62 and the drive nut 64.

Figure 14:
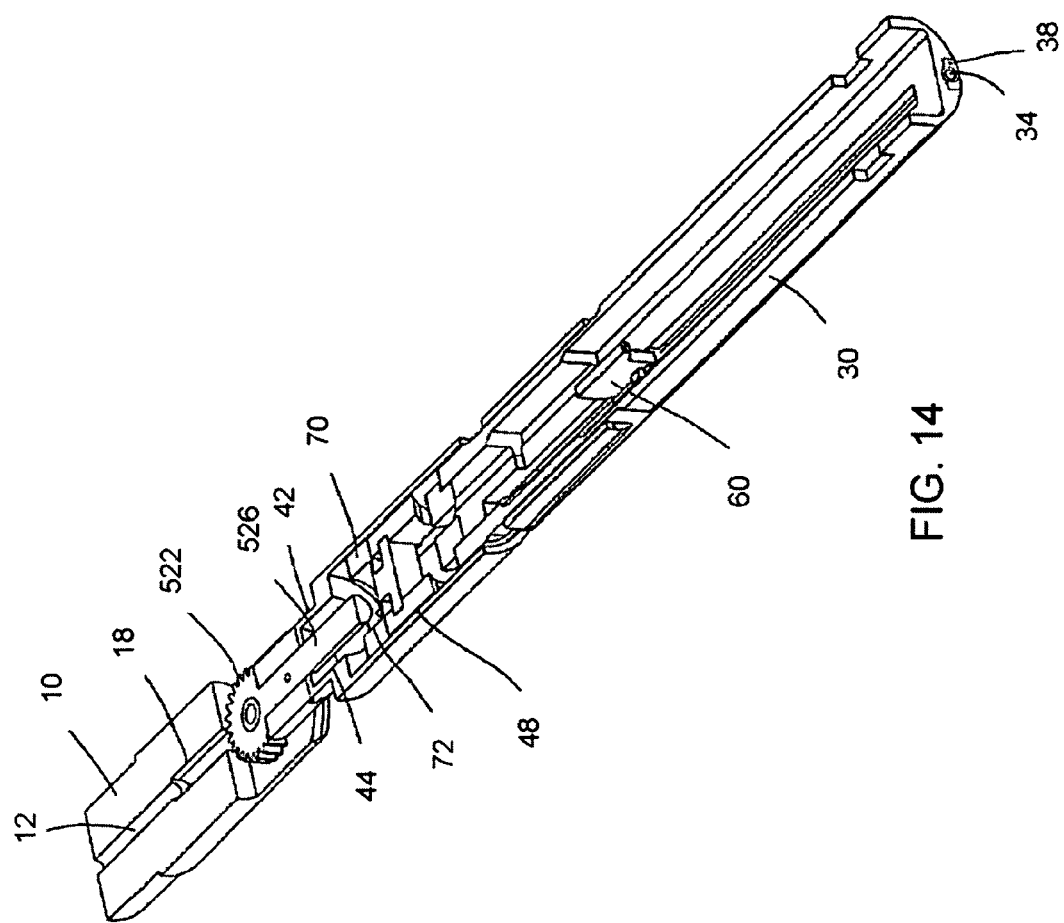
FIG. 14 is an enlarged, fragmentary, horizontal longitudinal cross-sectional view through a lower half of the end effector of FIG. 1.
Figure 15:
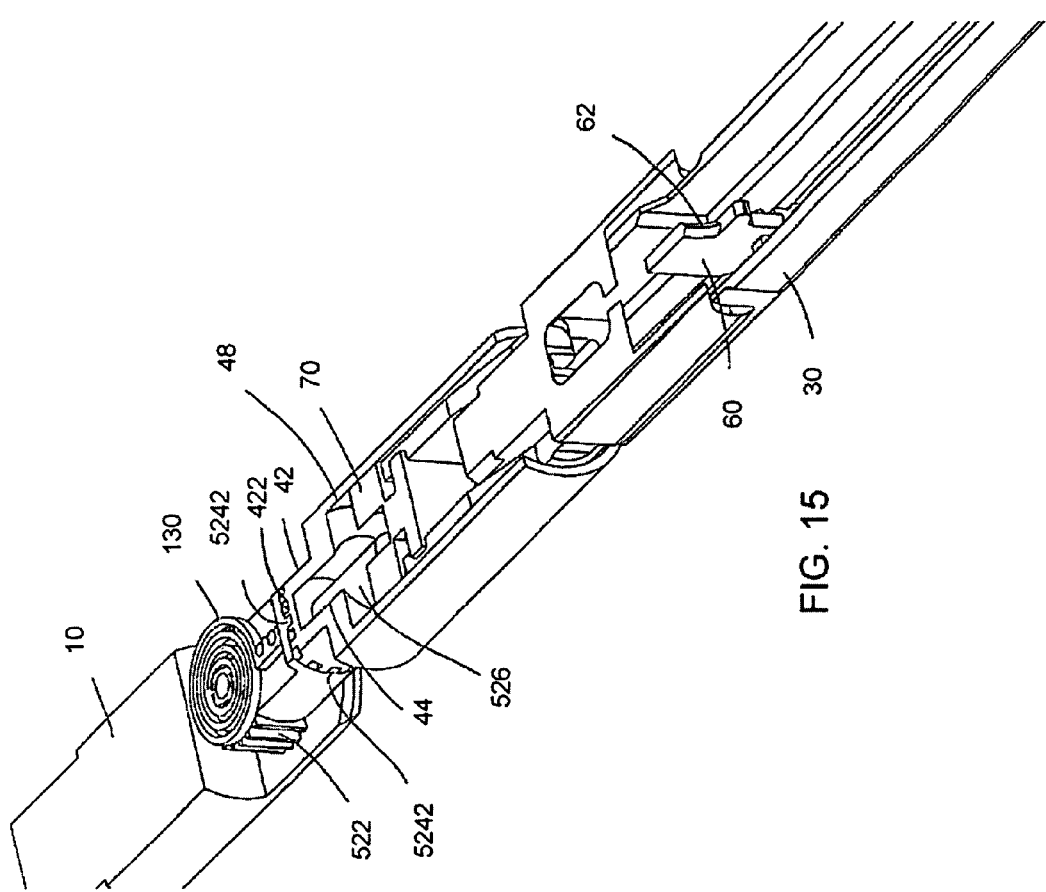
FIG. 15 is an enlarged, fragmentary, horizontal longitudinal cross-sectional view through an upper half of a proximal portion of the end effector of FIG. 1.

The horizontal cross-section along approximately the longitudinal axis of the end effector in FIGS. 14 and 15 is particularly useful in viewing the bores around the distal rod 526. Again, for clarity, the rod 526 is not shown extending all the way to the distal surface of the bore 72 in the pull cable adapter 70 even though it does extend all the way to this surface. Around the proximal end of the rod 526 is the first bore 44 in the adapter sleeve 46. Just distal of the first bore 44 is the cavity 74 for receiving the washer therein and, just distal of the cavity 74, is the interior bore 72 of the pull cable adapter 70 for receiving the second biasing device.

Figure 16:
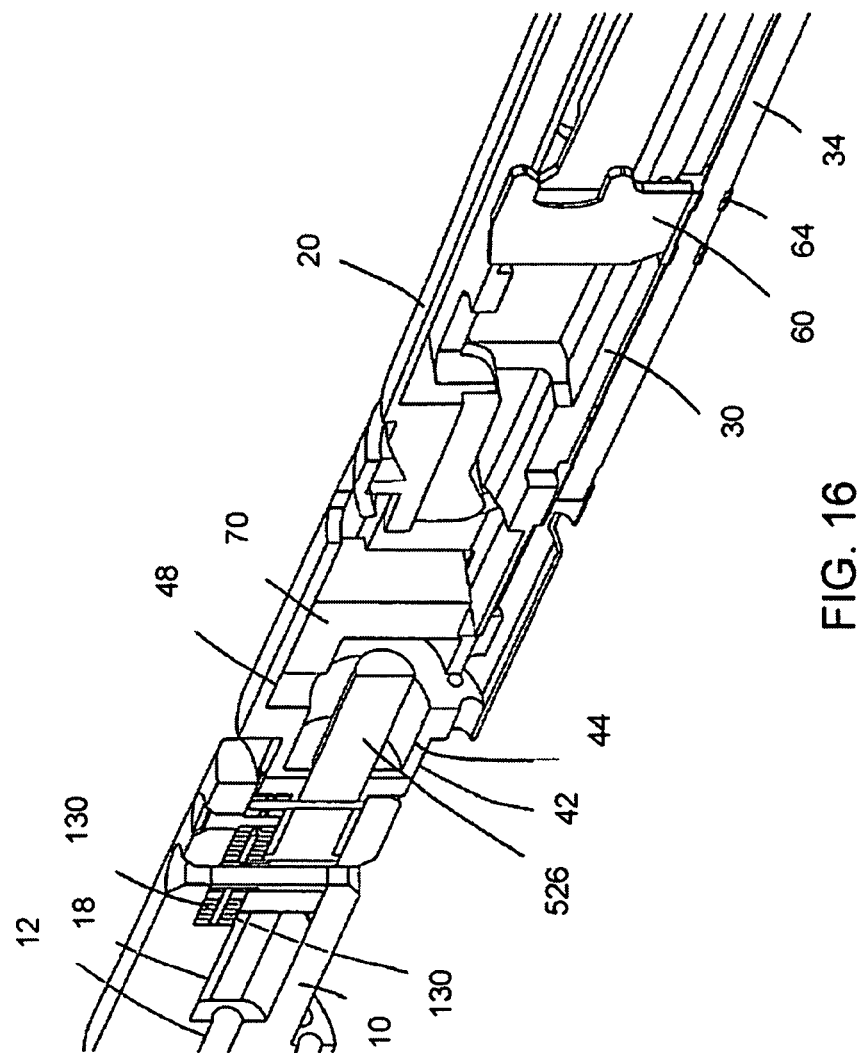
FIG. 16 is an enlarged, fragmentary, vertical longitudinal cross-sectional view approximately through a longitudinal axis of a proximal portion of the end effector of FIG. 1.

The vertical cross-section along approximately the longitudinal axis of the end effector in FIG. 16 is particularly useful in viewing the connection between the drive nut 64 and the drive shaft 34. Again, for clarity, the rod 526 is not shown extending all the way to the proximal surface of the bore 72 in the pull cable adapter 70.

Figure 17:
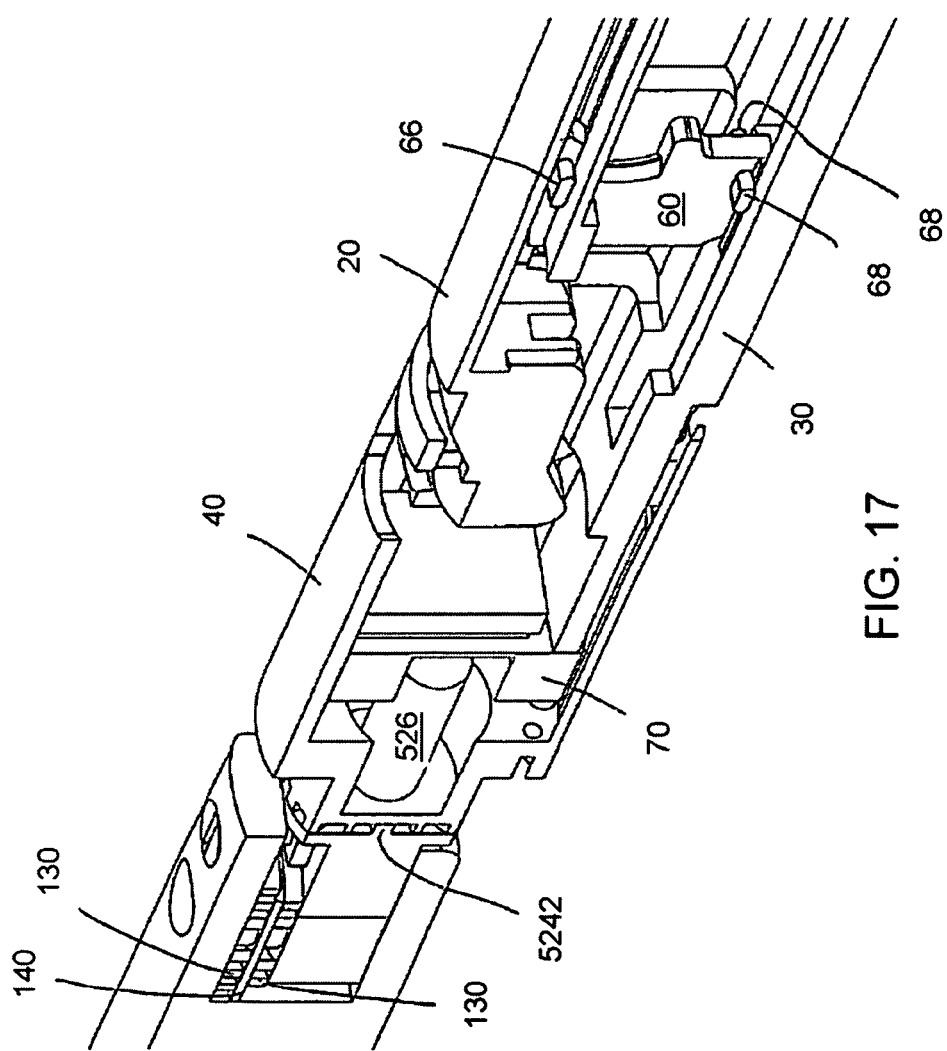
FIG. 17 is an enlarged, fragmentary, vertical longitudinal cross-sectional view through a right half of the proximal portion of the end effector of FIG. 1.
Figure 18:
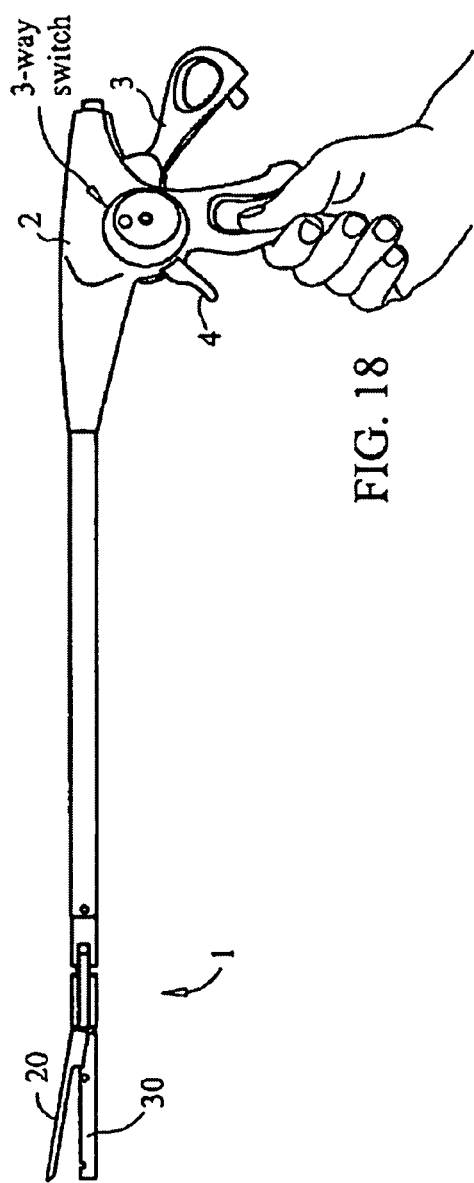
FIG. 18 is an illustration of a left side of the surgical stapler according to the invention with the jaws of the end effector open in an at-rest position of an actuator handle.
Figure 19:
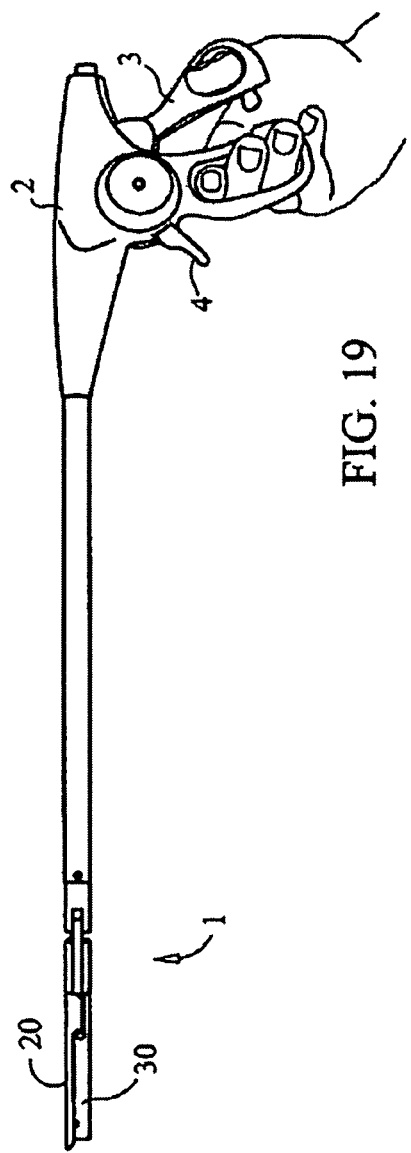
FIG. 19 is an illustration of a left side of the surgical stapler of FIG. 18 with the jaws of the end effector closed in an actuated position of a thumb trigger of the actuator handle.

The vertical cross-section along approximately the longitudinal axis of the end effector in FIG. 17 is particularly useful in viewing the connection between the slide 60 and both the anvil 20 and the cartridge holder 30. Two upper wings 66 are disposed in a groove inside the anvil 20 and two lower wings 68 form an upper holding surface of the I-shape formed by the lower wings 68 and the drive nut 64.

Figure 60:
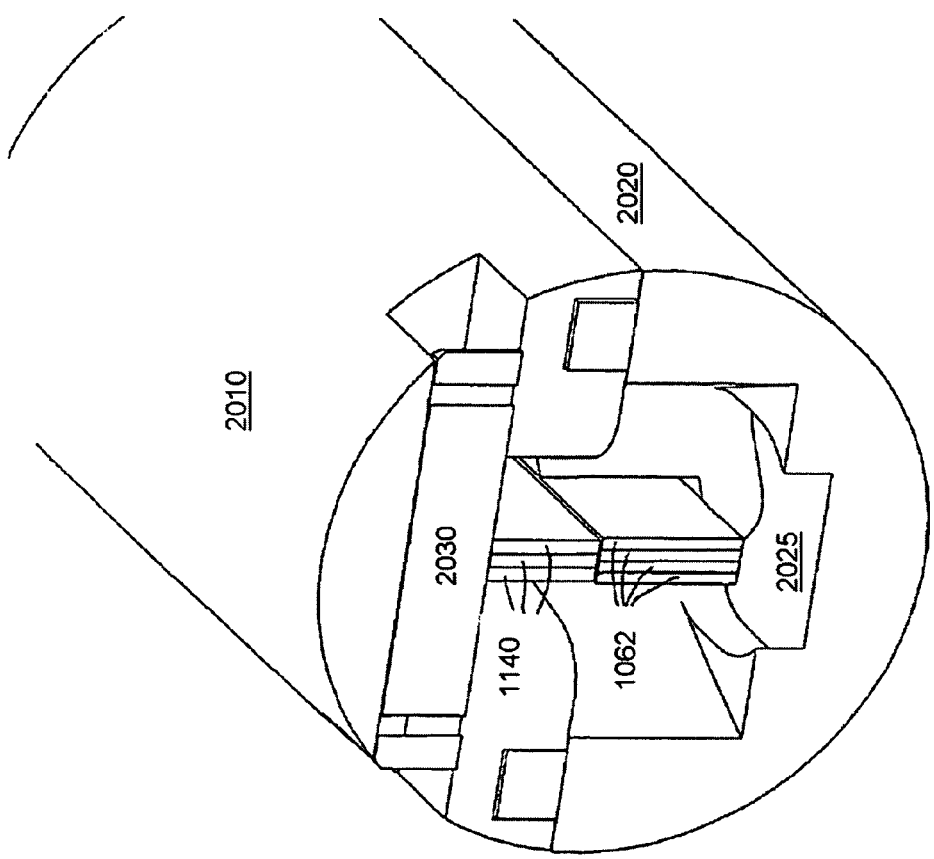
FIG. 60 is a fragmentary, vertically transverse, cross-sectional view of the articulating portion of the end effector of FIG. 54 through a proximal end of a dogbone guide chamber of the lower clevis with the dogbone guide removed.
Figure 61:
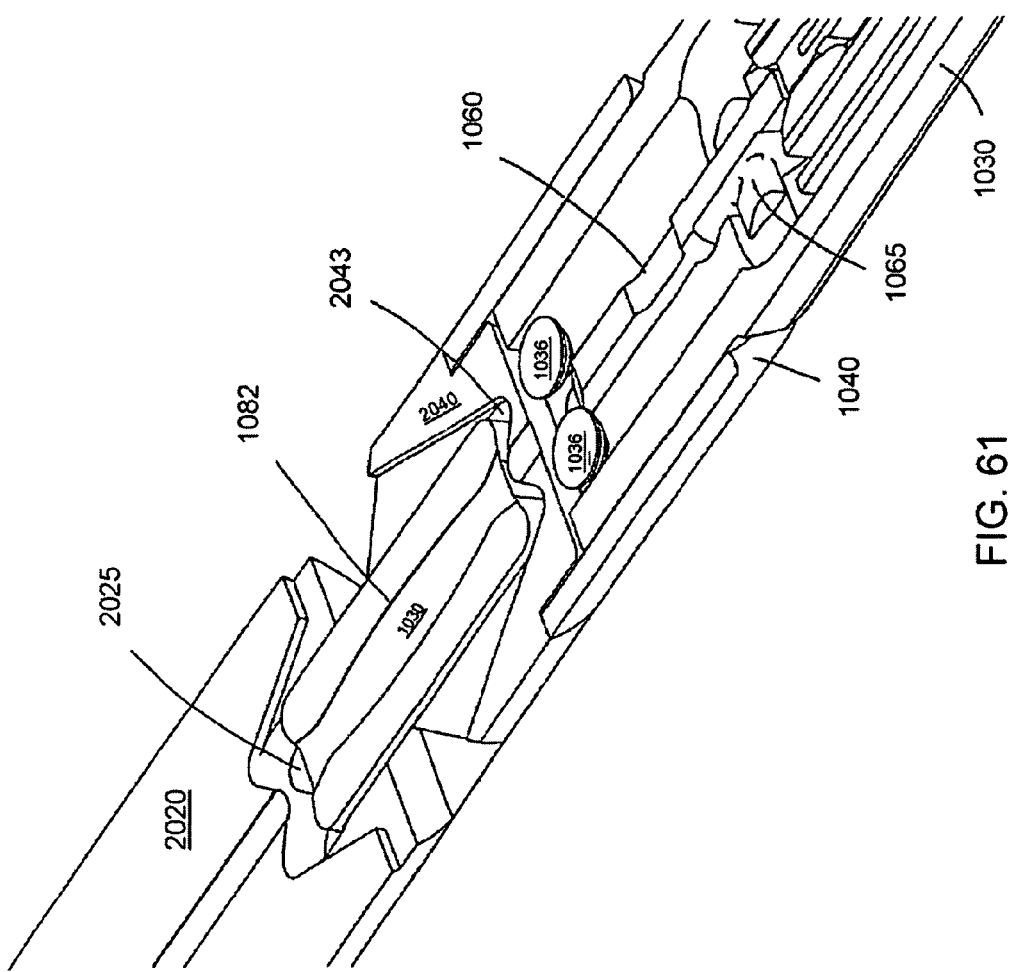
FIG. 61 is a fragmentary, horizontally longitudinal, cross-sectional view of the articulating portion of the end effector of FIG. 54 through a low intermediate portion of the dogbone guide.

FIGS. 18 to 24 are illustrations of the entire longitudinal extent of the stapling device according to the invention with the distal end effector 1 and a first exemplary embodiment of the actuating handle 2. As shown in FIG. 60, the jaws 20, 30 are at rest in an open position.

The thumb trigger is connected to the proximal end of the pull cable that ends at the pull cable adapter 70. Thus, when the thumb trigger 3 is actuated (see FIG. 19), the cartridge holder 30 is pulled in a proximal direction. Due to the shape of the cam surfaces 32, the cam followers 22 are caused to move and, thereby, pivot the anvil 20 approximately into its stapling position. As set forth above, it is not the thumb trigger 3 that insures correct parallel orientation of the anvil 20 with respect to the cartridge holder 30 and, thereby, the staple cartridge 100. Rather, it is the slide 60 that insures the proper parallel orientation.

Figure 22:
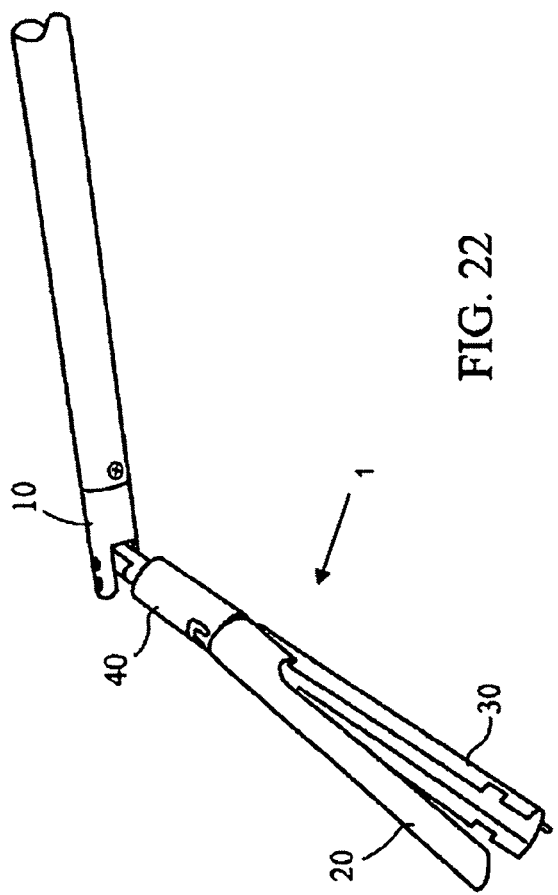
FIG. 22 is a fragmentary illustration of a left side of the end effector of FIG. 18 with the jaws open in the at-rest position and laterally positioned at an approximately 75 degree angle.

FIGS. 20 to 22 illustrate how the end effector 1 is passively articulated in a lateral direction. When the index finger trigger 4 is depressed, the lateral movement locking pin 120 is moved rearward to disengage from the sprocket 522. If no force is applied to the end effector 1, then, due to the two centering springs 130, the end effector 1 remains in the axial aligned orientation shown in FIGS. 18 and 19. However, when an external force is applied to the end effector 1 (as shown in FIG. 20), the laterally free end effector 1 can be moved about the axis of the sprocket 522 into any position, e.g., an approximately 45 degree left position shown in FIG. 20, or into any other orientation. See, e.g., FIG. 22. When the index finger trigger 4 is released, the lateral movement is prevented by returning the distal end of the locking pin 120 in between two teeth of the sprocket 522. Thus, as shown for example in FIGS. 21 and 22, the end effector can be locked into a significant number of laterally articulated positions. It is noted that the staple cartridge 100 is not illustrated in FIGS. 18 to 24 for clarity.

Figure 23:
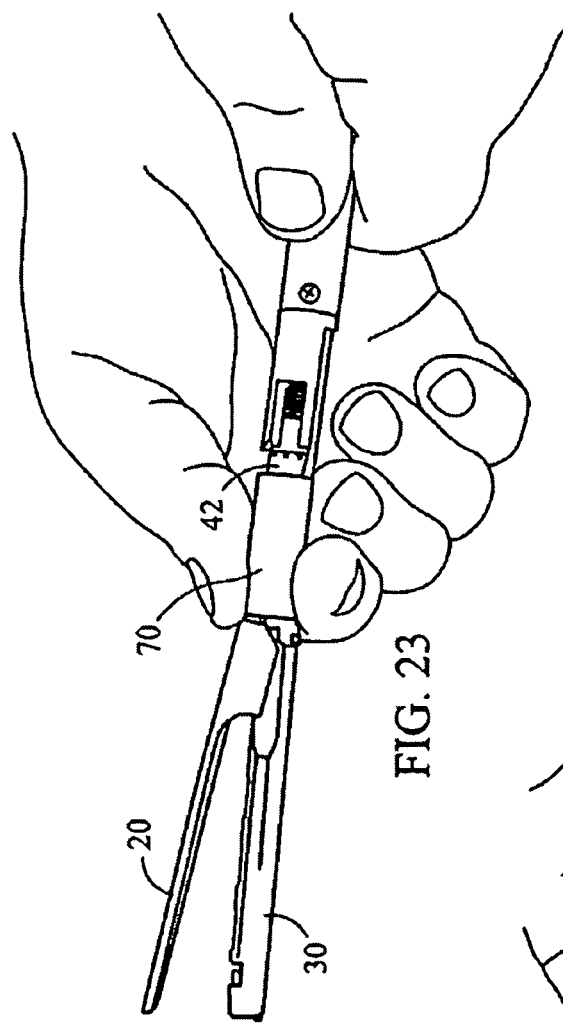
FIG. 23 is a fragmentary illustration of a left side of the end effector of the stapler of FIG. 18 with the jaws open in the at-rest position and in a rotated first axial position.
Figure 24:
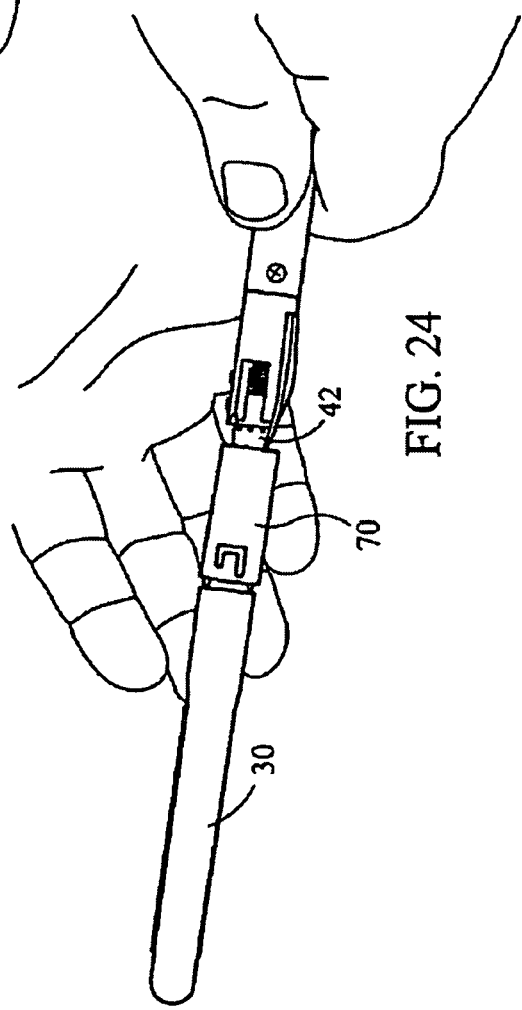
FIG. 24 is a fragmentary illustration of a left side of the end effector of FIG. 23 with the jaws open in the at-rest position and in a normal position rotated counter-clockwise with respect to FIG. 23.
Figure 68:
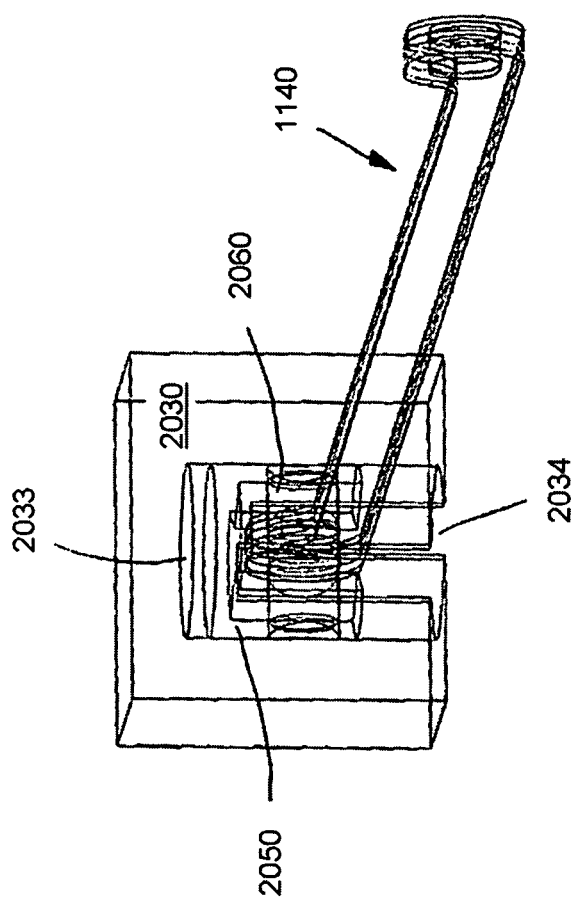
FIG. 68 is a fragmentary, wireframe, perspective view of an alternative embodiment of a distal connection of the pull-bands of the end effector of FIG. 54.

FIGS. 23 and 24 illustrate the axial rotational control of the end effector. Such axial control is provided by the two respective castellated features 422, 5242 of the adapter sleeve 40 and the lateral translation device 50, respectively. In FIG. 23, the castellations are engaged and the anvil is in the 90 degree position with respect to the handle. To disengage the castellations, a force sufficient to overcome the first biasing device is exerted on the end effector 1 and the castellation features 422, 5242 separate. Then, the end effector 1 can be rotated clockwise or counter-clockwise. FIG. 68 shows, for example, the anvil 20 rotated counter-clockwise into an approximately 9 o'clock position.

FIGS. 1 to 3 can be used to illustrate the operation of the motorized stapling function of the stapling device of the present invention. In FIG. 1, the slide 60 is in a proximal position. A reversible motor is housed inside the handle. A three-way switch is connected to the motor. When in a middle position, for example, the motor is off. When in a proximal position, the motor is turned on and will rotate the drive shaft 34 so that the slide 60 moves in a proximal direction. In contrast, when the switch is in a distal position, the motor is turned on and will rotate the drive shaft 34 so that the slide 60 moves in a distal direction. Of course, the switch can be merely a two-way switch without an off position.

Figure 25:
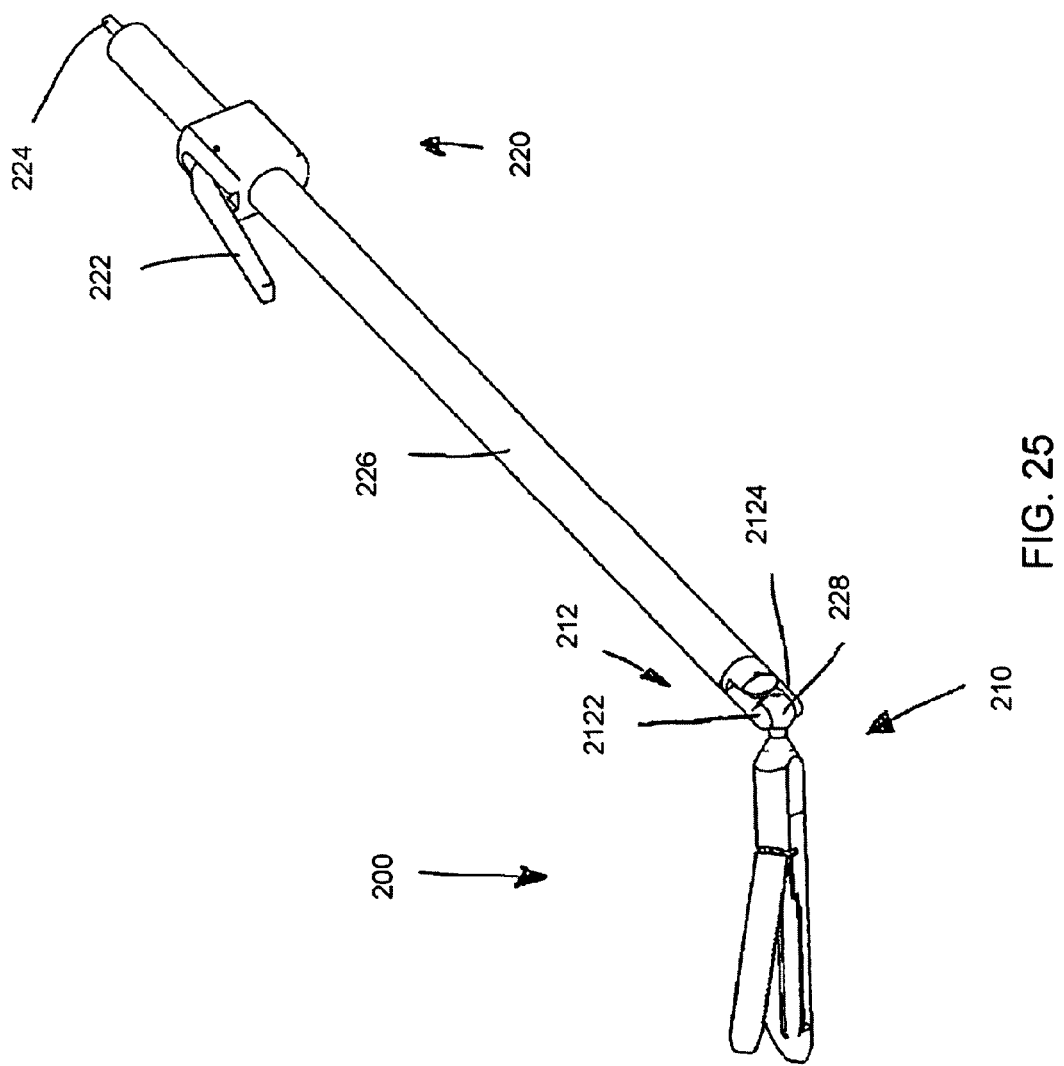
FIG. 25 is a perspective view from a distal end of a second embodiment of a surgical stapling device according to the invention with a removable end effector having a self-contained stapling motor, with the stapling jaws in an at-rest open position and at a right lateral position of approximately 45 degrees, with the ball release lever in an at-rest ball-capture position, and with the motor actuator button in an at-rest motor-off position.
Figure 26:
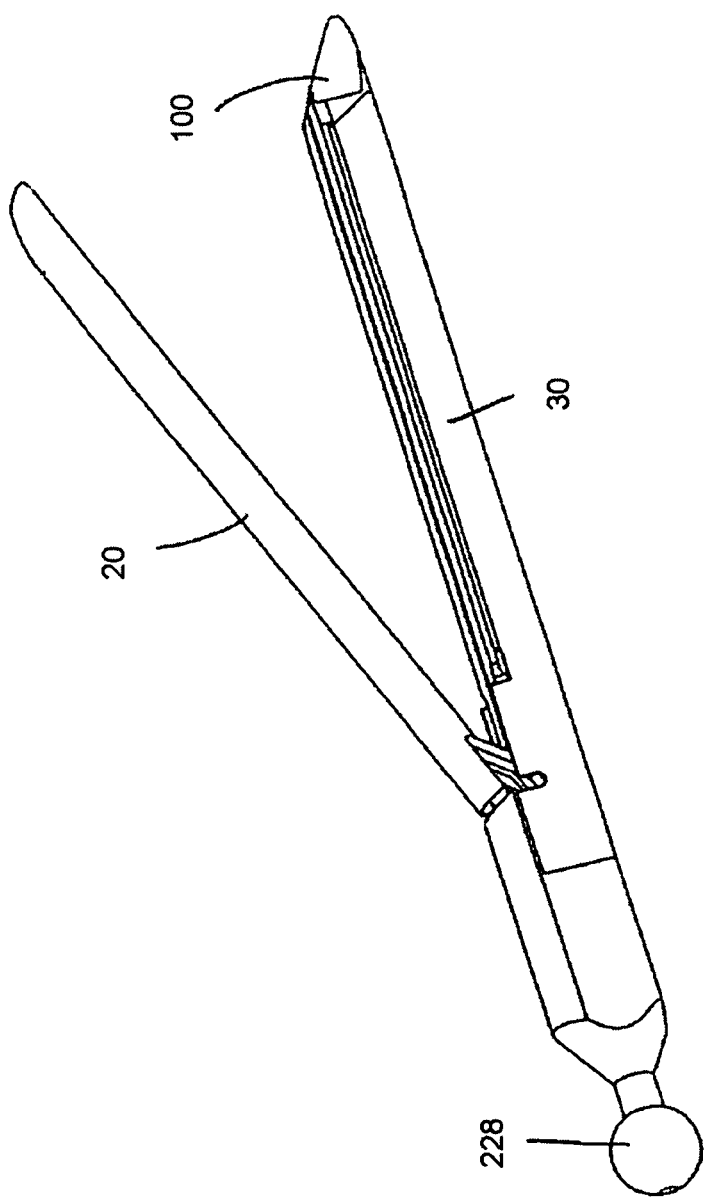
FIG. 26 is an enlarged, perspective view of the removable end effector of FIG. 25 with the jaws in an at-rest open position and with the slide removed for clarity.

FIGS. 25 and 26 illustrate a second exemplary embodiment of the stapling and cutting system 200 according to the invention. This system 200 is different than the first embodiment in that the motorized stapling assembly is entirely contained in the end effector 210. Therefore, the handle 220 only needs to have two actuating devices. The first actuating device 222 is a ball joint releasing lever and the second actuating device is the stapling/cutting motor on/off button 224.

The end effector 210 is connected to the distal end of the actuation shaft 226 of the handle 220 at a ball-joint connector 228. The end effector 210 has, at its distal-most end, a ball joint 212. The ball joint 212 has two opposing cup-shaped clamps 2122, 2124. The interior surfaces of the clamps 2122, 2124 are shaped to correspond to the outer shape of the ball joint 212. The clamps 2122, 2124 translate towards or away from one another based upon an actuation of the lever 222.

The clamps 2122, 2124 are biased towards one another in a closed position such that, when the ball joint 212 is disposed therein, the two clamps 2122, 2124 tightly grip the ball joint 212. Actuation of the lever 222 causes the clamps 2122, 2124 to separate and, thereby, allow the ball joint 212 to rotate freely in between the two clamps 2122, 2124. Thus, when the lever 222 is actuated, the end effector 210 is "free" to move based upon pressure against structures in the environment, such as tissue near a stapling/cutting site. The lever 222 can be pushed down sufficiently far to allow the ball joint 212 to move entirely out of the clamps 2122, 2124. Therefore, if a first end effector 210 is clamped at a first site and a second end effector 210 is desired to clasp and cut a second site, the first end effector 210 can be left clamped at the first site, the shaft 226 can be removed from the body and loaded with a second end effector 210, and the second end effector 210 can be guided to the second site.

The second actuating device 224 is needed when the user desires to effect the stapling and cutting with the end effector 210. When the end effector 210 is at the desired position for stapling/cutting, the actuator 224 (e.g., button) is depressed. This actuation, preferably, completes (or interrupts) a circuit that connects power to the motor inside the end effector 210, thereby causing the slide 60 to move distally and effect the stapling and cutting functions of the jaws.

FIG. 25 illustrates the complete freedom for orienting the end effector 210 in any position with respect to the ball joint 212. In FIG. 25, the end effector 210 is shown in a right lateral orientation of approximately 45 degrees and with an anvil orientation of approximately 90 degrees.

Figure 27:
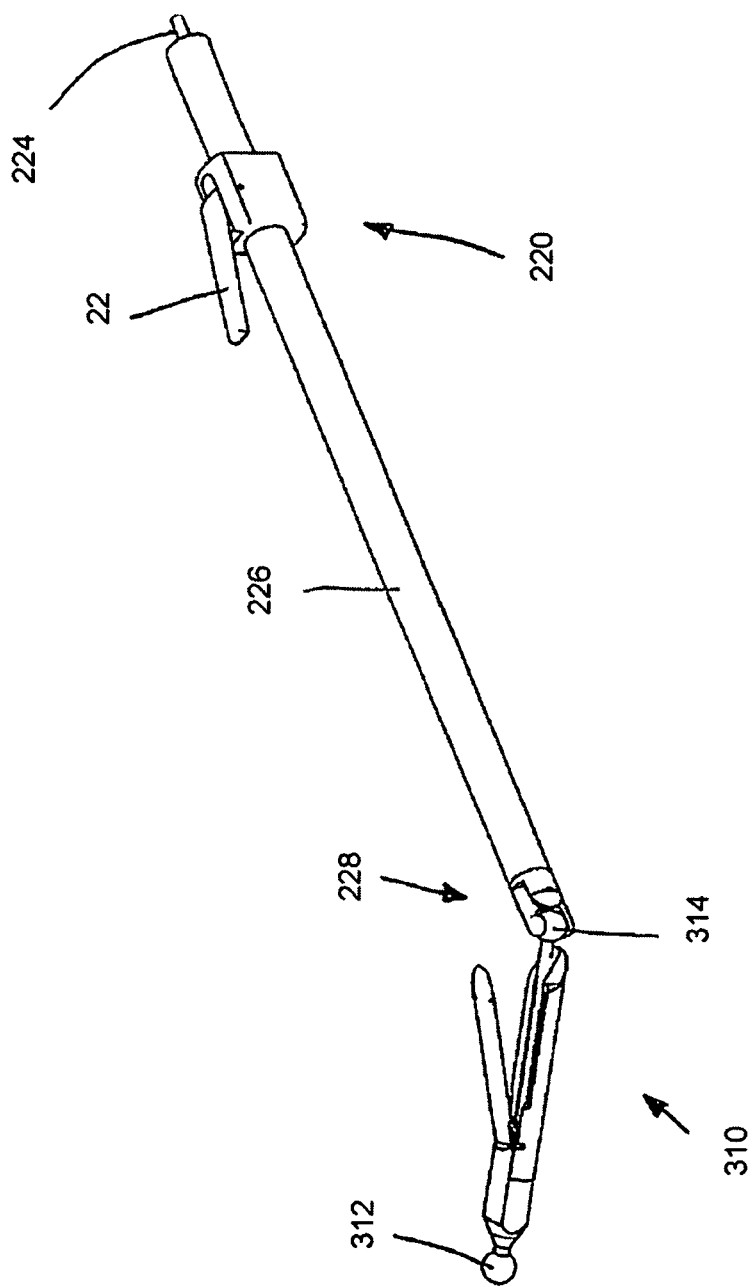
FIG. 27 is a perspective view from a distal end of a third embodiment of a surgical stapling device according to the invention with a removable end effector having two ball-connection ends and a self-contained stapling motor, with the stapling jaws in an at-rest open position and at a right lateral position of approximately 45 degrees with staple jaws reversed and facing proximally, with the ball release lever in an actuated ball-released position, and with the motor actuator button in an at-rest motor-off position.
Figure 28:
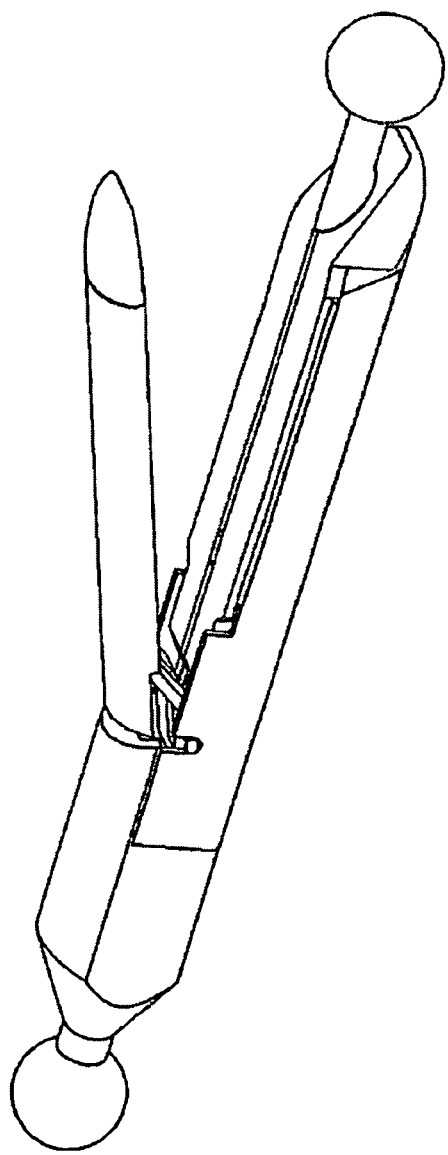
FIG. 28 is an enlarged, perspective view of the removable end effector of FIG. 27 viewed from a right side and a distal end thereof with the jaws in an at-rest open position and with the slide removed for clarity.

FIGS. 27 and 28 illustrate a variation of the second embodiment of the end effector shown in FIGS. 25 and 26. In particular, the handle 220 is the same as in FIGS. 25 and 26. However, the end effector 310 is different. Specifically, the end effector 310 has a proximal ball joint 312 similar to the ball joint 212 in FIGS. 25 and 26, but also has a second, distal ball joint 314, having a shape virtually identical to the proximal ball joint 312. Therefore, when the lever 222 is pressed down to release the ball joint 312, 314, the end effector 310 can be allowed to rest within the body and the opposite end can be grasped between the clamps 2122, 2124. In such an orientation, shown in FIG. 27, the stapling/cutting can be actuated when the jaw opening is facing the user.

It is also noted that placement of an end effector 210, 310 at a surgical site sometimes requires the access to the surgical site to be rather small in comparison to the opened jaws of the end effector 210, 310. With the ability to reverse the end effector 310, some difficult-to-reach sites may be accessed that are not reachable with the single ball joint end effector 210.

Figure 29:
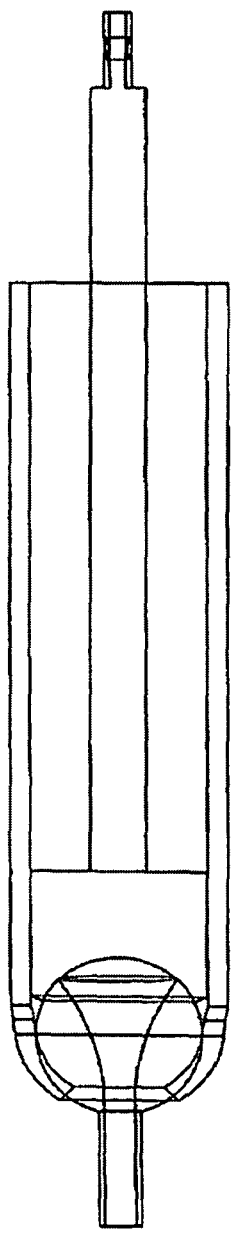
FIG. 29 is a fragmentary, enlarged side cross-sectional wireframe view of a distal-most end of an actuating handle of the surgical stapling and cutting device of FIGS. 25 and 26 and of a ball-joint of the removable stapling end effector of FIGS. 25 and 26 in a captured and aligned state.
Figure 30:
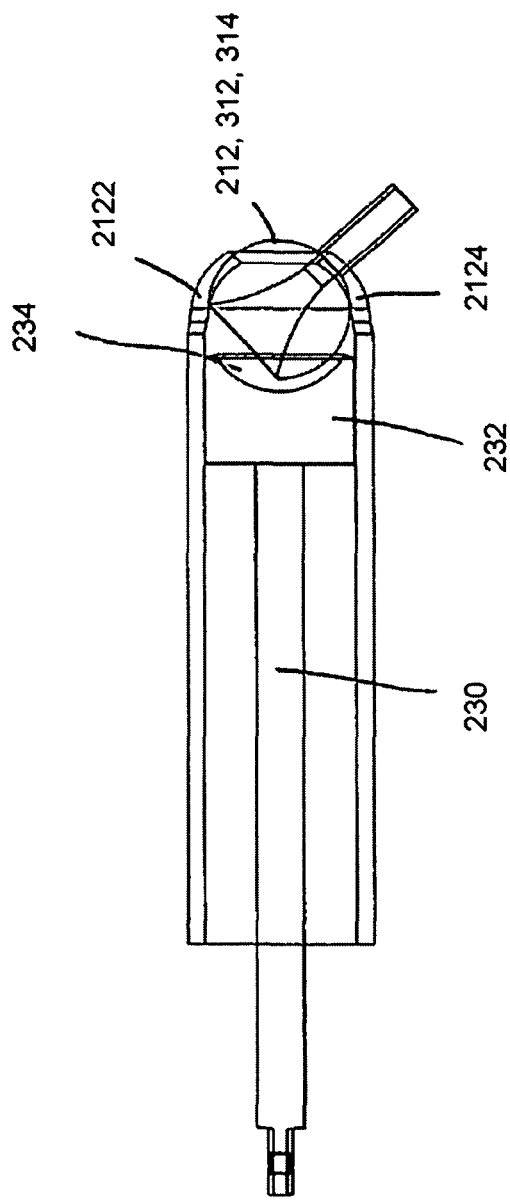
FIG. 30 is a fragmentary, enlarged side cross-sectional view of a distal-most end of opposite side of the actuating of FIG. 29 with the ball-joint in an un-aligned and released state but still captured in between clamps of the actuating handle.

FIGS. 29 and 30 show the clamps 2122, 2124 at the distal-most end of the actuating shaft 226 of the surgical stapling and cutting device 200, 300 of FIGS. 25 to 28 holding a ball-joint 212, 312, 314 of the end effector 210, 310 of FIGS. 25 to 28. These figures illustrate that the lever 222 is connected to a push rod 230 having at its distal end a plunger 232. This plunger 232 has a cup-shaped surface 234 at its distal-most end with a shape corresponding to the outer shape of the ball joint 212, 312, 314. Thus, when the plunger 232 is in its distal-most position in contact with the ball joint 212, 312, 314, the ball is captured and does not move or rotate. In contrast, when the plunger 232 is moved proximally as shown in FIG. 30, the ball of the ball joint 212, 312, 314 is free to rotate between the clamps 2122, 2124.

The endostapler illustrated in FIGS. 31 to 70 add various different alternative and/or additional features to the endostapler illustrated in FIGS. 1 to 30.

Figure 38:
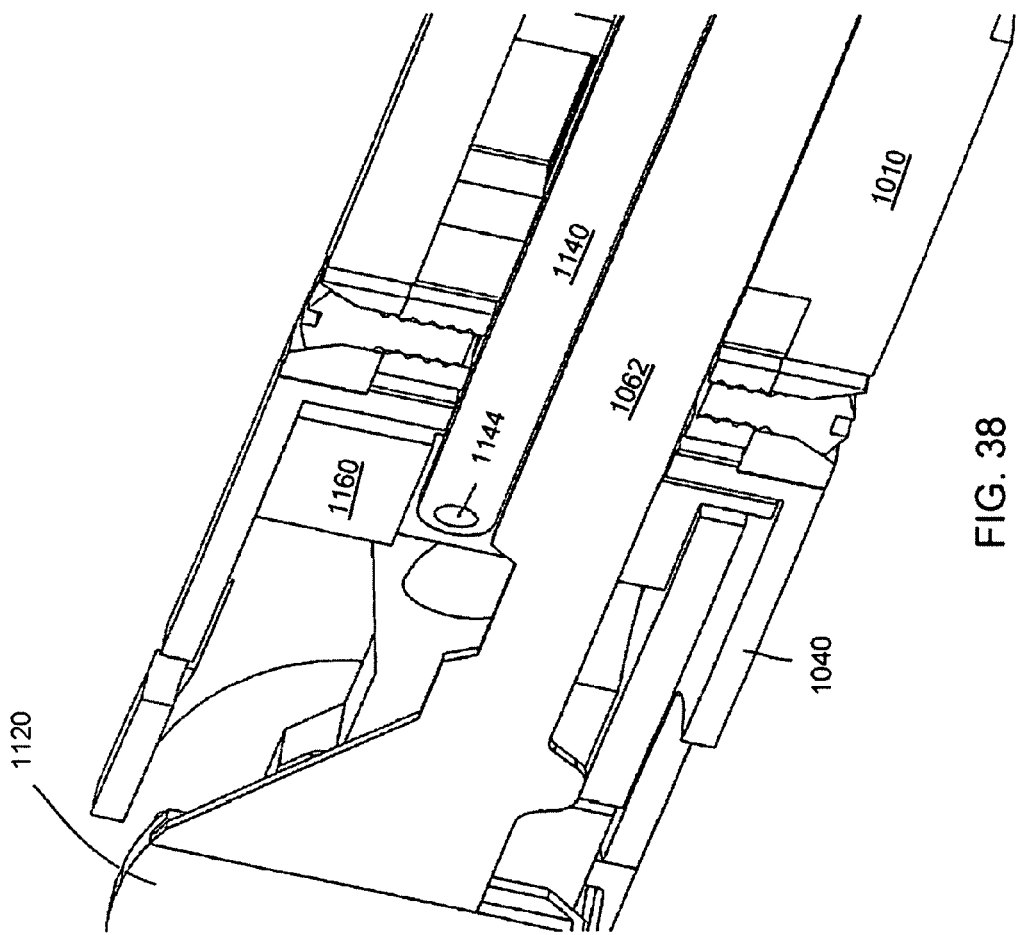
FIG. 38 is a fragmentary, enlarged, vertically longitudinal cross-sectional view of a portion of the parts of FIG. 35 at a distal end of the pullband.
Figure 39:
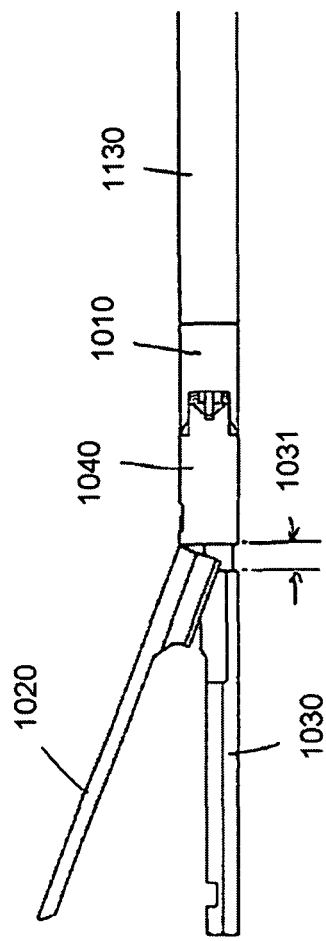
FIG. 39 is a fragmentary, enlarged, side elevational view of a stapler assembly, a drum sleeve, the articulation joint, and a clevis of the device of FIG. 31 with an anvil in an open position.
Figure 40:
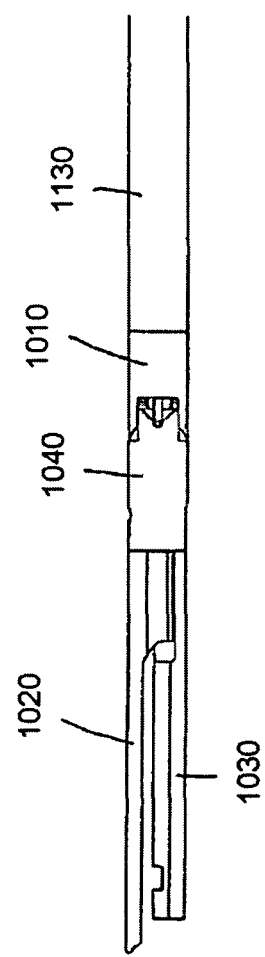
FIG. 40 is a fragmentary, enlarged, side elevational view of the stapler assembly, the drum sleeve, the articulation joint, and the clevis of the device of FIG. 31 moved distally with respect to FIG. 39 and with the anvil in a closed, firing position.

In all of FIGS. 31 to 70, the top jaw or anvil 1020 is only shown in FIGS. 39 and 40 for the sake of clarity. Further, the anvil 20 is described above in detail with regard to FIGS. 1 to 30 and, therefore, any repetitive description is avoided hereinafter.

Figure 31:
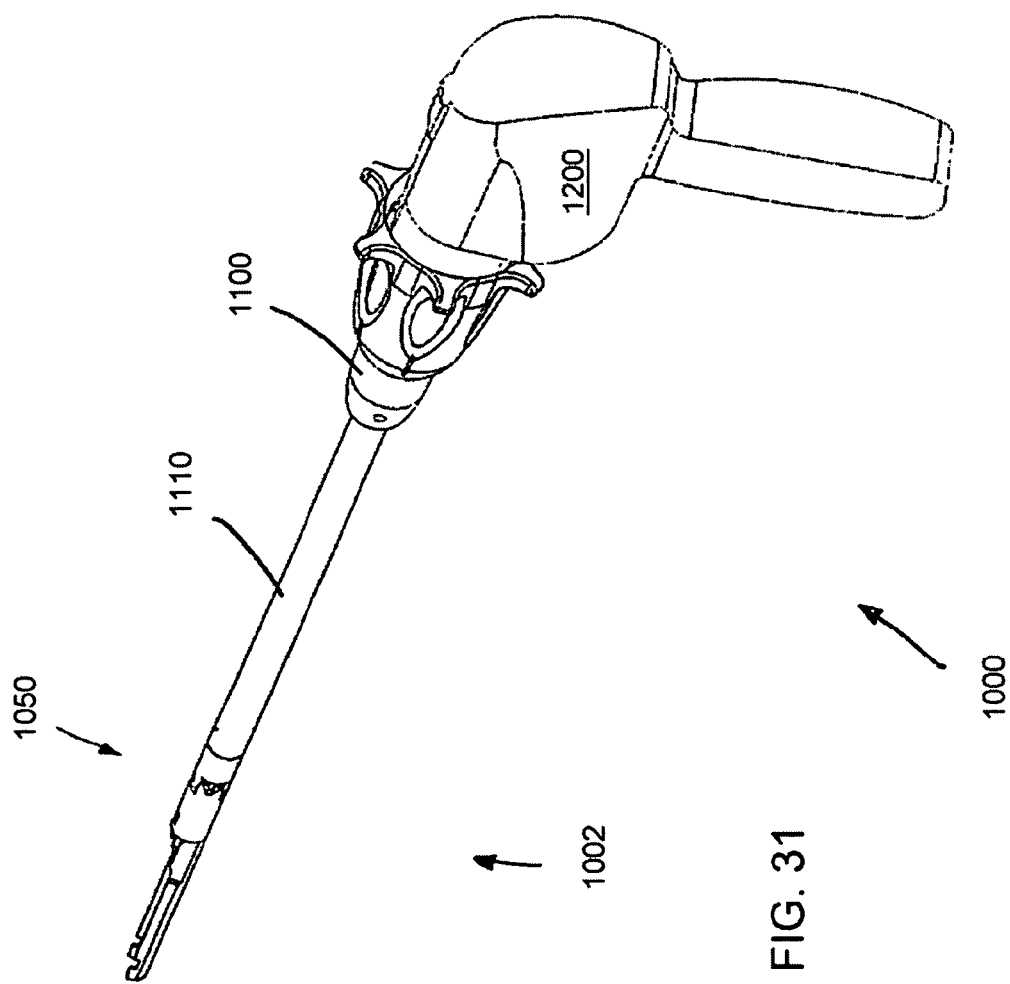
FIG. 31 is a perspective view from a proximal end of the stapling and cutting device according to the invention with an anvil removed.

The exemplary handle shown in FIG. 31 is manufactured by Ethicon Endo-Surgery, Inc., and can be found, for example, on Ethicon's linear cutter model ECHELON 60

Endopath Stapler. Description of this handle is, therefore, believed to be redundant as parts and functional descriptions of this handle are published in the art, for example, in U.S. Pat. No. 7,059,508 B2 to Shelton IV et al., which is hereby incorporated herein by reference in its entirety.

As set forth above, the distal end of the endostapler of the present invention is configured to house a standard staple cartridge 100. This cartridge 100, too, is described in prior publications and does not need to be repeated here. The publications are, therefore, hereby incorporated herein by reference in their entireties.

FIG. 31 illustrates portions of an alternative embodiment of the endostapler 1000 of the present invention. It is noted that two distal actuation levers on the handle 1200 of the endostapler 1000 are hidden from view in FIG. 31 for the sake of clarity.

The distal end of the handle 1200 includes a bell-shaped actuator 1100, which provides two degrees of control for the articulating portions of the endostapler 1000. First, the bell actuator 1100 freely rotates about the central axis of the endostapler 1000 on distal end of the handle 1200. Because the bell actuator 1100 is rotationally fixedly connected to the outer tube 1110, when the bell actuator 1100 is rotated clockwise or counterclockwise, the entire distal end of the endostapler 1000 rotates correspondingly. Second, the bell actuator 1100 can be displaced over a given distance in a proximal direction on the distal end of the handle 1200. As will be described below in further detail, proximal displacement of the bell actuator 1100 causes a corresponding movement of the articulation lock release slide 120, 1120 to allow the distal end effector 1002 to articulate at the translation device 50, 1050. A non-illustrated bias device (i.e., a compression spring) located, for example, in the distal portion of the bell actuator 1100 is used to bias the bell actuator 1100 and the articulation lock release slide 1120 in a distal direction so that the articulation lock release slide 120, 1120 remains in the actuated or locked position while the bell actuator 1100 is in an un-actuated state. See, i.e., FIGS. 8 and 9. This bias device is housed inside the bell actuator 1100 but is not shown in FIG. 32 for clarity. Also not shown is a snap ring that fits into a groove 1139 around the inner tube 1130. The bias device is delimited on the proximal side of the rod pullblock 1105 (see FIG. 34) and the distal side of the snap ring. In such a configuration, when the bell actuator 1100 is pulled proximally, the actuator 1100 forces the rod pullblock 1105 proximally to, thereby, move the articulation lock release slide 120, 1120 into an unlocked position. A keyhole on the interior surface of the bell actuator 1100 form-lockingly surrounds the rod pullblock 1105 so that rotation of bell actuator 1100 about the longitudinal axis of the inner tube 1130 forces the rod pullblock 1105 into a corresponding rotation. A form-locking or form-fitting connection is one that connects two elements together due to the shape of the elements themselves, as opposed to a force-locking connection, which locks the elements together by force external to the elements. As such, the inner tube and the entire distal assemblies of the device 1000 rotates as well. In an alternative configuration, the longitudinal movement of the bell actuator 1100 can function similar to a standard ball point pen by a first actuation placing the slide 120, 1120 in an unlocked state and a second actuation placing the slide 120, 1120 in a locked state.

With the bell actuator 1100 of the present invention, a physician is able to operate every function of the endostapler 1000 with one hand.

Figure 32:
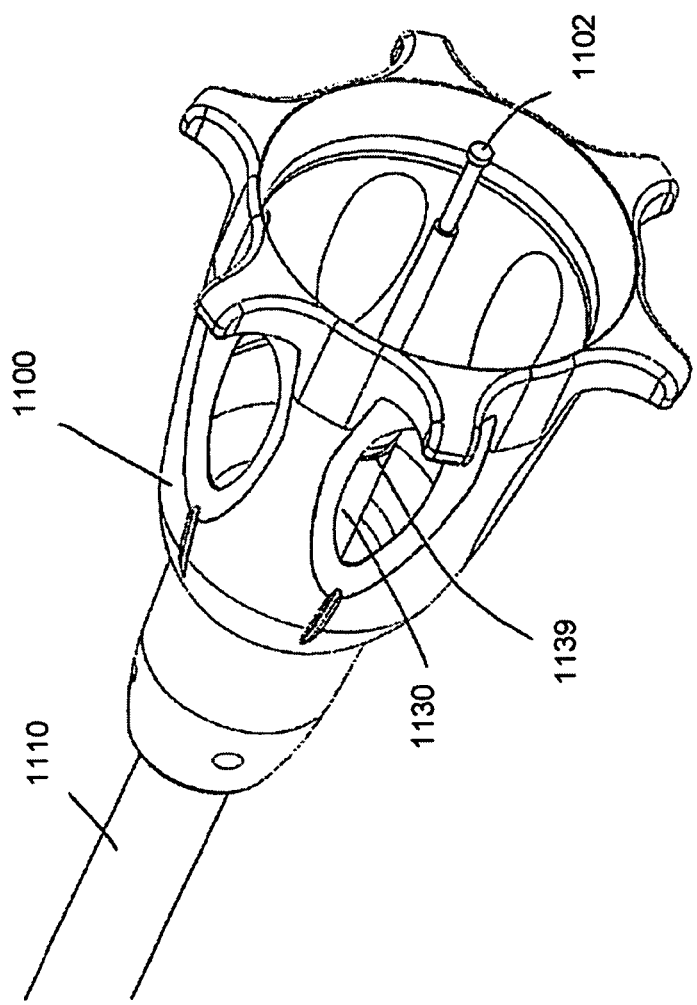
FIG. 32 is a fragmentary, perspective view from a proximal end of the device of FIG. 31 with the handle removed to show a proximal portion of an articulation release device with a pushrod therein.

FIG. 32 illustrates the proximal end of the endostapler 1000 without the handle 1200. Coaxially disposed inside the bell actuator 1100 is a pushrod 1102 that will be used to move the cutting blade 1060 when the stapler is in the firing orientation.

Figure 33:
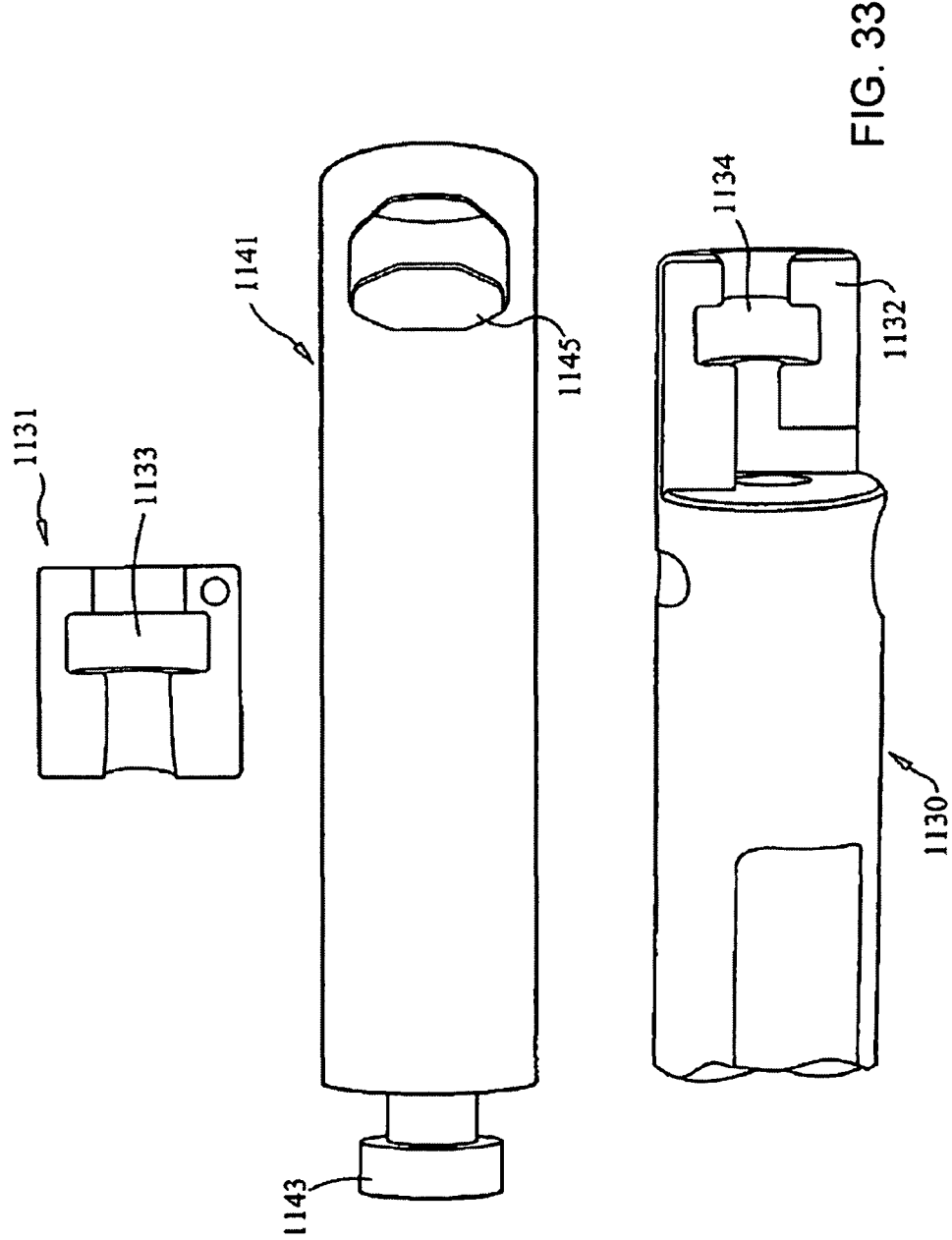
FIG. 33 is an illustration an enlarged, exploded view of parts of the proximal end of an inner tube of the device of FIG. 31.

FIG. 33 is an illustration of the parts at the proximal end of endostapler 1000 that axially fixedly and rotationally freely connect the distal assembly to the bell actuator 1100. More specifically, an inner tube 1130 (to be disposed inside the outer tube 1110) has a proximal extension 1132 defining an inner tube coupling chamber 1134. A clam-shell bushing 1131 has a length substantially equal to the extension 1132 of the inner tube 1130 and a bushing coupling chamber 1133 corresponding to the coupling chamber 1134 of the proximal extension 1132. A rotational couple 1141 has a distal T-shaped rotation link 1143 having an outer shape corresponding to both of the coupling chambers 1133 and 1134 so that, when the link 1143 is disposed between the extension 1132 and the bushing 1131, the link 1143 is free to rotate therein. This couple 1141 is fixed inside the handle 1200 through a proximal port 1145 on a proximal end of the couple 1141.

When placed together, the inner tube 1130 is axially held with respect to the couple 1141 but is rotationally independent of the couple 1141. Because the three coupling parts 1130, 1131, 1141 are sized to fit inside the outer tube 1110, when the parts are placed inside the outer tube 1110, the outer tube 1110 becomes a form-locking connection that prevents any separation of the inner tube 1130 and the bushing 1131 (so long as the outer tube 1110 sufficiently covers this area). Thus, when the bell actuator 1100 is rotated about the longitudinal axis of the inner tube 1130, the inner and outer tubes 1110, 1130 are able to rotate about the coaxial axis of the tubes 1110, 1130 but remain longitudinally stable with respect to the couple 1141, which is longitudinally fixed inside the handle 1200.

Figure 34:
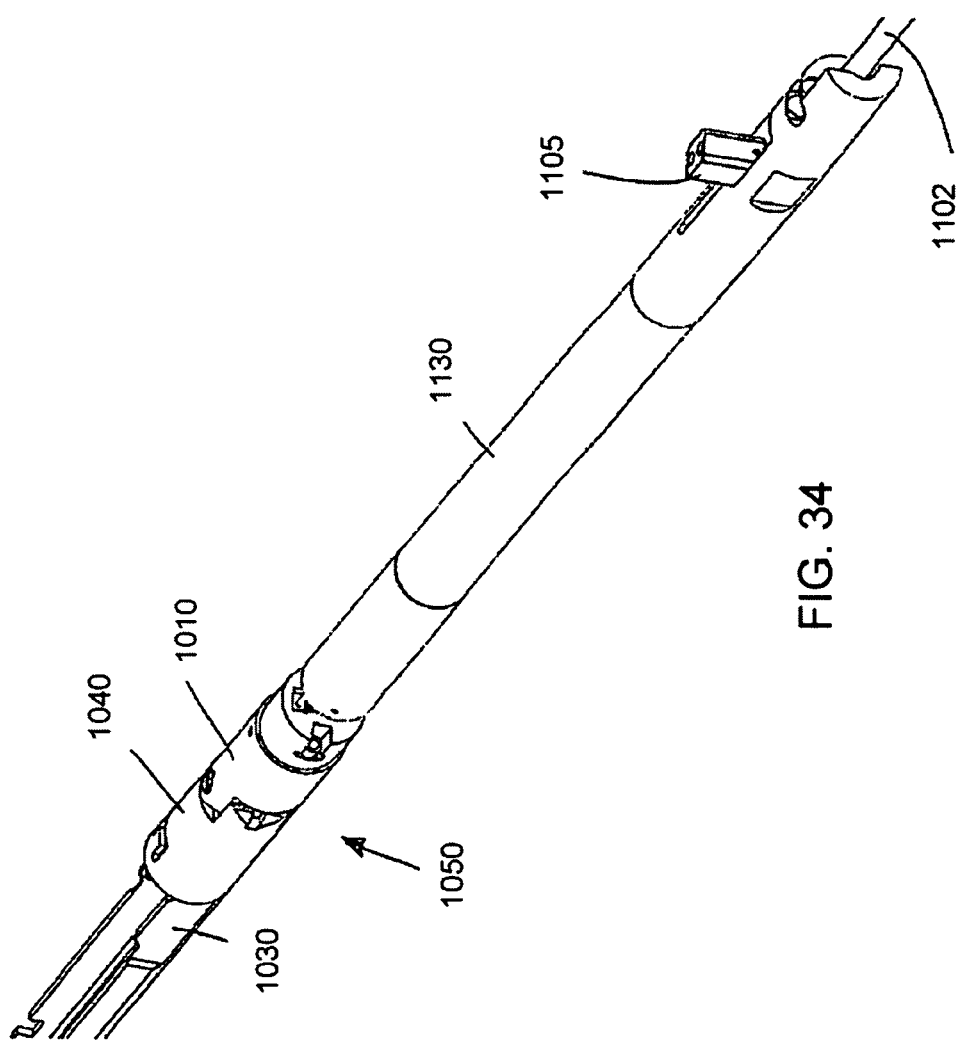
FIG. 34 is a fragmentary, perspective view from a distal end of interior parts connecting the articulation release device to the articulation joint of the end effector with an outer tube removed.

FIG. 34 illustrates the proximal end of the endostapler 1000 without the handle 1200, the bell actuator 1100, and the outer tube 1110. As can be seen, the inner tube 1130 is hollow and receives therethrough the pushrod 1102, which will be described in further detail below. Also shown in these figures are the clevis 1010 and the drum sleeve 1040, which, together, form the articulating connection or joint 1050 of the endostapler 1000.

It is noted at this point that the lower jaw/staple cartridge holder 1030 is longitudinally fixed with respect to the handle 1200. This fixation contrasts with the upper anvil 1020, which can be pivoted and be moved somewhat longitudinally when sliding through the keyhole shaped cam surfaces 32 to close and/or open the jaws (described in further detail below/above with respect to cam surfaces 1032).

To form the longitudinally fixed connection of the staple cartridge holder 1030 and the handle 1200, the inner tube 1130 must be connected to the staple cartridge holder 1030. But, at the same time, the staple cartridge holder 1030 must be able to articulate with respect to the longitudinal extent of the inner tube 1130. Thus, an axially fixed but laterally articulating connection must exist between the two parts 1030, 1130.

Figure 35:
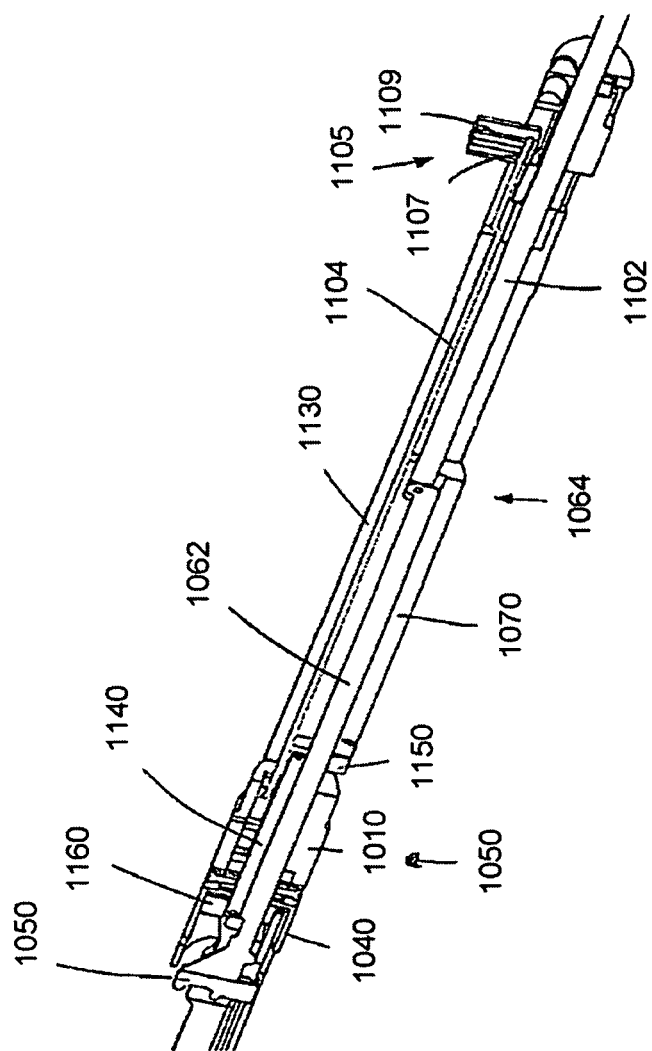
FIG. 35 is a fragmentary, enlarged, vertically longitudinal cross-sectional view of the parts of FIG. 34.
Figure 36:
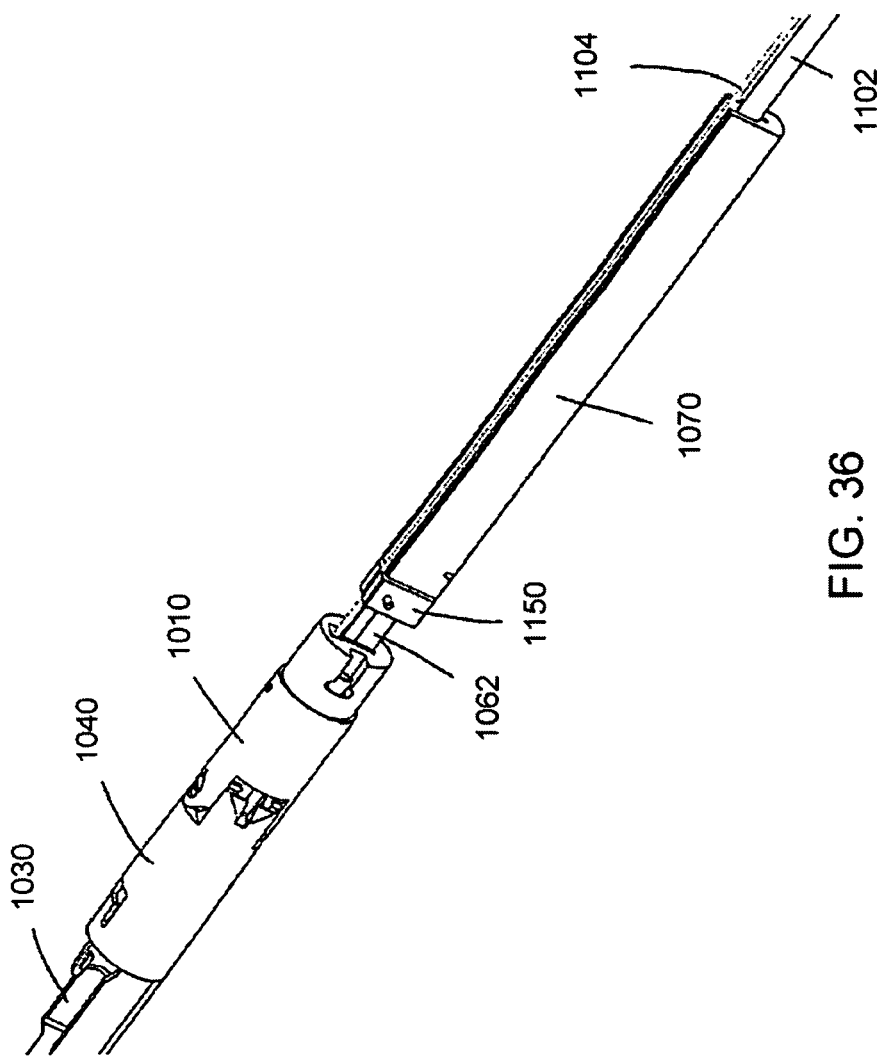
FIG. 36 is a fragmentary, enlarged, perspective view of a knife guide assembly of the device of FIG. 31 from proximal of a knife guide to distal of a knife blade with outer and inner tubes removed.
Figure 37:
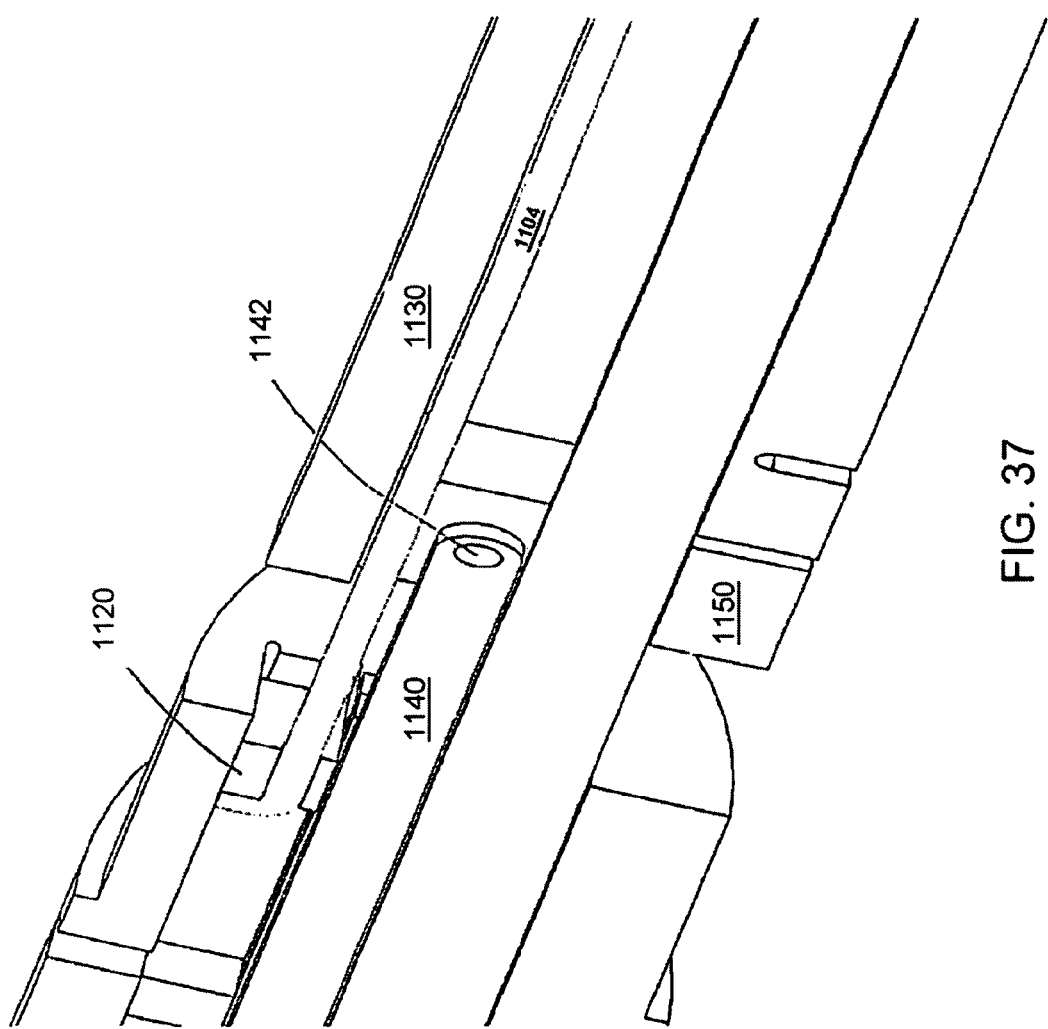
FIG. 37 is a fragmentary, enlarged, vertically longitudinal cross-sectional view of a portion of the parts of FIG. 35 at a proximal end of a pullband.

To provide such a connection, the present invention includes at least one pullband 1140, shown, for example, in FIGS. 35 to 38. In an exemplary configuration, multiple pullbands 1140 are provided, one next to the other. Three or four bands form two possible configurations. With two pullbands 1140 as opposed to one, the longitudinal strength remains approximately the same but the force needed to laterally bend the pullbands 1140 is reduced. The same is true for three or four pullbands 1140. FIG. 37 illustrates the proximal end of the pullband 1140, which is longitudinally pinned to the distal end of the inner tube 1130 with a proximal pullband pin 1142.

To provide a strong connection between the pullband 1140 and the inner tube 1130, a proximal guide block 1150, for example, made of brass, is disposed between the distal end of the inner tube 1130 and the pullband 1140.

The pullband 1140 spans the entire extent of the articulation joint 1050, as shown in FIG. 35, and is connected, as shown in FIG. 38, to a distal guide block 1160. The distal guide block 1160 (also, e.g., made of brass) has at least one projection that fits into at least one recess on the proximal end of the staple cartridge holder 1030. Later figures illustrate the measures by which the distal guide block 1160 is connected to the staple cartridge holder 1030 so that, finally, the staple cartridge holder 1030 is axially fixedly connected to the handle 1200 while being able to articulate with respect to the inner tube 1130. As shown in FIG. 38, a distal pullband pin 1144 axially locks the distal end of the pullband 1140 to the distal guide block 1160.

A first embodiment of jaw 20, 30 movement is described in the text above. There, the staple cartridge 30 moves axially and the anvil 20 is relatively stationary. In the configuration of the endostapler 1000 shown in FIGS. 31 et seq., movement is operationally opposite.

Noting that the staple cartridge holder 1030 is longitudinally fixed with respect to the handle 1200, there still must be an assembly that permits closure of the two jaws 20, 30; 1020, 1030. Closure is, therefore, accomplished by movement of the upper jaw/anvil 1020 as set forth in the following text.

A first of the two levers of the handle 1200 (e.g., a proximal handle) is operatively connected to the outer tube 1110 to move the outer tube 1110 distally when the first lever is compressed/actuated. Because the clevis 1010, the articulation joint 1050, and the drum sleeve 1040 are axially fixedly connected to the outer tube 1110 (and because the outer tube 1110 can slide longitudinally along the inner tube 1130), an actuation of the first lever moves the drum sleeve 1040 distally.

FIG. 39 illustrates the anvil 1020 in an open state. As can be seen therein, a gap 1031 exists between the distal end of the drum sleeve 1040 and a proximal shelf at the bottom of the staple cartridge holder 1030. In such an orientation, the drum sleeve 1040, the clevis 1010, and the outer tube 1110 are proximally disposed at a distance from the shelf.

FIG. 40 illustrates the anvil 1020 in a closed state. As can be seen therein, no gap 1031 exists between the distal end of the drum sleeve 1040 and the proximal shelf of the staple cartridge holder 1030. In such an orientation, the drum sleeve 1040, the clevis 1010, and the outer tube 1110 are in a position where the drum sleeve 1040 contacts the shelf.

In contrast to the axially fixed position of the staple cartridge holder 1030 with respect to the handle 1200, and similar to the movement of the drum sleeve 1040, the knife 60, 1060 must translate with respect to the handle 1200 along the longitudinal axis. FIGS. 35, 36, and 38 to 41 illustrate the axially displaceable connection of the knife 1060 to the knife-moving features of the handle 1200.

With regard to FIG. 35, a pushrod 1102 extends from the handle 1200 and is connected to a second non-illustrated lever (e.g., a distal lever) of the handle 1200. The distal end of the pushrod 1102 is connected to at least one flexible knife blade 1062 through a pushrod pin 1122. The distal end of the knife blade 1062 is connected to the proximal side of the cutting blade 1060 such that the cutting blade 1060 moves distally or proximally to follow corresponding movement of the pushrod 1102. It is noted that the knife blade 1062 has a proximal, upwardly extending flange 1064 that houses a bore for receiving the pushrod pin 1122. This off-axis connection between the pushrod 1102 and the knife blade 1062 causes the distal end of the knife blade 1062 to be forced downwardly when pushed in the distal direction and, therefore, to stay in position inside a pushrod-blade support 1070 shown, for example, in FIGS. 36 and 42.

Figure 42:
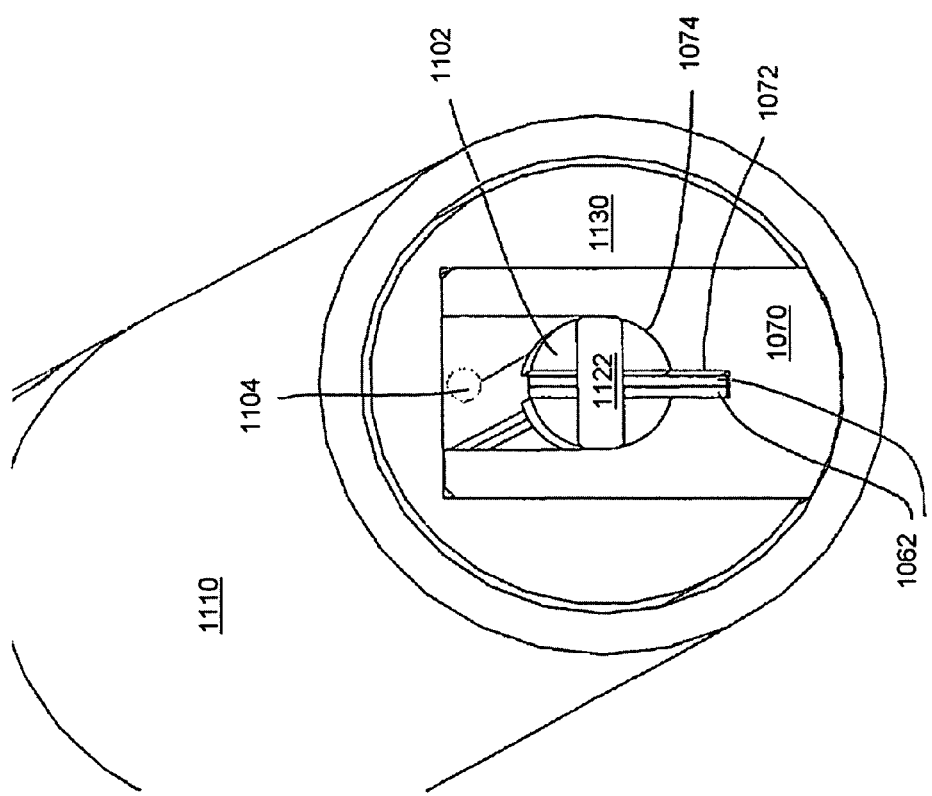
FIG. 42 is a fragmentary, enlarged, vertically transverse cross-sectional view of the knife-pushrod pin joint of the device of FIG. 31.

The knife blade 1062 is flexible enough to bend in any way that the articulation joint 1050 bends. Therefore, the knife blade 1062 is also flexible enough to possibly kink if it was not supported. The present invention, therefore, provides a pushrod-blade support 1070, which is shown in FIGS. 36 and 42. Therein, the proximal end of the pushrod-blade support 1070 clearly reveals the rectangular blade channel 1072 for supporting slidably the rectangular knife blade 1062. Also shown therein is a curved pushrod channel 1074 for supporting slidably the curved (e.g., cylindrical) exterior of the pushrod 1102. Thus, the pushrod-blade support 1070 supports the pushrod 1102 at locations where the pushrod 1102 is inside the support 1070 and also supports the knife blade 1062 where the knife blade 1062 is inside the support 1070.

FIG. 36 shows the connection of the support 1070 and its relation to the proximal guide block 1150.

Like the pullbands 1140, more than one knife blade 1062 can be next to one another. In such a configuration, the multiple blades 1062 have the same longitudinal stiffness but provide greater flexibility when there is a bend in the articulation joint 1050.

Figure 41:
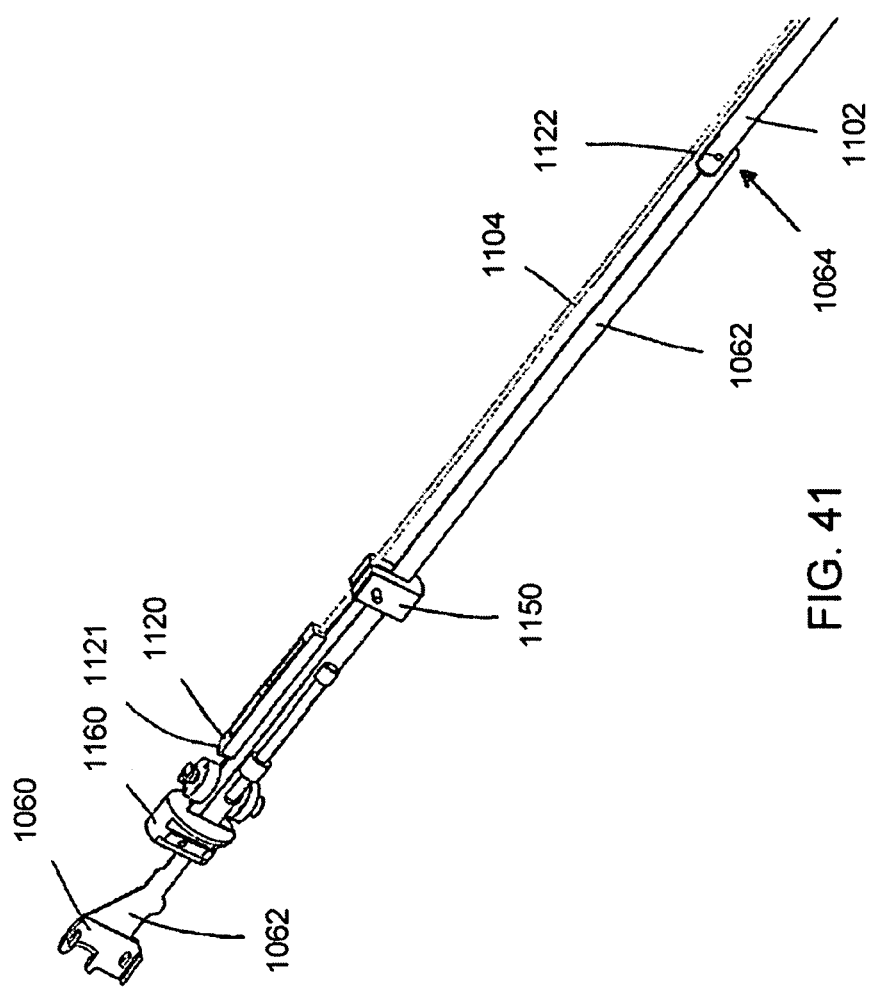
FIG. 41 is a fragmentary, enlarged, perspective view of a knife guide sub-assembly from proximal of the knife guide to the knife blade with the knife guide, the clevis, the left hammock, the drum sleeve, and the cartridge holder removed.

Revealed in FIG. 41 is the articulation lock release slide 1120 that locks the articulation of the jaws 1020, 1030.

FIGS. 42 to 50 illustrate a vertical cross-section of the tube portion distal of the handle 1200 along planes that are orthogonal to the longitudinal axis of the endostapler 1000.

FIG. 42 shows the cross-section of the connection junction of the knife blade 1062 and the pushrod pin 1122. The pushrod pin 1122 passes through the entirety of two adjacent blades 1062 and the pushrod 1102 but does not extend outside the pushrod's outer surface. This figure also illustrates the relationship of the inner and outer tubes 1130, 1110 and the pushrod-blade support 1070. Also apparent in this figure is an unlock pullrod 1104 used for unlocking the lock release slide 1120. The longitudinal extent of the unlock pullrod 1104 is first shown in FIG. 35 and is also shown in FIGS. 36, 37, 41, and 52 and 53. Most particularly, with exterior parts hidden, FIG. 41 shows how the pullrod 1104 connects the bell actuator 1100 to the articulation lock release slide 1120. With the distal end of the pullrod 1104 passed through and wrapped around the distal end of the articulation lock release slide 1120 as shown in FIG. 37, the unlock pullrod 1104 establishes a longitudinally fixed connection between the bell actuator 1100 and the articulation lock release slide 1120. As such, when the bell actuator 1100 is moved proximally, the articulation lock release slide 1120 moves in a corresponding proximal direction to separate the distal teeth 1121 of the articulation lock release slide 1120 and the spokes 1041 of the sprocket 1522. See, in particular, FIGS. 46 and 52. It is noted that the wrapped connection between the pullrod 1104 and the articulation lock release slide 1120 is only an exemplary embodiment. Other form-locking or force-locking connections are possible as well.

Figure 43:
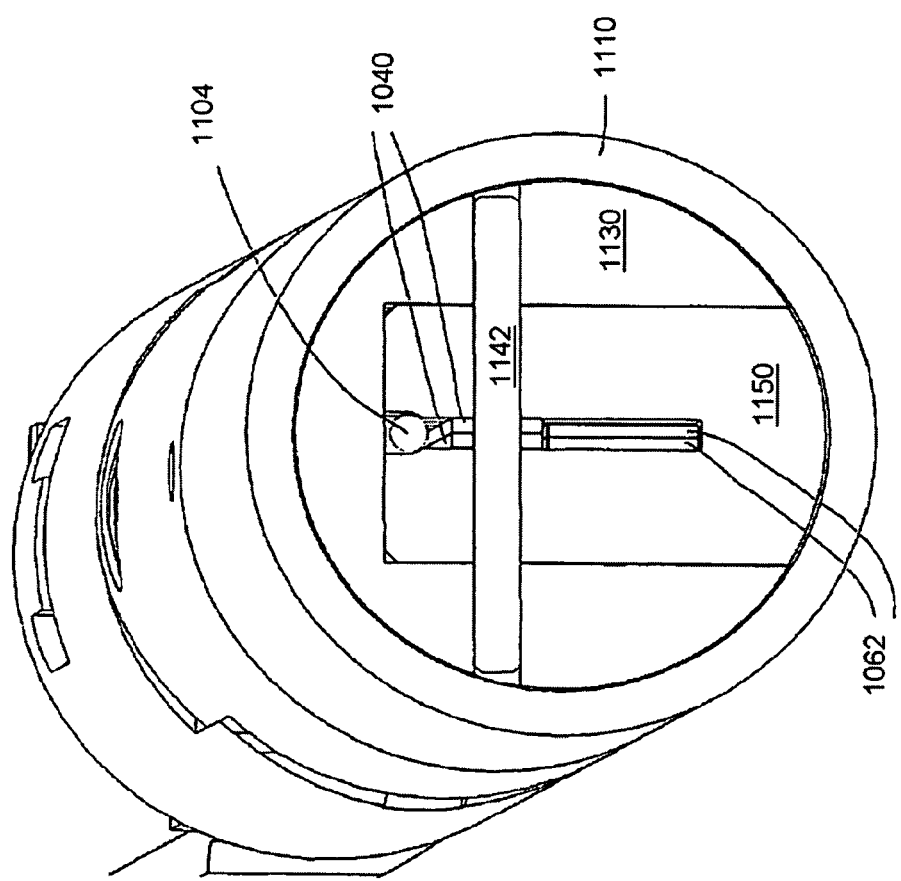
FIG. 43 is a fragmentary, enlarged, vertically transverse cross-sectional view of the pullband-aluminum tube pin joint of the device of FIG. 31.

FIG. 43 shows the connection through the pullband 1140 and inner tube 1130 pin joint. As set forth above, the proximal pullband pin 1142 passes entirely through the blades 1062, the proximal guide block 1150, and the inner tube 1130 but not through the outer tube 1110.

Figure 44:
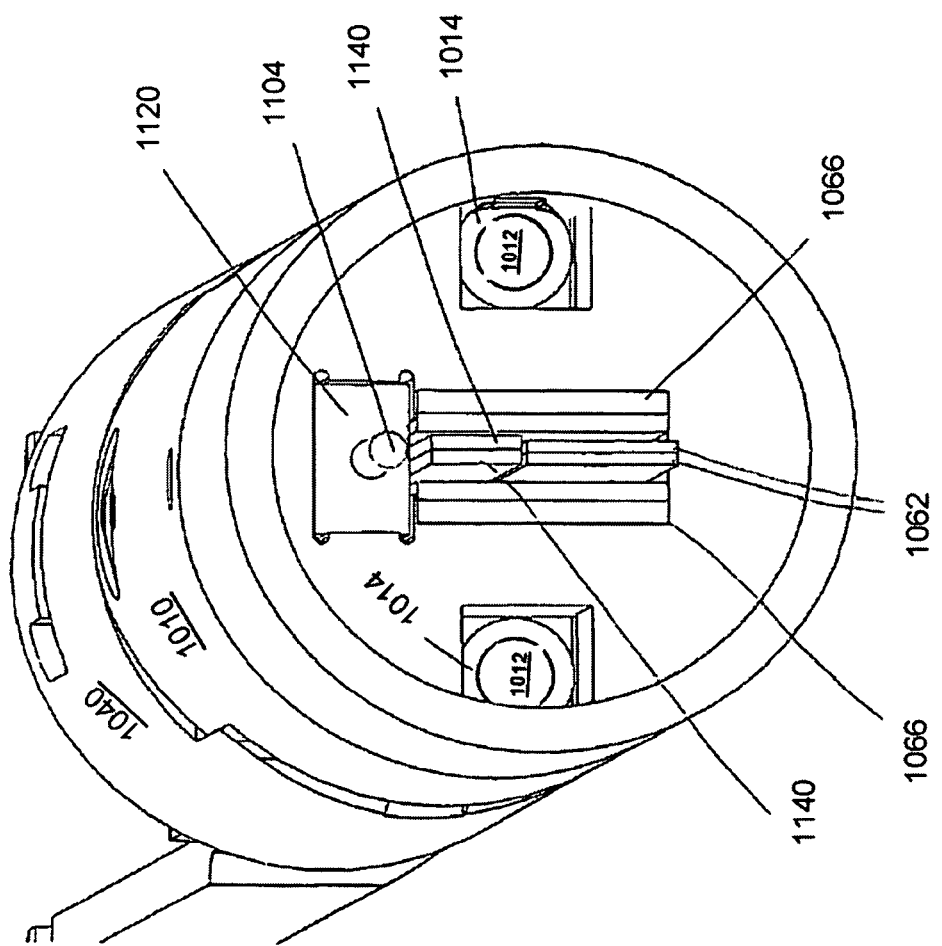
FIG. 44 is a fragmentary, enlarged, vertically transverse cross-sectional view of a proximal face of the clevis of the device of FIG. 31.
Figure 50:
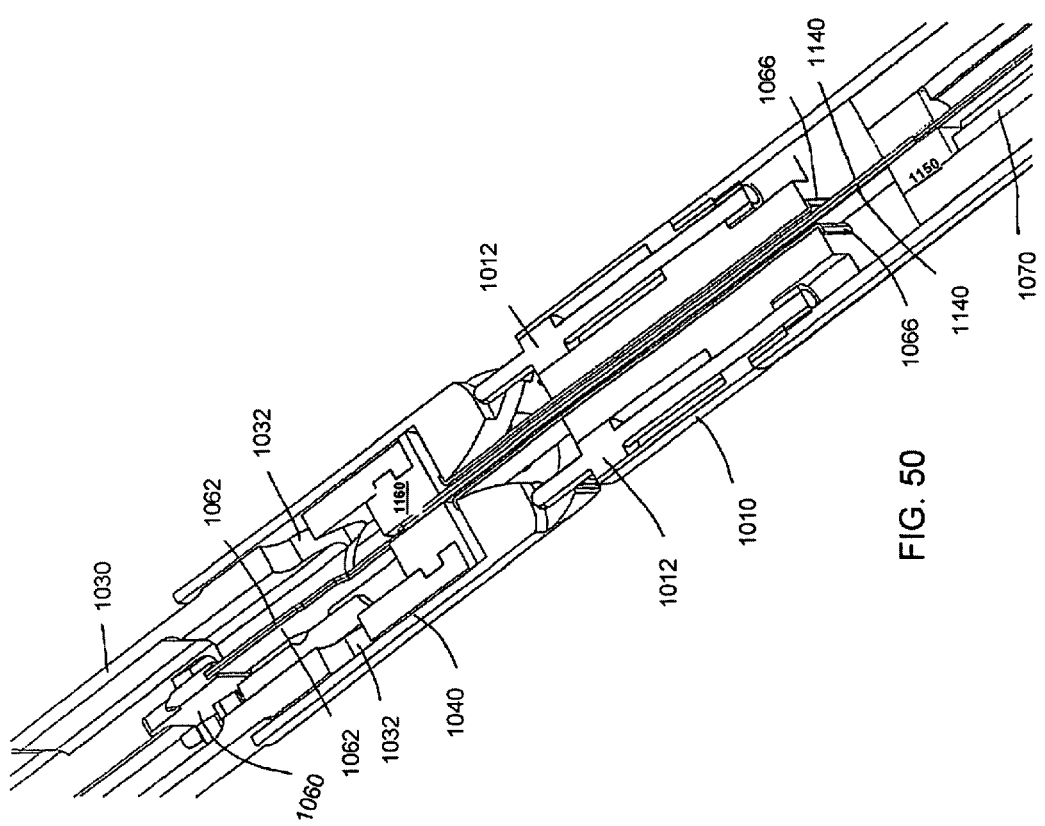
FIG. 50 is a fragmentary, enlarged, horizontally longitudinal cross-sectional view of the articulation joint portion of the device of FIG. 31 through spring rods.

FIG. 44 shows the area immediately proximal of the proximal end of the articulation lock release slide 1120. In this exemplary embodiment, two pullbands 1140 are disposed above two blades 1062. To provide support to at least one of the pullbands 1140 and the blades 1062, a pair of hammocks 1066 is placed along sides of the articulating portions of the pullbands 1140 and blades 1062. Each of the hammocks 1066 has a U-shape (along a longitudinal cross-section) so that the proximal arm of each hammock 1066 bends around the proximal surface of the clevis 1010 and the distal arm of each hammock 1066 bends around a catching surface within the drum sleeve 1040, as shown in FIG. 50, for example.

Inside the clevis 1010 are disposed two spring rods 1012 about which are respective spring rod collars 1014, the function of which is to bias laterally the entire assembly distal of the articulation joint 1050 towards and along the longitudinal axis. The spring rods and collars 1012, 1014 will be described in further detail below.

Figure 45:
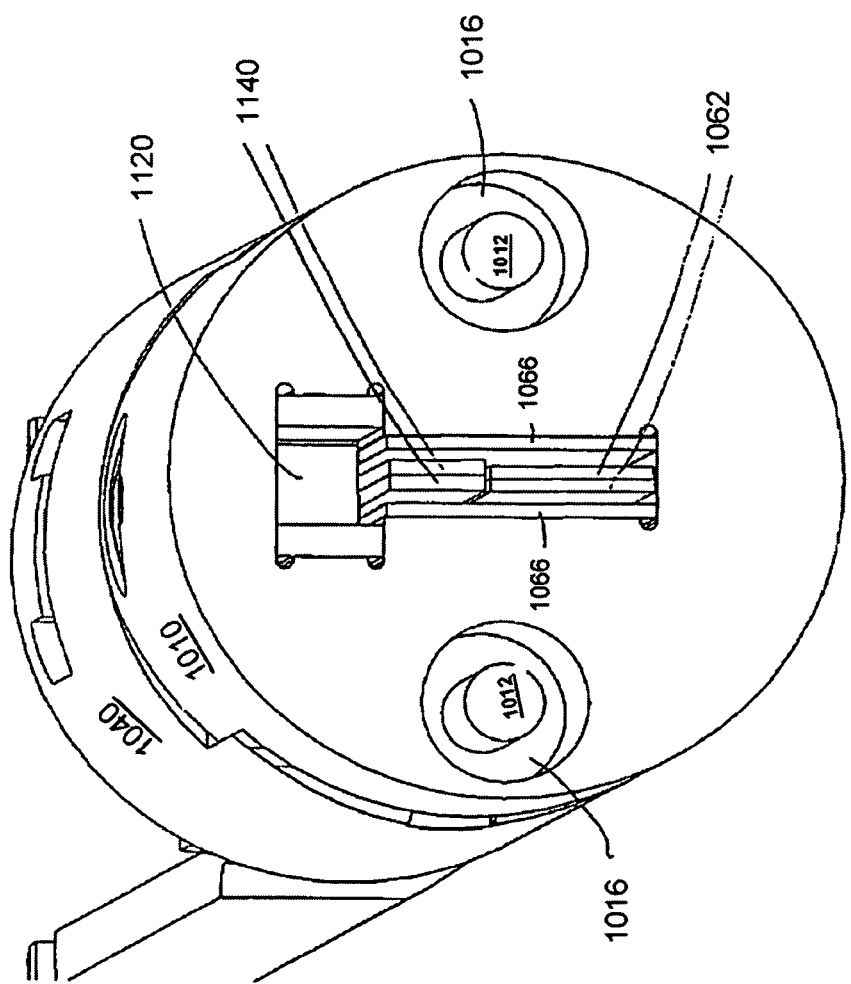
FIG. 45 is a fragmentary, enlarged, vertically transverse cross-sectional view of plunger pin spring pockets and an articulation release pin of the device of FIG. 31.

FIG. 45 illustrates the open area in the center of the articulation lock release slide 1120 that receives the bend portion of the pullrod 1104 (not illustrated in this figure). Also shown are the cavities 1016 in which the non-illustrated bias springs of the spring rods 1012 rest. This cross-sectional area also includes portions of the two pullbands 1140 disposed above the two knife blades 1062.

Figure 46:
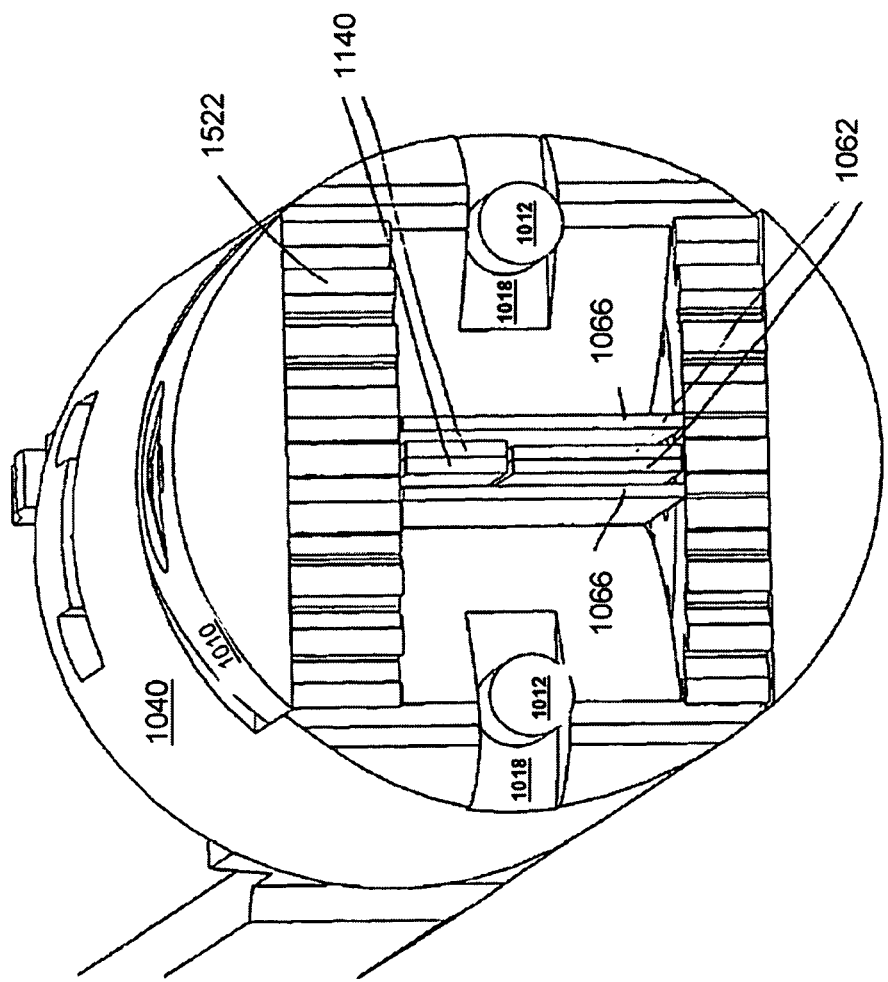
FIG. 46 is a fragmentary, enlarged, vertically transverse cross-sectional view of a plunger pin cam surface and an articulation locking sprocket of the device of FIG. 31.

FIG. 46 illustrates the open area in which the distal end of spring rods 1012 acts against cam surfaces 1018. It is noted that the cam surfaces 1018 are arcuate in shape so that contact between the spring rods 1012 and the cam surfaces 1018 always act in an axial direction normal to the surface at the distal-most end of the spring rods 1012. See, for example, FIG. 56. In such a configuration, the force that is applied by the spring rods 1012 against the cam surfaces 1018 to bias the distal articulating assembly (e.g., anvil 1020, staple cartridge holder 1030, drum sleeve 1040) towards the longitudinal axis of the inner and outer tubes 1130, 1110 is always at the same radius about the articulation axis of the articulating staple cartridge holder 1030. One advantage of such a configuration lies in the fact that the spring rods 1012 are not forced laterally in any way, in which case, the distal-most end of the spring rods 1012 could catch and lock on the cam surface 1018.

Figure 47:
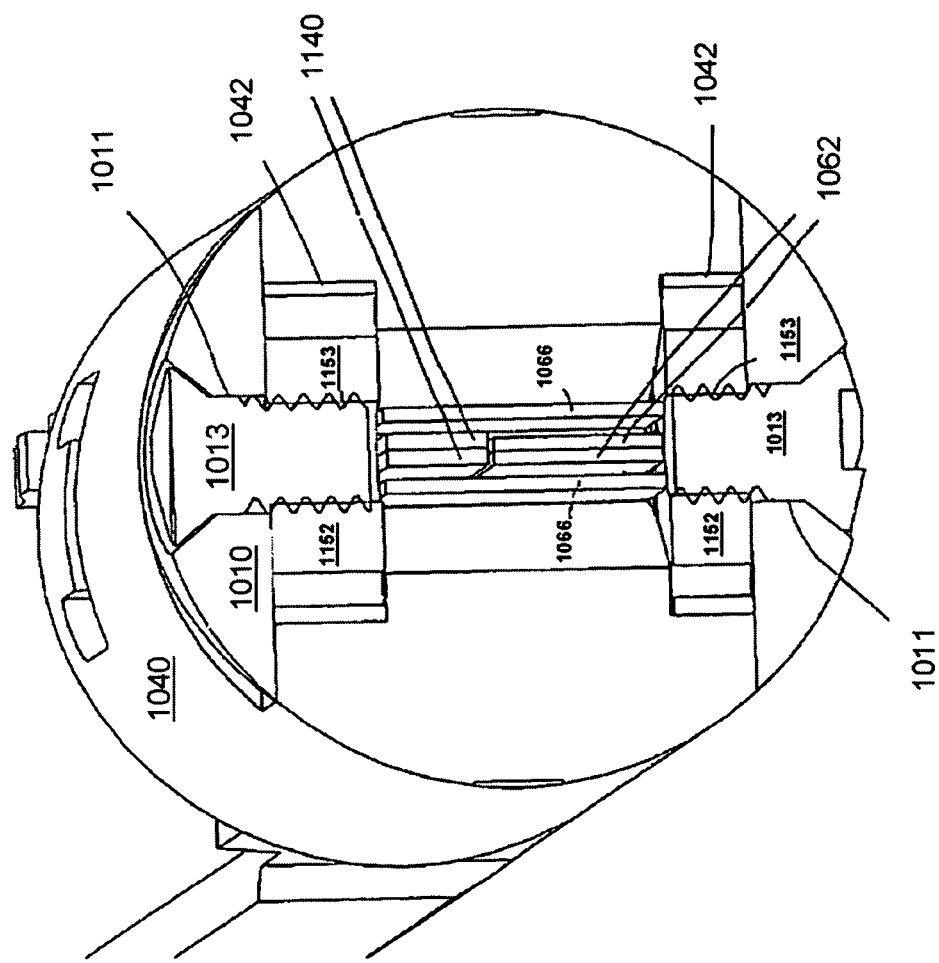
FIG. 47 is a fragmentary, enlarged, vertically transverse cross-sectional view of the end effector articulation joint of the device of FIG. 31.

FIG. 47 illustrates, in cross-section, the area within the endostapler articulation joint 1050. Again, this area includes portions of the two pullbands 1140, of the two blades 1062, and of the two hammocks 1066. Upper and lower axle pucks 1152 are inserted in orifices 1042 above and below on surfaces of the drum sleeve 1040. Connection of the clevis 1010 to the drum sleeve 1040 at the articulation joint 1050 is symmetrical on the top and bottom. The pucks 1152 are inserted into the orifices 1042 in the top and bottom of the proximal end of the drum sleeve 1040. In this orientation, the assembly is inserted into the distal end of the clevis 1040 to align screw holes 1011 with center threaded bores 1153 of the pucks 1152. When aligned, screws 1013 are threaded respectively into the pucks 1152 to axially secure the drum sleeve 1040 into the clevis 1010 while allowing the drum sleeve 1040 to articulate about the axis defined by the longitudinal axis of the two screws 1013.

Figure 48:
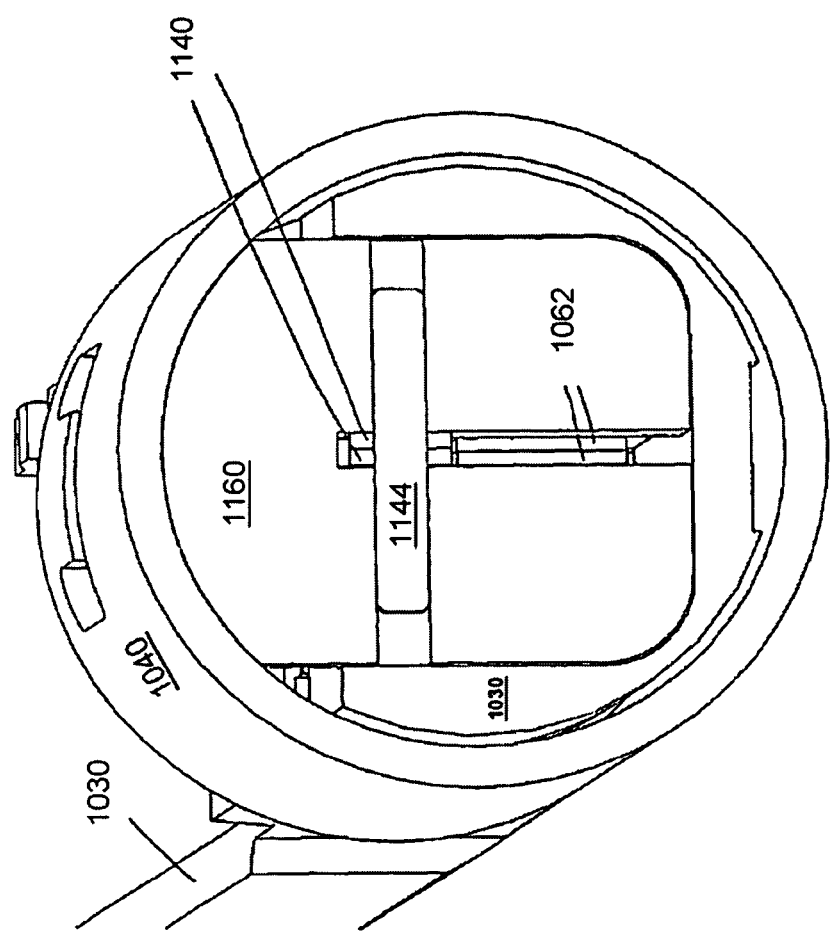
FIG. 48 is a fragmentary, enlarged, vertically transverse cross-sectional view of a distal pullband pin joint of the device of FIG. 31.

FIG. 48 illustrates the area of the distal pullband pin joint. In this area, the distal ends of the pullbands 1140 are secured by the distal pullband pin 1144 disposed inside the bore of the distal guide block 1160. The distal guide block 1160 is disposed in the staple cartridge holder 1030 and secured thereto as set forth above.

Figure 49:
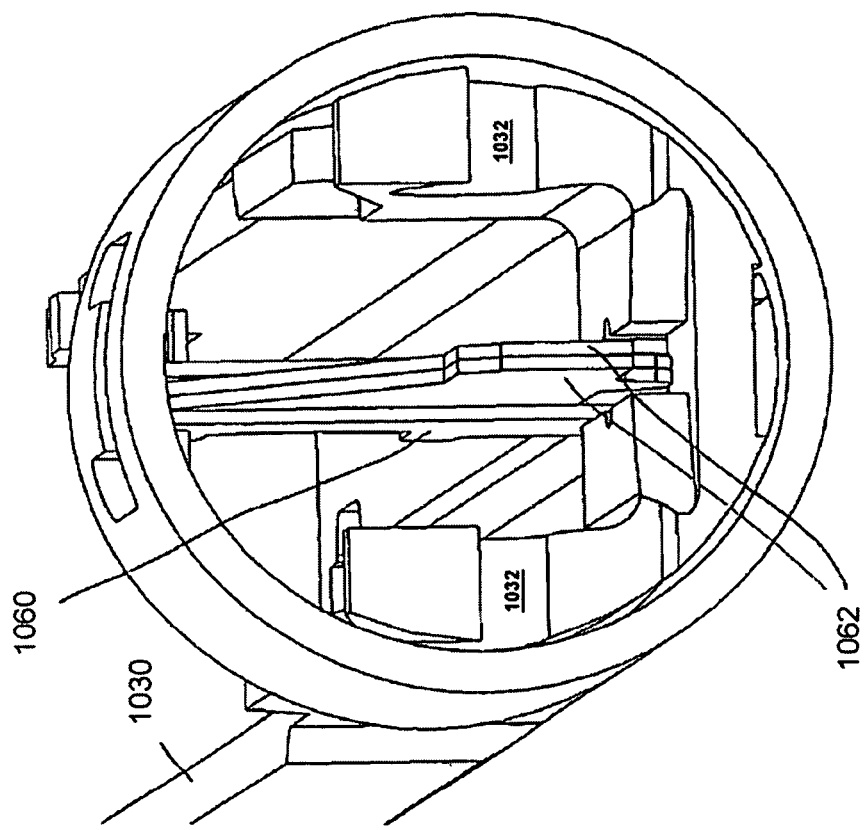
FIG. 49 is a fragmentary, enlarged, vertically transverse cross-sectional view of an anvil/upper jaw pivot slot of the device of FIG. 31.

FIG. 49 illustrates the area just proximal of the cutting blade 1060 and the fixed connection of the two knife blades 1062 inside a proximal orifice of the cutting blade 1060. This view also clearly shows the cam surfaces 1032 that allow the anvil 1020 to pivot and translate with respect to the staple cartridge holder 1030.

Figure 51:
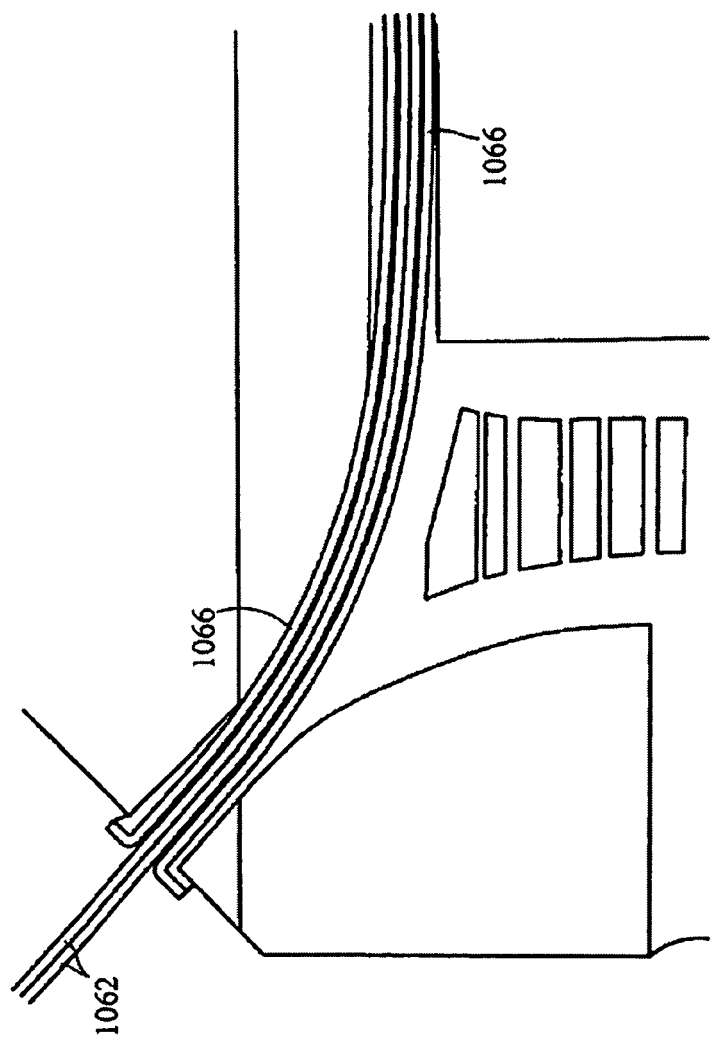
FIG. 51 is an illustration of a test bed for knife guiding blades and hammocks of the device of FIG. 31.

FIG. 50 shows a longitudinal cross-section through the spring rods 1012. Visible in this view is the entire longitudinal extent of the hammocks 1066. The distal sections of the hammocks 1066 articulate about a vertical axis near the distal end of the hammocks 1066. In FIG. 50, there exists a substantial gap between the spring rods 1012 and the hammocks 1066. If the hammocks 1066 were not present, there exists the possibility that the thin knife blades 1062 could bend and warp or kink into these gaps. By placing the hammocks 1066 therebetween, any possibility of impermissible bending of the knife blades 1062 is prevented. FIG. 51 is provided to show the extreme bending extent of the hammocks 1066 and the blades 1062 therebetween in a test bed made for such a purpose. It is noted that the upper hammock 1066 is not utilized in an upward bend with respect to FIG. 51 because it tracks the inside surface of the curve at the critical bending area. In contrast, the lower hammock 1066 is utilized to substantially prevent the knife blades 1062 therebetween (two in this exemplary embodiment) from impermissibly bending into the gap of the test bed. Because each hammock 1066 is held rigidly at either end and is made out of a substantially non-elastic material (e.g., of stainless steel), it forms a sling or "hammock" that supports the bent knife blade(s) 1062 therebetween.

Figure 52:
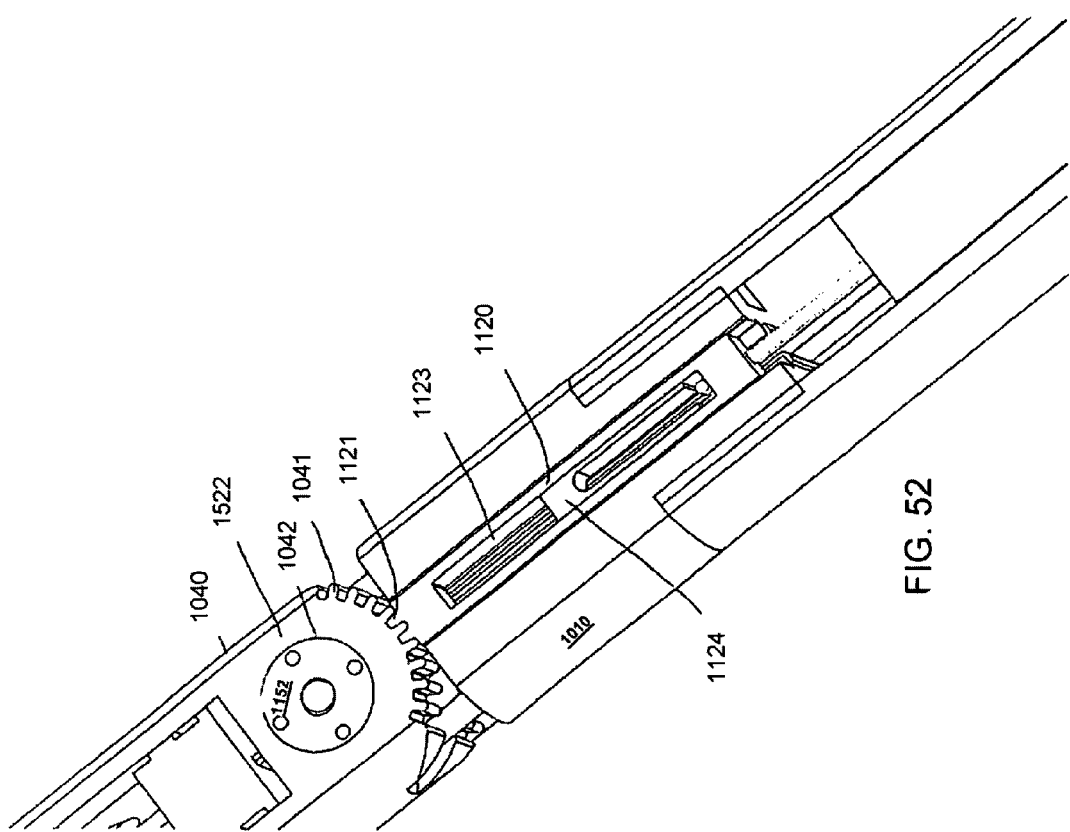
FIG. 52 is a fragmentary, enlarged, horizontally longitudinal cross-sectional view of the articulation joint portion of the device of FIG. 31 through an articulation lock release slide.

FIG. 52 illustrates a cross-section through the articulation lock release slide 1120 and clearly shows the distal connection bend of the unlock pullrod 1104 inside the slide 1120. In such a configuration, proximal displacement of the unlock pullrod 1104 causes a corresponding proximal displacement of the slide 1120 to unlock the teeth 1121 of the slide 1120 from between the corresponding teeth 1041 on the proximal side of the drum sleeve 1040. A distal bias is imparted upon the articulation lock release slide 1120 by a non-illustrated bias device that resides in a hollow 1123 and presses against the distal end of the hollow 1123 and a block 1124 that is fixed with respect to the clevis 1010.

FIG. 35 shows the connection between the unlock pullrod 1104 and the handle 1200. A rod pullblock 1105 has a longitudinal bore 1107 for receiving therein the pullrod 1104. The rod pullblock 1105 also has transverse bores 1109 for receiving non-illustrated set screws therein for securing the pullrod 1104 inside the rod pullblock 1105. An interior portion of the bell actuator 1100 is shaped to engage the rod pullblock 1105 (for example, in a form-fitting connection such as a keyhole) and displace the rod pullblock 1105 proximally when the bell actuator 1100 is moved proximally.

Figure 53:
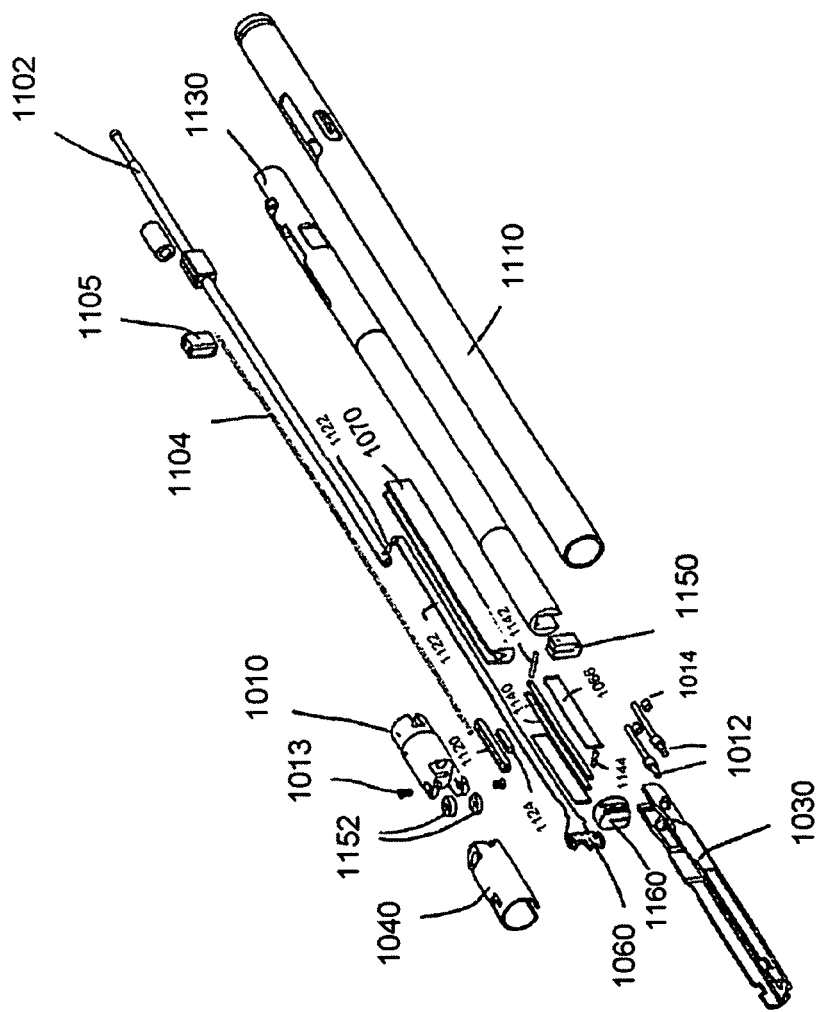
FIG. 53 is an exploded perspective view of distal components of the device of FIG. 31 viewed from the distal end thereof and without the anvil.

FIG. 53 is an exploded perspective view of the distal parts of the endostapler as viewed from the distal end thereof.

It is noted that the clevis 1010 in FIGS. 34 to 53 is a one-piece part. Alternatively, the clevis 1010 can be molded in two halves. In such a case, the pucks 1152 can be eliminated and, instead, form parts of each of the two clevis halves, thereby eliminating the need for the screws 1013 because the outer tube 1110 will hold the two halves together when attached to the proximal end of the clevis 1010. Such a configuration is illustrated in the endostapler embodiment of FIGS. 54 et seq.

Figure 54:
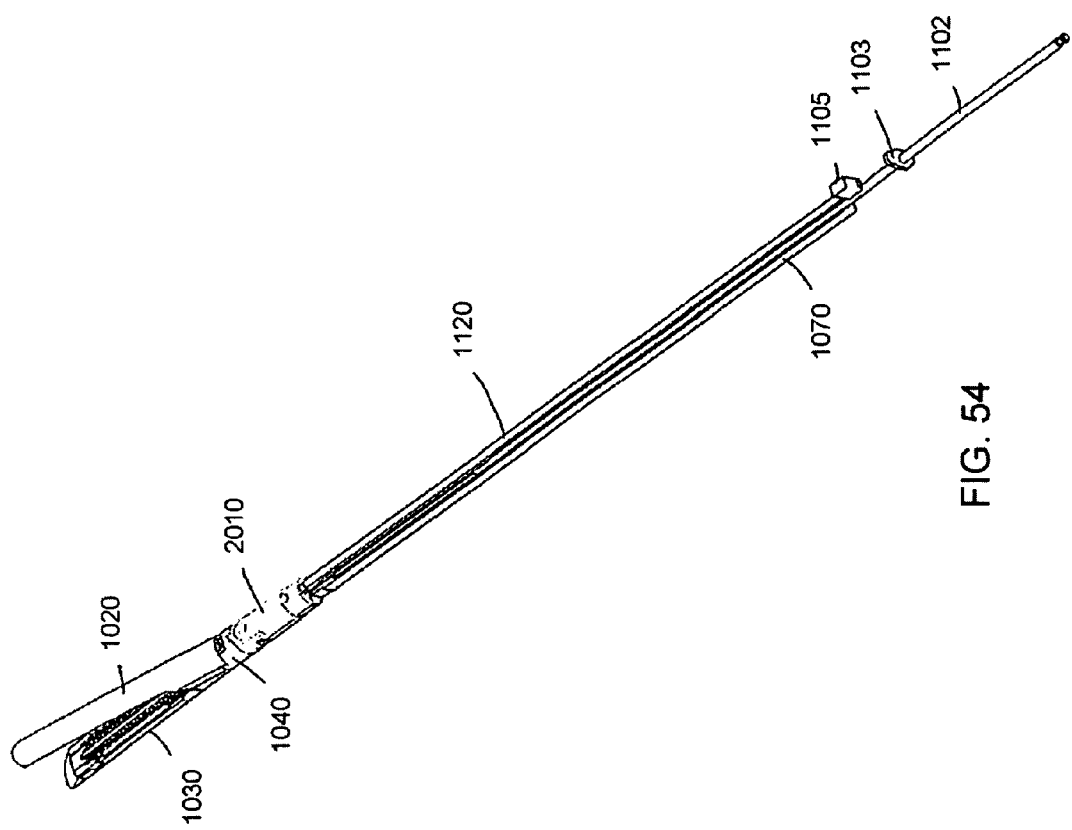
FIG. 54 is a perspective view of an articulating distal portion of a fourth embodiment of the end effector according to the invention with the inner and outer tubes removed.

FIG. 54 shows some internal parts of this fourth embodiment of the end effector. The anvil 1020 is disposed opposite the staple cartridge holder 1030 and a closure ring 1040 surrounds the proximal end of the staple cartridge holder 1030. The inner and outer tubes 1130, 1110 are removed so that the articulation lock release slide 1120, the pushrod 1102, and the pushrod-blade support 1070 can be seen clearly. A screen door 1103 is mounted around the pushrod 1102 and inside the inner and outer tubes 1130, 1110 and the bell actuator 1100. The handle 1200 and bell actuator 1100 are removed for clarity. The screen door 1103 restricts movement of the pushrod 1102 to only one direction—distal—because the knife/cutting blade 1060 only moves in the distal direction.

Figure 55:
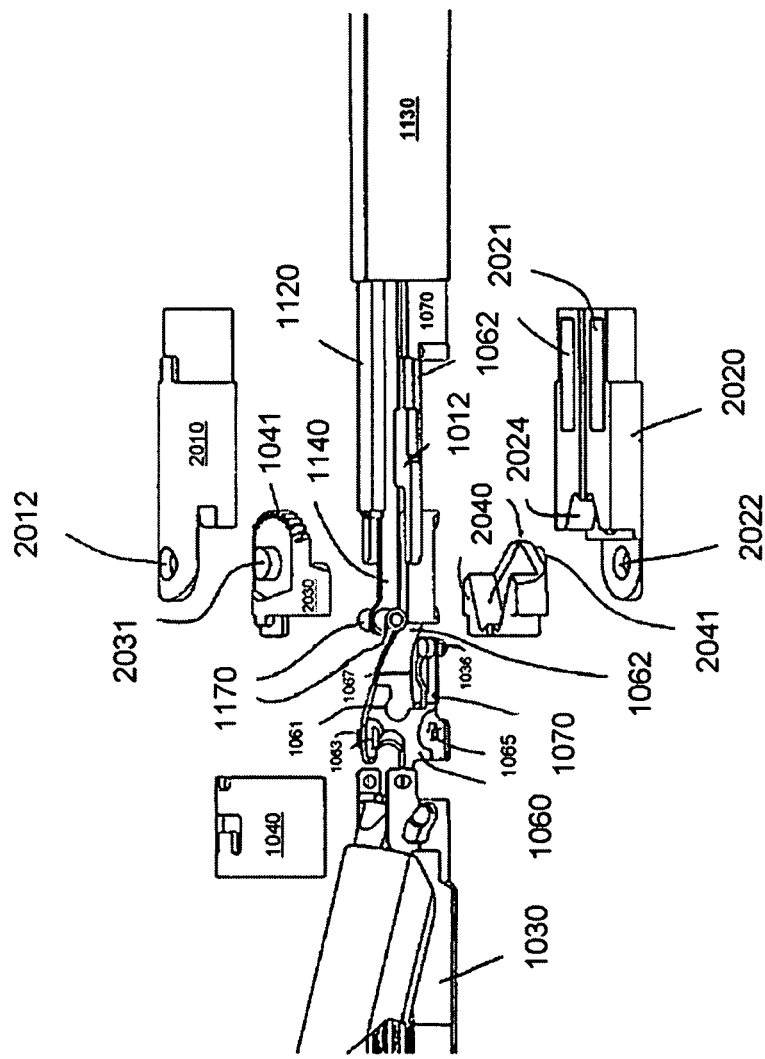
FIG. 55 is a fragmentary, enlarged, and exploded perspective view of an articulating portion of the end effector of FIG. 54 rotated with the top inward towards the viewer with the outer tube removed.
Figure 56:
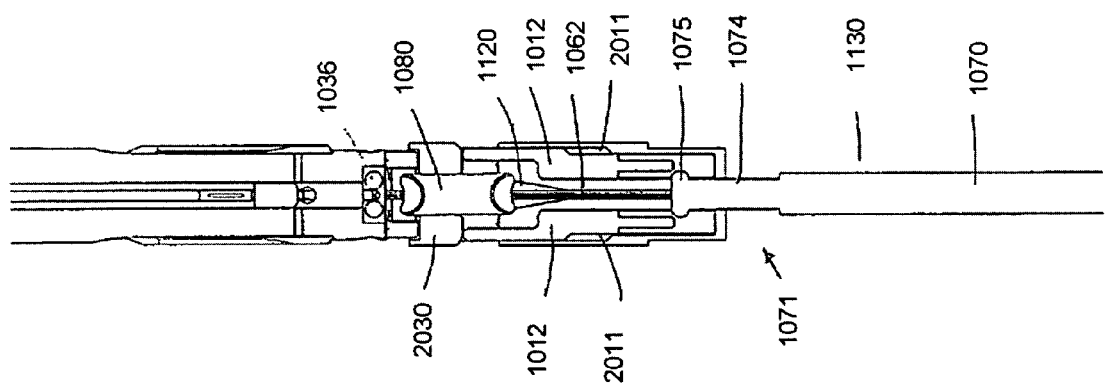
FIG. 56 is a fragmentary, enlarged, bottom plan view of the articulating portion of the end effector of FIG. 54 with the lower clevis and the closure ring removed.
Figure 59:
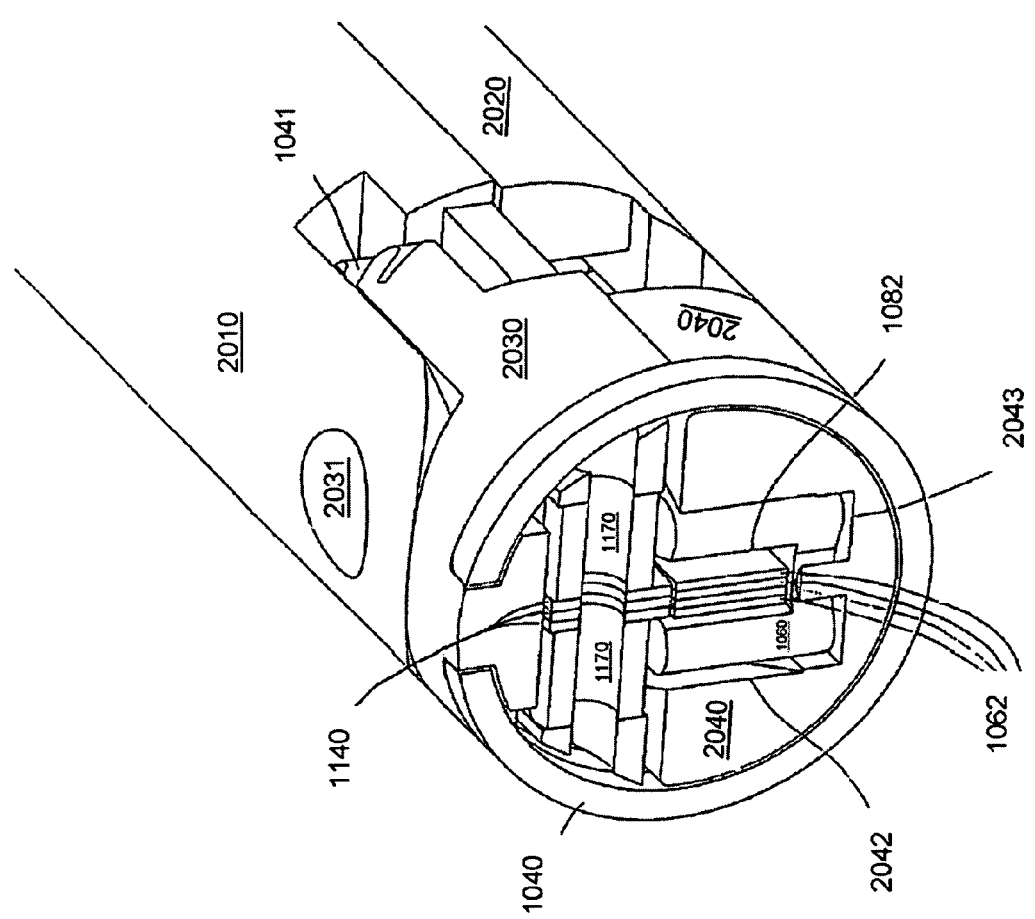
FIG. 59 is a fragmentary, vertically transverse, cross-sectional view of the articulating portion of the end effector of FIG. 54 through a distal end of the dogbone guide.

The two-part clevis is best illustrated in the views of FIGS. 55 and 56. These figures show various internal features of the end effector of FIG. 54 with the outer tube 1110 removed. In the exploded view of FIG. 55, connection of the pullband(s) 1140 to the staple cartridge holder 1030 is apparent. A non-illustrated pin (see also FIG. 59) passes through a first proximal flange of the holder 1030, a first spacer 1170, a distal flange of the pullband 1140, a second spacer 1170, and a second opposing proximal flange of the holder 1030, respectively. The closure ring 1040, as shown in FIG. 59, holds the pin therein to provide the longitudinal connection of these components.

Various features of the knife/cutting blade 1060 are also revealed in FIG. 55. The blade 1060 has a proximal recess 1061 for connecting a distal end of the knife blade 1062 thereto. In the exemplary embodiment, the recess 1061 and distal end form a keyhole-shaped lock. The upper half of the blade 1060 has two opposing guide wings 1063 having an exterior shape that fits into a corresponding groove inside the bottom surface of the upper anvil 1020. The lower half of the blade 1060 also has two opposing guide wings 1065. The holder 1030 has a groove inside the top surface thereof for receiving the lower wings 1065 therein. These two pairs of wings 1063, 1065 ensure that the anvil 1020 and the holder 1030 are at a fixed parallel position when the blade 1060 is traversing therealong in the cutting and stapling process. Also disposed on the lower half of the blade 1060 is a proximally extending flange 1067. A plate spring 1090 is attached to the staple cartridge holder 1030 by rivets 1036. The plate spring 1090 and other features of the blade 1060 will be described in greater detail below.

Figure 58:
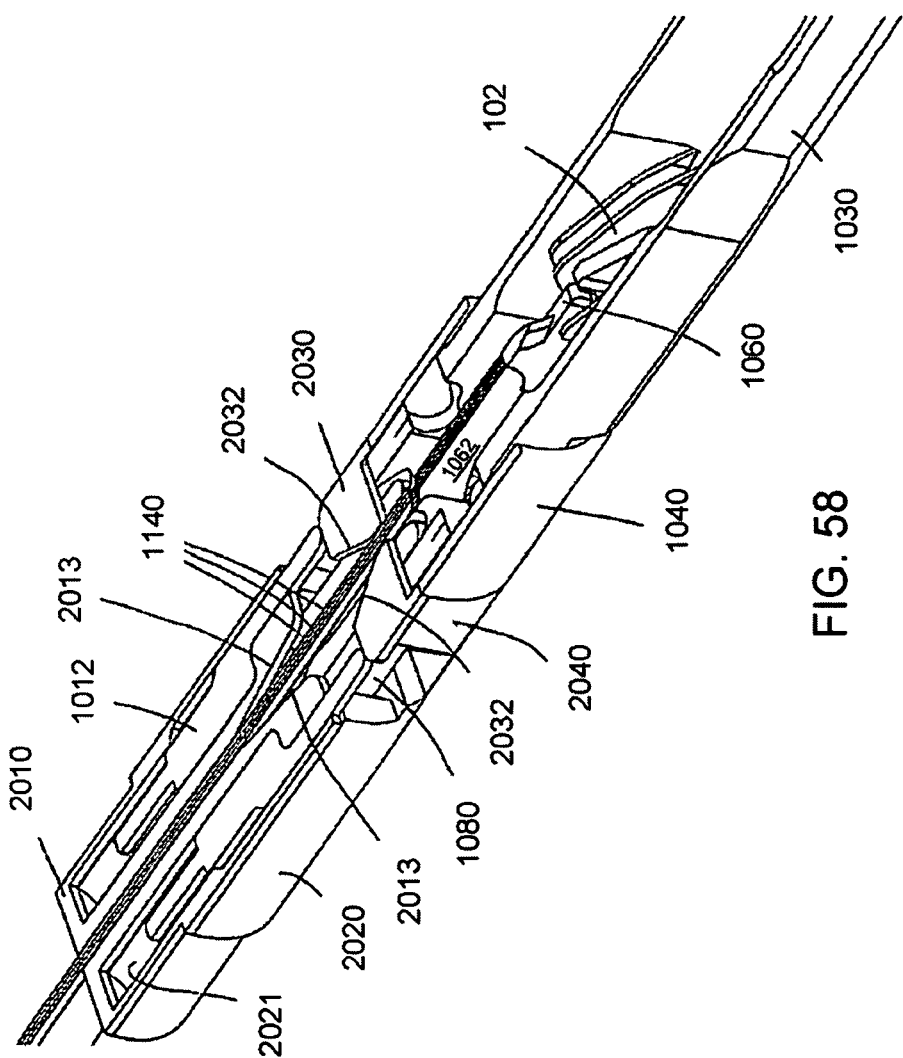
FIG. 58 is a fragmentary, vertically longitudinal, cross-sectional view of the articulating portion of the end effector of FIG. 54 through the spring rods with the inner tube and the pushrod-blade support removed.

FIGS. 55 and 56 also show various portions of the two-part clevis 2010, 2020. As can be seen in FIGS. 56 and 58, the interior surface of the upper clevis half 2010 defines two cavities 2011 that each house a respective spring rod 1012 and the non-illustrated bias device for that spring rod 1012. In the exemplary embodiment shown, the upper clevis half 2010 defines the entire cavity 2011 for the spring rods 1012 and the lower clevis half 2020 defines the bottom cavity portion 2021 for accommodating only the bias device. The clevis halves 2010, 2020 also define articulation ports 2012, 2022 for receiving therein articulation bosses 2031, 2041 on each of the two dogbone clevis parts 2030, 2040.

Figure 57:
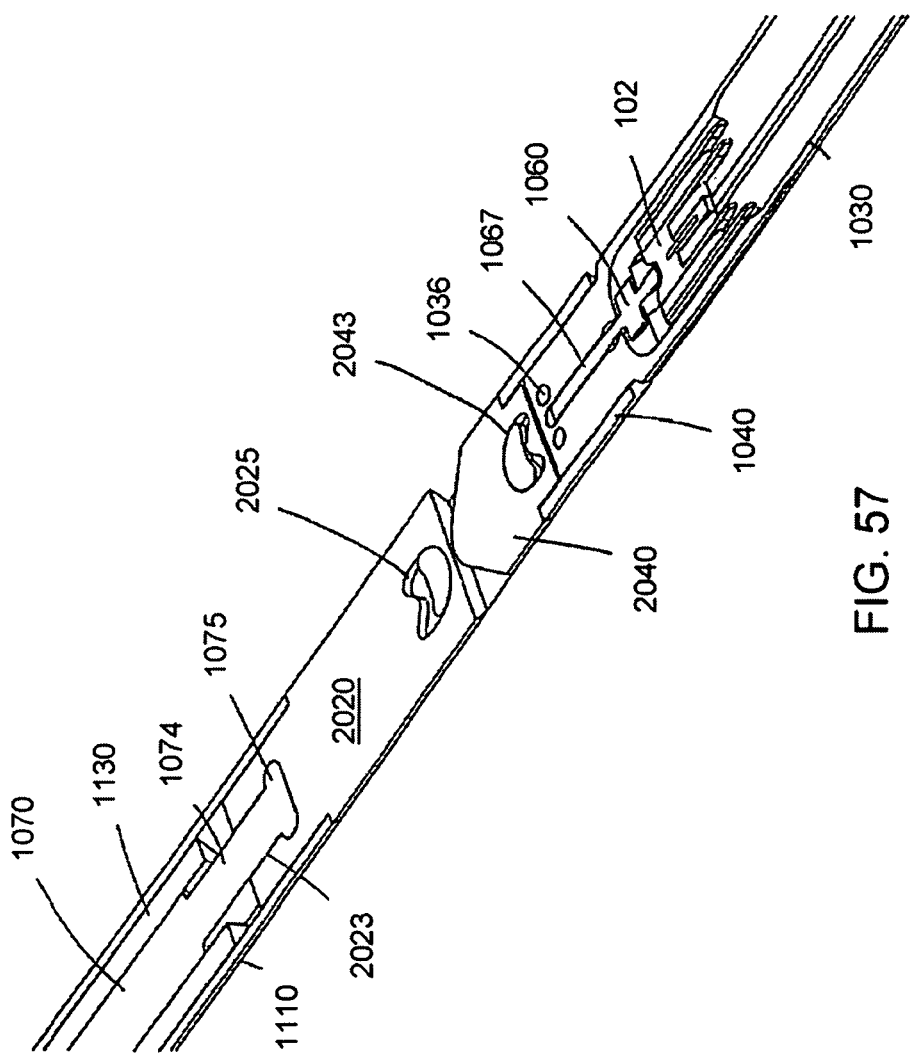
FIG. 57 is a fragmentary, horizontally longitudinal, cross-sectional view of the articulating portion of the end effector of FIG. 54 through a lower end of the dogbone guide.

FIGS. 56 and 57 illustrate the longitudinal connectivity of the features within the outer tube 1110. The pushrod-blade support 1070 is disposed inside a lower channel of the inner tube 1130. This pushrod-blade support 1070 also has a distal extension 1071 with a narrow proximal neck 1074 and a relatively wider distal head 1075. With a corresponding recess 2023 in the bottom of the lower clevis half 2020, the distal extension 1071 can be longitudinally fixed to the clevis half 2020 and, therefore, the remainder of the clevis.

The outer tube 1110 and the lower clevis half 2020 are removed in FIG. 56 to illustrate the configuration of the spring rods 1012 inside the spring rod cavities 2011. Again, the spring rod bias devices (e.g., coil springs) are not shown in the cavities 2011 for clarity. With various parts removed, the articulating extent of the pullbands 1140 is clearly shown in FIG. 56. The supporting surfaces for the pullbands 1140 inside the upper clevis half 2010 are visible at the cross-section plane of FIG. 58. The upper dogbone clevis 2030 has two opposing supporting surfaces 2032 each at a similar acute angle with respect to the centerline of the un-articulated pullbands 1140. Likewise, the upper clevis half 2010 has two opposing supporting surfaces 2013 each at an acute angle with respect to the centerline of the un-articulated pullbands 1140.

Figure 62:
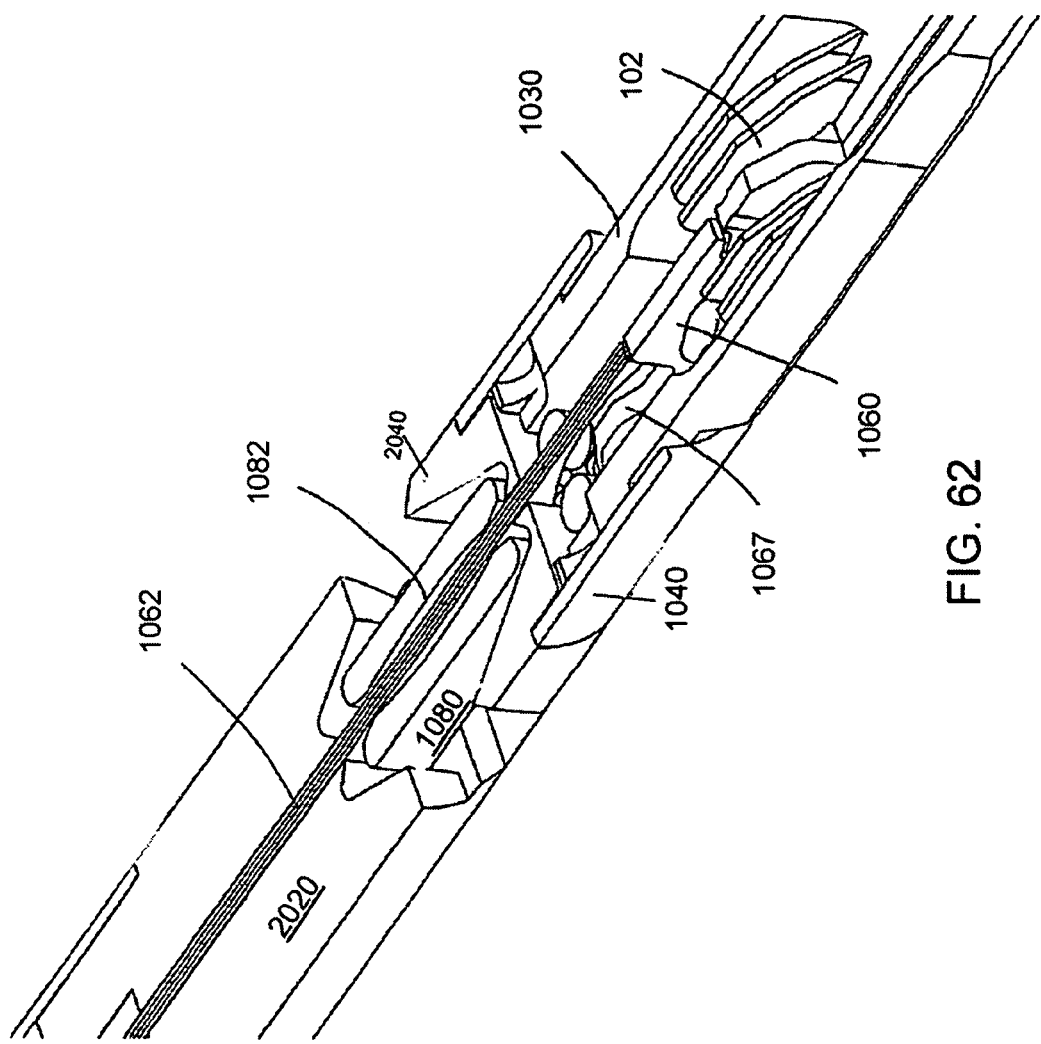
FIG. 62 is a fragmentary, horizontally longitudinal, cross-sectional view of the articulating portion of the end effector of FIG. 54 through a high intermediate portion of the dogbone guide.
Figure 66:
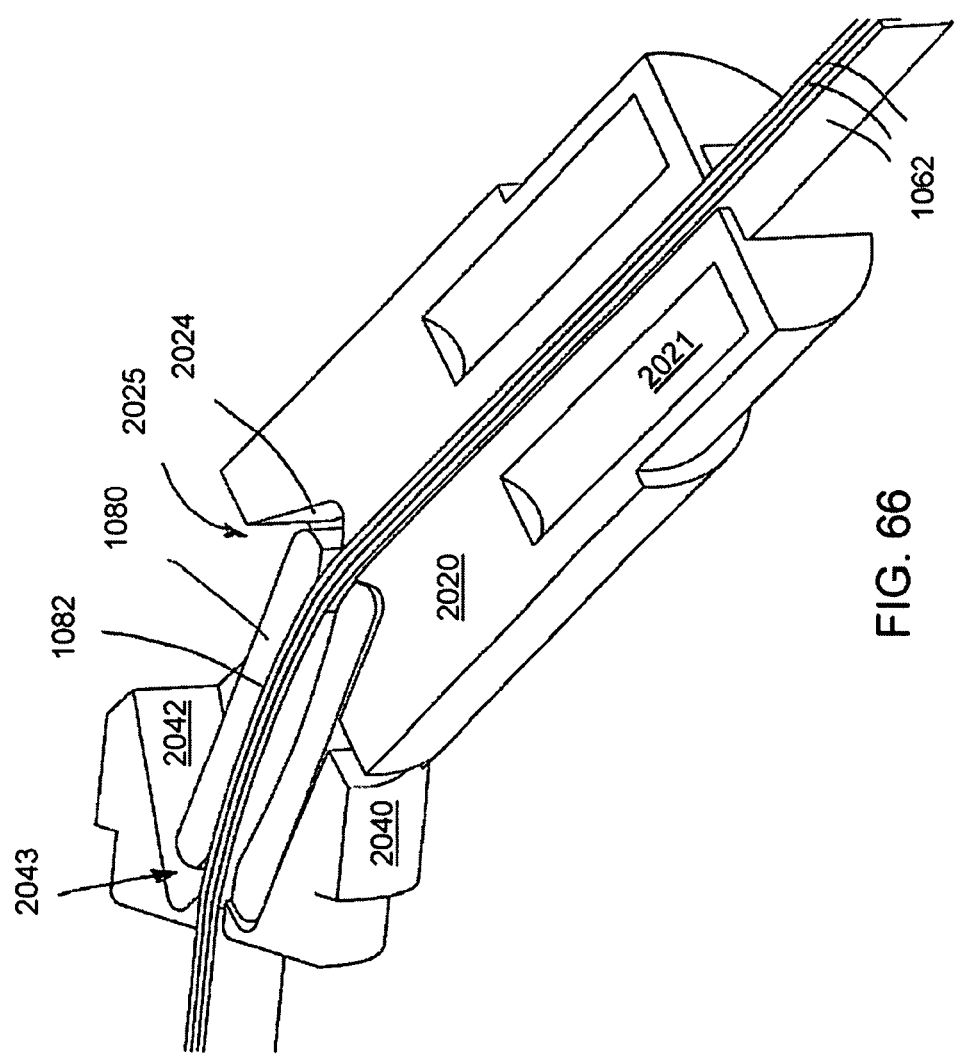
FIG. 66 is a perspective view of the lower clevis, the lower dogbone clevis, the dogbone guide, and three adjacent knife blades of the end effector of FIG. 54.

The opposite viewing direction towards the interior of the lower clevis half 2020 is illustrated in FIGS. 55 and 58. The articulation section for the knife blades 1062 is illustrated along with the supporting surfaces 2042 for the dogbone 1080 inside the lower dogbone clevis 2040 and the supporting surfaces 2024 for the dogbone 1080 inside the lower clevis half 2010. Also visible in this orientation are guiding and supporting surfaces for the dogbone guide 1080. In FIG. 57, it is seen that the lower dogbone clevis has a kidney-shaped distal dogbone depression 2043 and the lower clevis half 2010 has a kidney-shaped proximal dogbone depression 2025. These depressions 2025, 2043 and surfaces 2024, 2042 are also illustrated in FIG. 66 and will be described in detail below. A further feature visible in FIGS. 59, 62, and 66 is the interior passage of the dogbone guide 1080 having left and right surfaces 1082 and will be describe in further detail below.

The distal end of the dogbone guide 1080 is shown in the vertical cross-section of FIG. 59. The distal dogbone depression 2043 houses the distal end of the dogbone guide 1080 and, when unarticulated, the dogbone guide 1080 does not touch the supporting surfaces 2042 of the lower dogbone clevis 2040.

The proximal housing for the distal end of the dogbone guide 1080 is illustrated in FIG. 60. To better reveal the features of the proximal dogbone depression 2025, the dogbone guide 1080 is removed from these figures.

Both of the depressions 2025, 2043 with the lower extending portions of the dogbone guide 1080 disposed therein are shown in horizontal, longitudinally transverse cross-section of FIG. 57. Also shown therein are the lower features of the pushrod-blade support 1070, the cutting blade 1060, and the staple sled 102 (which is a part of the removable staple cartridge 100). These features are enlarged in FIGS. 61 and 62.

Figure 63:
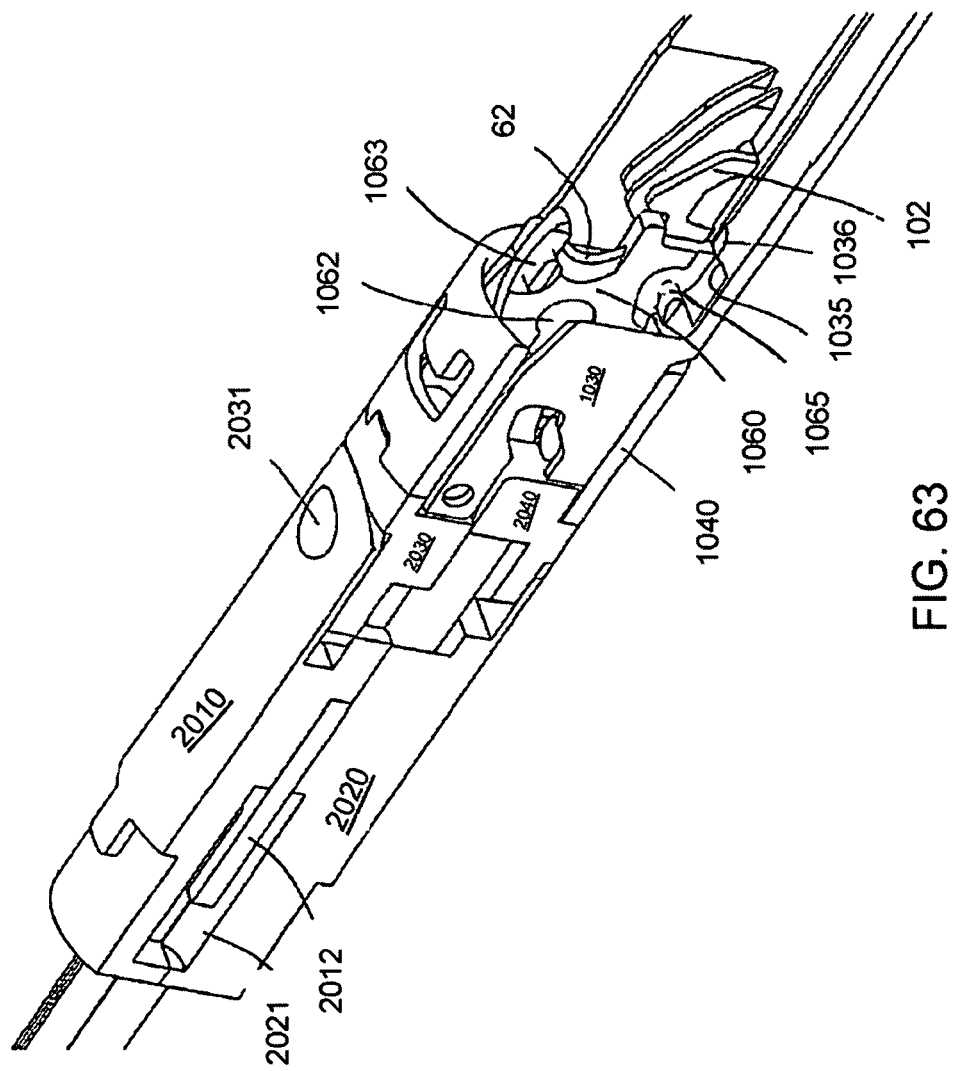
FIG. 63 is a fragmentary, vertically longitudinal, cross-sectional view of the articulating portion of the end effector of FIG. 54 through a spring rod with the inner tube, the pushrod-blade support, an anvil, and a near half of the staple sled removed.
Figure 64:
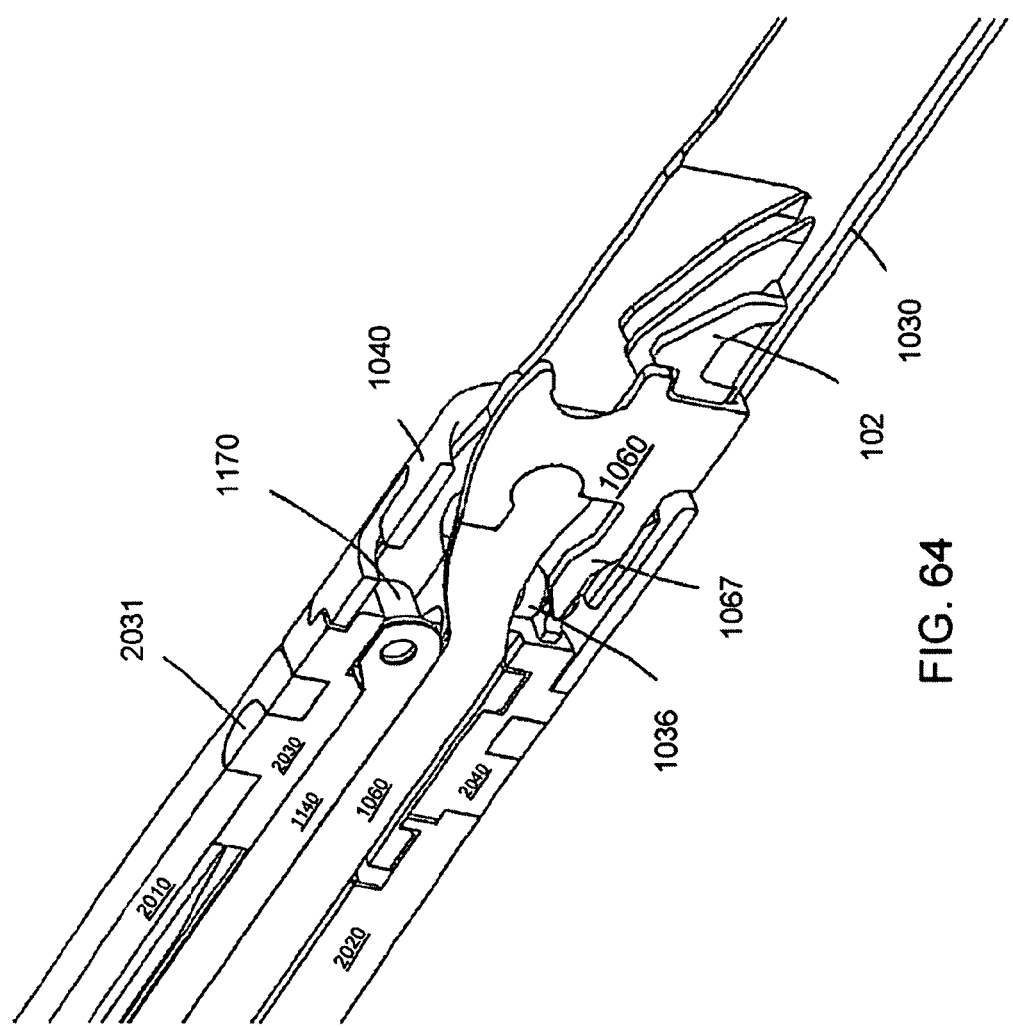
FIG. 64 is a fragmentary, vertically longitudinal, cross-sectional view of the articulating portion of the end effector of FIG. 54 through the dogbone guide with a spring plate, the anvil, and the near half of the staple sled removed.
Figure 65:
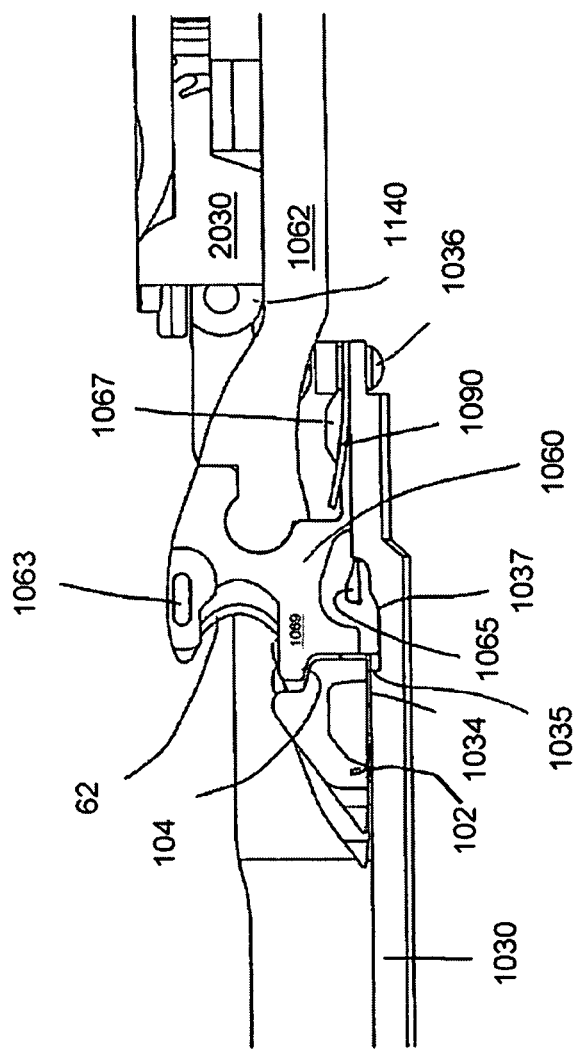
FIG. 65 is a fragmentary, vertically longitudinal, cross-sectional view of a distal end of the articulating portion of the end effector of FIG. 54 with the inner tube, the pushrod-blade support, the anvil, the closure ring, and the near half of the staple sled removed.

FIGS. 63, 64, and 65 illustrate the knife blade 1060 lock-out feature. In other words, the safety that prevents the knife blade 1060 from advancing when there is no staple cartridge 100 or a previously fired staple cartridge 100 in the staple cartridge holder 1030. For ease of understanding, the only part of the staple cartridge 100 shown in these figures is the staple sled 102.

The knife blade 1060 should be allowed to move distally only when the staple sled 102 is present at the firing-ready position, i.e., when the sled 102 is in the position illustrated in FIG. 65. If the sled 102 is not present in this position, this can mean one of two things, either there is no staple cartridge 100 in the holder 1030 or the sled 102 has already been moved distally—in other words, a partial or full firing has already occurred with the loaded staple cartridge 100. Thus, the blade 1060 should not be allowed to move, or should be restricted in its movement. Accordingly, the sled 102 is provided with a lock-out contact surface 104 and the blade 1060 is provided with a correspondingly shaped contact nose 1069. It is noted at this point that, the lower guide wings 1065 do not rest against a floor 1034 in the cartridge holder 1030 until the blade 1060 has moved distally past an edge 1035. With such a configuration, if the sled 102 is not present at the distal end of the blade 1060 to prop up the nose 1069, then the lower guide wings 1065 will follow the depression 1037 just proximal of the edge 1035 and, instead of advancing on the floor 1034, will hit the edge 1035 and stop further forward movement of the blade 1060. To assist with such contact when the sled 102 is not present, the staple cartridge 1030 has a plate spring 1090 (attached thereto by rivets 1036). With the plate spring 1090 flexed upward and pressing downward against the flange 1067 (at least until the flange 1067 is distal of the distal end of the plate spring 1090), a downwardly directed force is imparted against the blade 1060 to press the wings 1065 down into the depression 1037. Thus, as the blade 1060 advances distally without the sled 102 being present, the wings 1065 follow the lower curve of the depression 1037 and are stopped from further distal movement when the distal edge of the wings 1065 hit the edge 1035. FIG. 63, for example, shows the distal edge 1035 and two raised bosses 1038 that extend the height of the edge 1035 to insure that the wings 1065 cannot be forced over the edge 1035 when the sled 102 is not present.

FIG. 66 illustrates an exemplary movement of the dogbone 1080 within the lower clevis half 2020 and the lower dogbone clevis 2040. In the fully left articulated position of FIG. 66, the distal bottom projection of the dogbone 1080 is in a rotated position within the distal dogbone depression 2043 and the proximal bottom projection is in a rotated position within the proximal dogbone depression 2025. Importantly, the left vertical surface of the dogbone 1080 is almost fully supported on the left dogbone supporting surfaces 2024, 2042. The shapes of the depressions 2025, 2043 and the bottom projections of the dogbone 1080 are selected such that there is no elongation or compression of the dogbone 1080 but, merely, a rocking left to right when articulation of the end effector occurs.

Three side-by-side knife blades 1062 are diagrammatically illustrated in FIG. 66 within a left articulated position of the lower clevis halves 2020, 2040. When bent to the left, the knife blades 1062 are pressed against the right interior surface 1082 of the dogbone 1080. Accordingly, the interior surfaces 1082 are shaped dependent upon the extent that the end effector will be articulated. Due to the limitations of drafting the features of the invention, the blades 1062 are only shown in a diagrammatic, approximate curved orientation.

Figure 67:
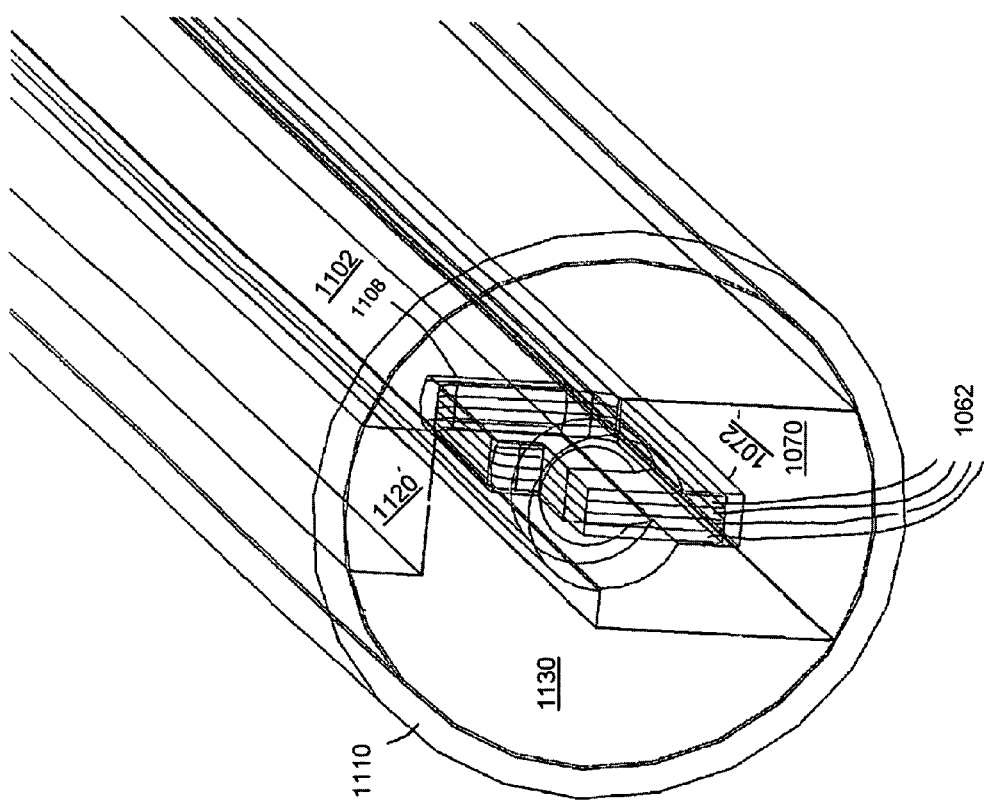
FIG. 67 is a fragmentary, wireframe, vertically transverse cross-sectional view of the end effector of FIG. 54.

To better understand some features of the knife blades 1062, enlarged views of the proximal connection to the pushrod 1102 and the pushrod-blade support 1070 are shown in FIG. 67. While a configuration having co-axially aligned knife blades 1062 and the pushrod 1102 is envisioned and possible, an offset connection shown, for example, in FIGS. 41 and 67, is used. As set forth above, the length of the knife blades 1062 make it desirable for the knife blades 1062 to be pressed down fully into the blade channel 1072 within the pushrod-blade support 1070. FIG. 41 shows a first embodiment for an offset connection that biases the blades 1062 into the channel 1072. FIG. 67 shows a second embodiment for this offset connection. In this second embodiment, the blades 1062 are not fixedly connected to the pushrod 1102 as in the first embodiment (connected by transverse pushrod pin 1122). Instead, the pushrod 1102 is formed with a chamber 1108 into which is inserted the proximal end of the blades 1062. By forming the chamber 1108 in a shape that axially longitudinally holds the blades 1062 (e.g., with a transverse offset), there is no need for a fixed connection. In this embodiment, the chamber 1108 is approximately L-shaped in vertical cross-section to provide such a transverse offset, but it can be any number of different shapes.

Figure 69:
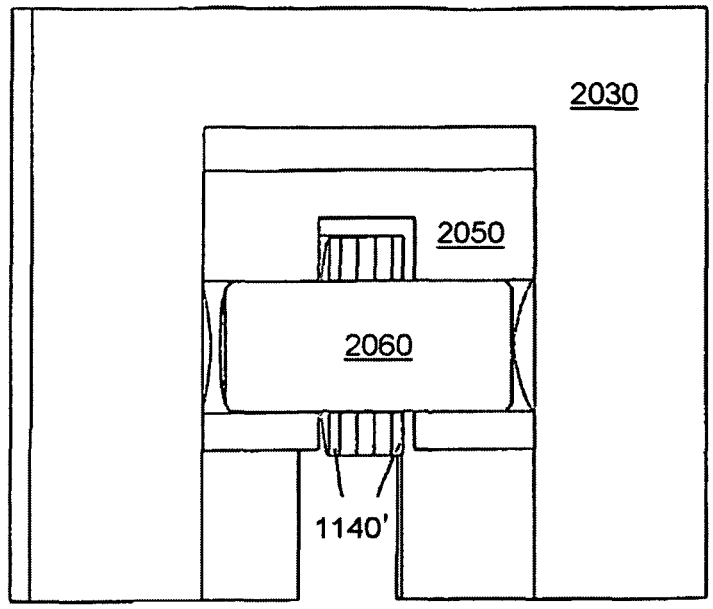
FIG. 69 is a fragmentary, vertically transverse cross-sectional view of the distal connection of FIG. 68.
Figure 70:
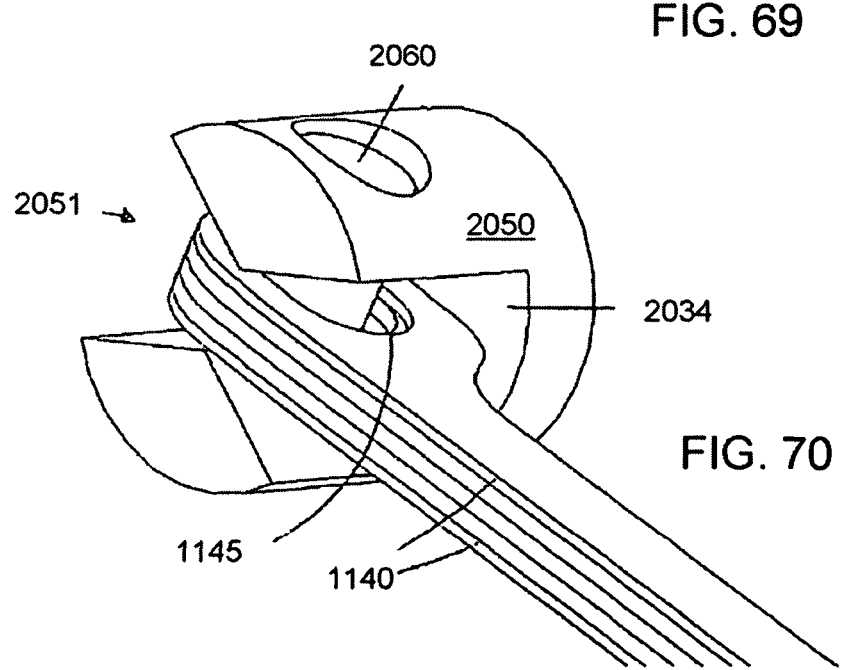
FIG. 70 is a fragmentary perspective view from below of a portion of the distal connection of FIG. 68.

The distal connection of the pullbands 1140 is shown particularly well in FIG. 59. It is noted that, in such a configuration, left or right articulation imparts a bend on each of the two, three, four, or more adjacent pullbands 1140. Because each pullband 1140 has a fixed length, and because the pullbands 1140 are stacked along side one another, articulation in a given direction bends each of the pullbands 1140 differently, even if the difference is very slight. To compensate for such differences in bending, an alternative embodiment of the distal connection is provided and is shown in FIGS. 68 to 70. For clarity and simplicity, only a portion of the upper dogbone clevis 2030 is shown diagrammatically in these figures.

This alternative embodiment replaces the spacers 1170 in the first embodiment. Here, five pullbands 1140 are disposed along side one another. The upper dogbone clevis 2030 defines an interior bore 2033 (e.g., a circular bore) into which is inserted a piston 2050 having an exterior shape corresponding to the interior shape of the bore 2033. The bore 2033 has a proximal window 2034 through which the pullbands 1140 project into the bore 2033. The window 2034 has a width approximately equal (but just slightly larger than) the total width of the pullbands 1140.

The piston 2050 has a transverse bore into which is threaded a proximal pullband pin 2060 that functions as an axle when threaded through the piston 2050 and through the distal pullband bore 1145 of each of the pullbands 1140. See FIG. 70. The interior 2051 of the piston 2050 does not have a shape corresponding to the width of the stacked pullbands 1140. Instead, the interior opening for receiving the distal end of the pullbands 1140 has a winged horizontally cross-sectional shape.

As the end effector articulates, the distal end of the pullbands 1140 are bent into a curve. When adjacent parallel plates such as the pullbands 1140 are bent together, the outside plates move differently than the middle or inner plates. This non-homogeneous movement is compensated for by the winged opening 2051 and the oval-shaped distal pullband bores 1145. As the end effector is articulated, the bending forces imparted upon the pullbands 1140 cause the piston 2050 to rotate within the bore 2033 of the upper dogbone clevis 2030. The more that the end effector articulates, the more the piston 2050 rotates, until full articulation presses the outside pullband 1140 against the inner surface of the winged opening 2051. At this point, the proximal ends of each pullband 1140 are aligned but the distal ends shown in FIGS. 68 to 70 are not. The presence of the ovular openings 1145 allow the pullbands 1140 to move slightly with respect to one another.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

We claim:

1. A medical device, comprising:
    a control handle;
    a surgical end effector; and
    a passive articulating joint connecting said end effector to said control handle, said control handle having an articulation joint actuator connected to said passive articulation joint to change an articulation state of said passive articulation joint.

2. The medical device according to claim 1, wherein said passive articulation joint:
    articulatingly holds said end effector in position when said articulation joint actuator is not actuated; and
    articulatingly releases said end effector when said articulation joint actuator is actuated.

3. The medical device according to claim 1, wherein said passive articulation joint:
articulatingly holds said end effector in a given articulated position when said articulation joint actuator is not actuated; and
articulatingly releases said end effector to articulate freely when said articulation joint actuator is actuated.

4. The medical device according to claim 1, wherein said articulation joint actuator causes said passive articulation joint:
to articulatingly hold said end effector in position when said articulation joint actuator is not actuated; and
to articulatingly release said end effector when said articulation joint actuator is actuated.

5. The medical device according to claim 1, wherein said articulation joint actuator has an unactuated state and an actuated state and articulatingly releases said passive articulation joint when in said actuated state.

6. The medical device according to claim 5, wherein said end effector articulates when:
said articulation joint actuator is actuated; and
an external force is applied to said end effector.

7. The medical device according to claim 5, wherein said end effector freely articulates dependent upon forces acting upon said end effector when said articulation joint actuator is actuated.

8. The medical device according to claim 5, wherein said end effector:
freely responds to forces acting upon said end effector to cause articulation motion thereof when said articulation joint actuator is actuated; and
is locked in a given articulation position when said articulation joint actuator is unactuated.

9. The medical device according to claim 5, wherein:
said end effector is a surgical stapling end effector having at least one of a stapling device with staples and a cutting device with a blade; and
said control handle has:
a stapler closing actuator closing said stapling device when actuated;
a staple firing actuator at least one of stapling said staples and cutting tissue with said cutting device when actuated; and
said stapler closing actuator and said staple firing actuator are different from said articulation joint actuator.

10. The medical device according to claim 9, further comprising:
at least one first flexible beam connecting said control handle to said staple firing actuator through said passive articulation joint;
at least one second flexible beam longitudinally connecting said end effector to said control handle through said passive articulation joint; and
said at least one first flexible beam and said at least one second flexible beam flexing in a corresponding way to an articulation of said passive articulation joint.

11. The medical device according to claim 1, wherein actuation of said articulation joint actuator removes an articulation lock on said end effector.

12. The medical device according to claim 1, wherein:
said articulation joint actuator has a pull-lock with distally directed teeth;
said passive articulation joint has a gear with proximally directed teeth interlocked with said distally directed teeth when said articulation joint actuator is unactuated; and
said articulation joint actuator disengages said distally directed teeth from said proximally directed teeth to articulating unlock said end effector when said articulation joint actuator is unactuated.

13. The medical device according to claim 1, wherein said articulation joint actuator is a pull-to-release and release-to-relock trigger assembly.

14. A medical device, comprising:
a control handle;
a surgical end effector; and
a passive articulating joint connecting said end effector to said control handle, wherein actuation of at least a part of said control handle articulatingly frees said passive articulation joint when said part is actuated.

15. A medical device, comprising:
a control handle;
a surgical end effector; and
a passive articulating joint connecting said end effector to said control handle, wherein actuation of at least a part of said control handle releases said passive articulation joint to freely articulate when said part is actuated.

16. A medical device, comprising:
a control handle;
a surgical end effector; and
a passive articulating joint connecting said end effector to said control handle, wherein said control handle has an articulation joint actuator holding said passive articulation joint in position when not actuated and releasing said passive articulation joint when actuated.

17. A medical device, comprising:
a control handle;
a surgical end effector; and
a passive articulating joint connecting said end effector to said control handle, wherein said control handle articulatingly releases said passive articulation joint when actuated.

18. A medical device, comprising:
a control handle having an articulation joint actuator with an unactuated state and an actuated state;
a surgical end effector having an articulation lock with a locked articulation state and an unlocked articulation state; and
a passive articulating joint connecting said end effector to said control handle, said articulation joint actuator:
changing said articulation lock from said locked articulation state to said unlocked articulation state when changed from said unactuated state to said actuated state; and
changing said articulation lock from said unlocked articulation state to said locked articulation state when changed from said actuated state to said unactuated state.

19. A medical device, comprising:
a control handle having a first longitudinal axis;
a surgical end effector having a second longitudinal axis; and
a passive articulating joint connecting said end effector to said control handle, wherein:
at least one of said control handle, said end effector, and said passive articulating joint has an alignment device; and
said alignment device biases said end effector to substantially align said first and said second longitudinal axes when said articulation joint actuator is actuated.

20. The medical device according to claim 19, wherein said alignment device is a center-biasing device.

21. A medical device, comprising:
a control handle having an articulation joint actuator, said articulation joint actuator having an unactuated state and an actuated state;
a surgical end effector;
a passive articulating joint connecting said end effector to said control handle; and
said articulation joint actuator:
   when in said unactuated state, holding said passive articulation joint and, thereby, said end effector, in a substantially fixed articulation position; and
   when in said actuated state, releasing said passive articulation joint into a freely articulating state to permit free articulation of said end effector with respect to said control handle dependent upon external forces acting upon said end effector.

22. A medical device, comprising:
a surgical stapling end effector having at least one of a stapling device with staples and a cutting device with a blade;
a control handle having:
   a stapler closing actuator closing said stapling device when actuated;
   a staple firing actuator at least one of stapling said staples and cutting tissue with said cutting device when actuated; and
   an articulation joint actuator having an unactuated state and an actuated state;
a passive articulating joint connecting said end effector to said control handle; and
said end effector:
   freely articulating dependent upon forces acting upon said end effector when said articulation joint actuator is actuated; and
   being locked in a given articulation position when said articulation joint actuator is unactuated.

23. A method for operating an end effector of a medical device, which comprises:
   retaining a passive articulation joint controlling articulation movement of an end effector in a stable position with an articulation lock; and
   actuating a release of the articulation lock to unlock the passive articulation joint and permit articulating motion of the end effector through the passive articulation joint dependent upon external forces acting upon the end effector.

24. The method according to claim 23, which further comprises passively moving the end effector into an articulated position.

25. The method according to claim 23, which further comprises passively moving the end effector into an articulated position by pressing a portion of the end effector against a feature of the environment.

26. A method for operating an end effector of a medical device, which comprises:
   retaining a passive articulation joint in a locked state with an articulation lock; and
   actuating the articulation lock to unlock the passive articulation joint and permit articulating motion of the passive articulation joint dependent upon external forces acting upon the end effector.

27. The method according to claim 26, which further comprises applying a force to the end effector to articulate the end effector into a desired articulated position.

28. The method according to claim 27, which further comprises removing the actuation of the articulation lock to lock the passive articulation joint and, thereby, prevent further articulating motion of the end effector.

29. The method according to claim 28, which further comprises carrying out the retaining, actuating, applying and removing steps with one-hand.

30. The method according to claim 28, which further comprises repeating the retaining, actuating, applying, and removing steps to place the end effector in the desired articulated position.

* * * * *